(12) United States Patent
Ratnam

(10) Patent No.: US 11,185,527 B2
(45) Date of Patent: Nov. 30, 2021

(54) METHODS AND COMPOSITIONS RELATING TO STEROID HORMONE RECEPTOR-DEPENDENT CANCERS

(71) Applicant: Wayne State University, Detroit, MI (US)

(72) Inventor: Manohar Ratnam, Toledo, OH (US)

(73) Assignee: Wayne State University, Detroit, MI (US)

(*) Notice: Subject to any disclaimer, the term of this patent is extended or adjusted under 35 U.S.C. 154(b) by 32 days.

(21) Appl. No.: 16/626,659

(22) PCT Filed: Jun. 26, 2018

(86) PCT No.: PCT/US2018/039551
§ 371 (c)(1),
(2) Date: Dec. 26, 2019

(87) PCT Pub. No.: WO2019/005829
PCT Pub. Date: Jan. 3, 2019

(65) Prior Publication Data
US 2020/0155501 A1    May 21, 2020

Related U.S. Application Data

(60) Provisional application No. 62/524,879, filed on Jun. 26, 2017.

(51) Int. Cl.
*A61K 31/353* (2006.01)
*A61P 35/00* (2006.01)
*A61K 45/06* (2006.01)

(52) U.S. Cl.
CPC ............ *A61K 31/353* (2013.01); *A61K 45/06* (2013.01); *A61P 35/00* (2018.01)

(58) Field of Classification Search
CPC ........ A61K 31/353; A61K 45/06; A61P 35/00
(Continued)

(56) References Cited

U.S. PATENT DOCUMENTS

| 6,774,104 B1 | 8/2004 | Sawai et al. |
| 8,017,649 B2 | 9/2011 | Jarrott et al. |
| 9,089,546 B2 | 7/2015 | Chen |

FOREIGN PATENT DOCUMENTS

| RU | 225141 I C2 | 5/2005 |
| RU | 2431634 C2 | 10/2011 |
| RU | 2455002 C2 | 7/2012 |

OTHER PUBLICATIONS

Cushman et al, Cytotoxicities of some flavonoid analogs, Journal of Natural Products (1991), 54(6), 1656-60. (Year: 1991).*

(Continued)

*Primary Examiner* — Taylor V Oh
(74) *Attorney, Agent, or Firm* — Julie K. Staple; Dinsmore & Shohl LLP

(57) ABSTRACT

There is a continuing need for methods and compositions relating to hormone-receptor-dependent cancers, including pharmaceutical compositions including one or more compounds having activity against steroid hormone-receptor-dependent cancer and methods of treatment of a steroid hormone-receptor-dependent cancer in a subject using said pharmaceutical compositions. ELK1 is a steroid hormone receptor tethering, protein that is implicated in hormone receptor dependent cancers. Compositions and methods according to aspects of the present invention inhibit the association of steroid hormone receptors with ELK1 providing activity against steroid hormone-receptor-dependent cancer. Such compositions are provided including any one or more of: chemical compound structures I, II, III, IV, V, VI, VII, one or more derivatives, and/or one or more: pharmaceutically acceptable esters and/or one or more pharmaceu- (Continued)

tically acceptable salts, of any thereof, wherein a pharmaceutically acceptable carrier may be included in the compositions.

12 Claims, 38 Drawing Sheets

Specification includes a Sequence Listing.

(58) Field of Classification Search
USPC .......................................................... 514/456
See application file for complete search history.

(56) References Cited

OTHER PUBLICATIONS

Mrug, G. et al., Synthesis and aminomethylation of 7-hydroxy-5-methoxylsoflavones, Chemistry of Natural Compounds, 49(2): 235-241, May 2013 (Russian original No. 2, Mar.-Apr. 2013).
Teiten, M. et al., Anti-proliferative potential of curcumin in androgen-dependent prostate cancer cells occurs through modulation of the Wingless signaling pathway, International Journal of Oncology, 38: 603-611, 2011.
Nadasi, E. et al., Effect of a Plant-derived Natural Compound, Flavin 7, on the ERK Signaling Pathway in Immortalized Mouse Proximal Tubule Cells, in vivo, 21: 871-876, 2007.
Scherbakov, A. et al., Apigenin inhibits the growth of breast cancer cells: the role of ERa and HER2/neu, Acta Naturae, 3(26): 149-155. 2015.
International Search Report/Written Opinion for PCT/US 2018/039551, dated Sep. 27, 2018.

\* cited by examiner

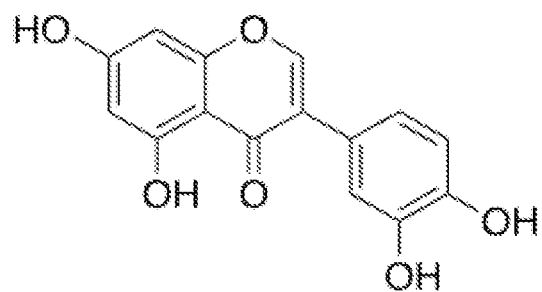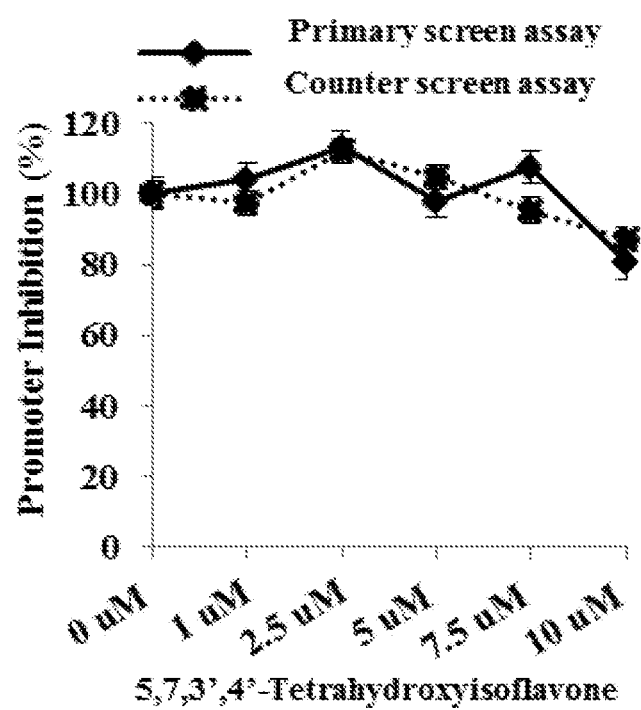
FIG. 1B

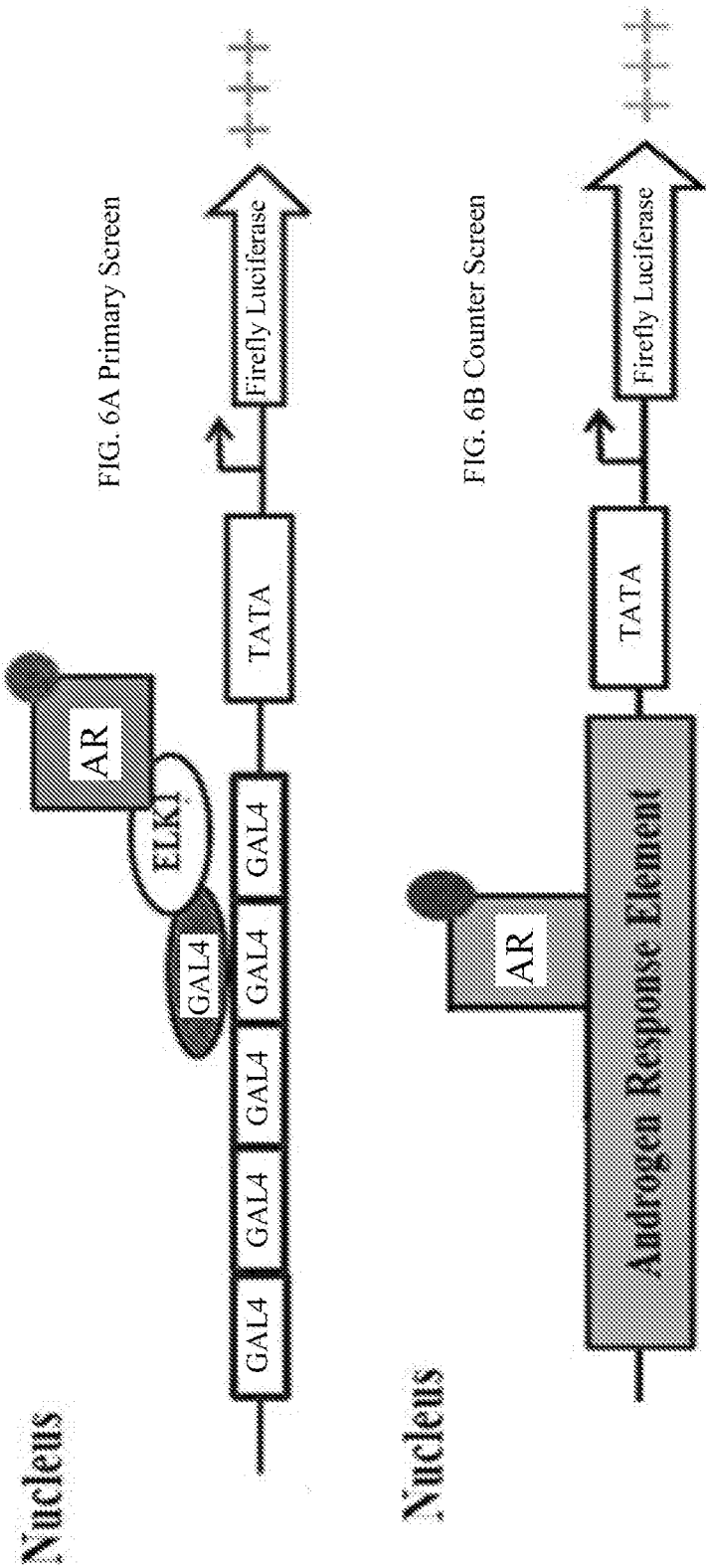

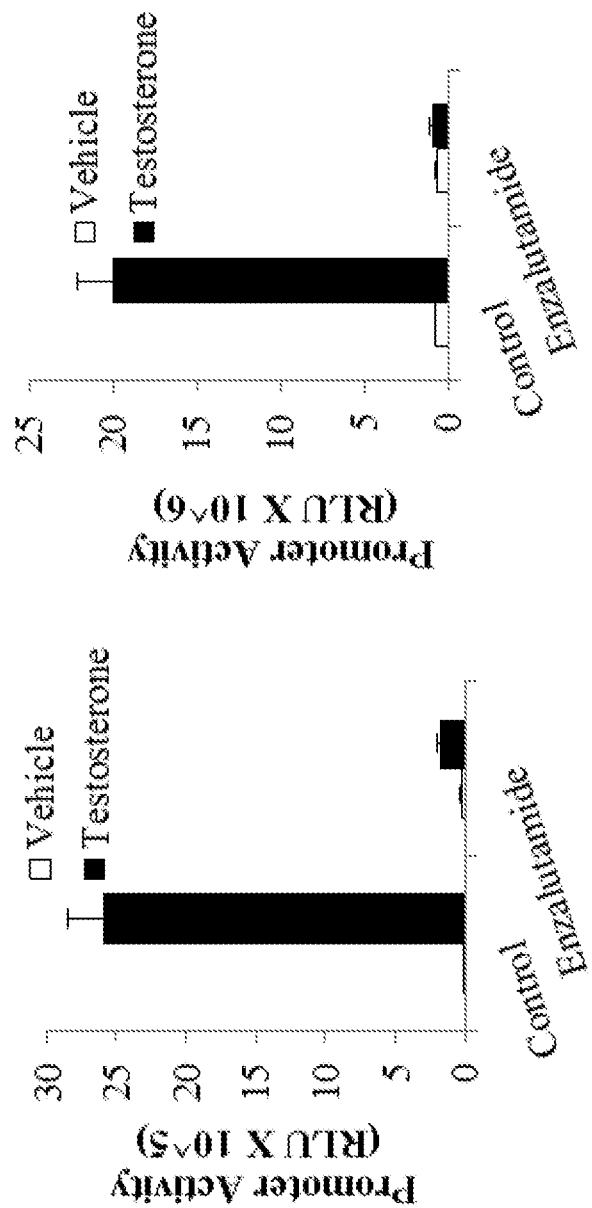
FIG. 7A Primary Screen
FIG. 7B Counter Screen

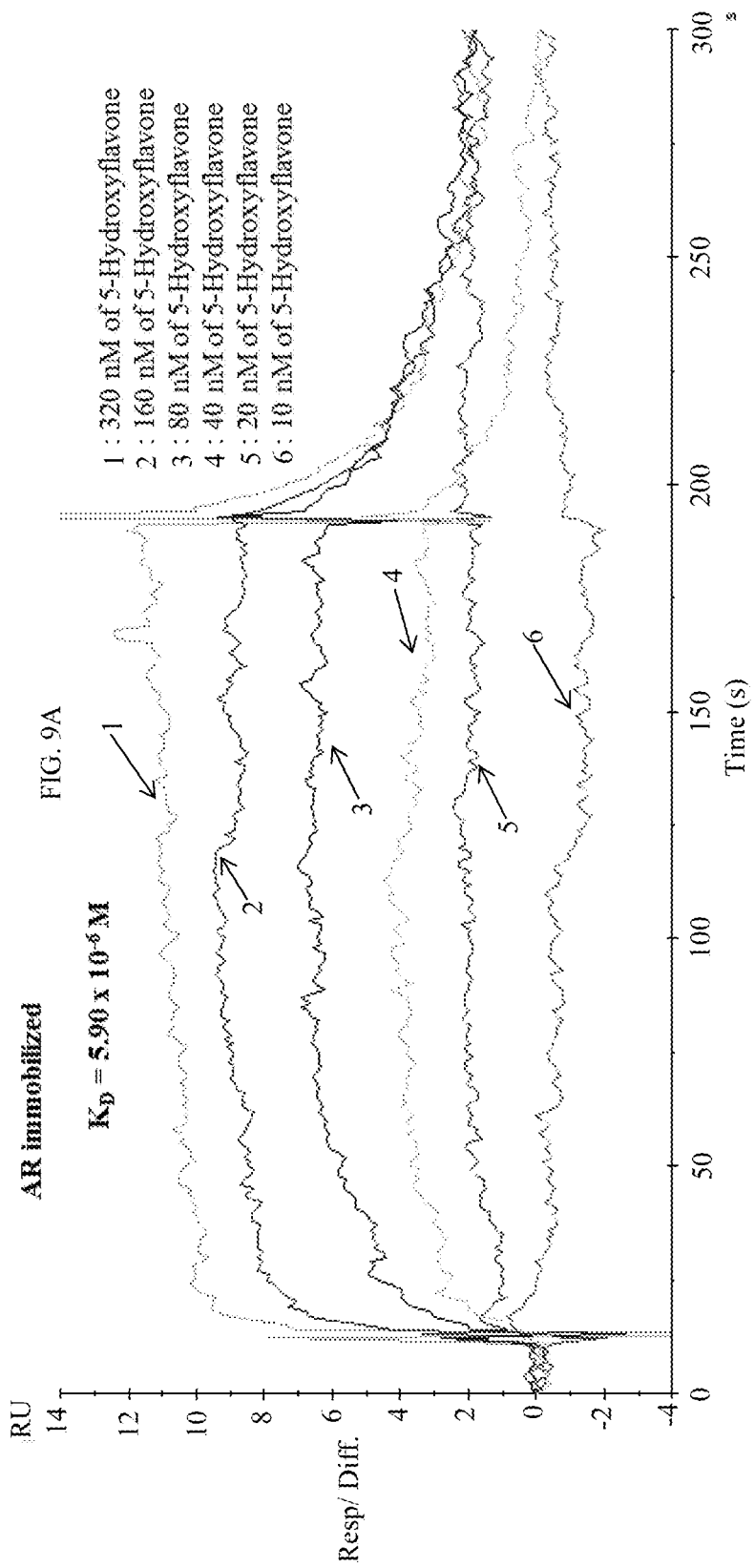

| Structure[a] | Flavonoid | $-R_3$ | $-R_5$ | $-R_6$ | $-R_7$ | $-R_{3'}$ | $-R_{4'}$ | $IC_{50}$ (μM)[b] |
|---|---|---|---|---|---|---|---|---|
| 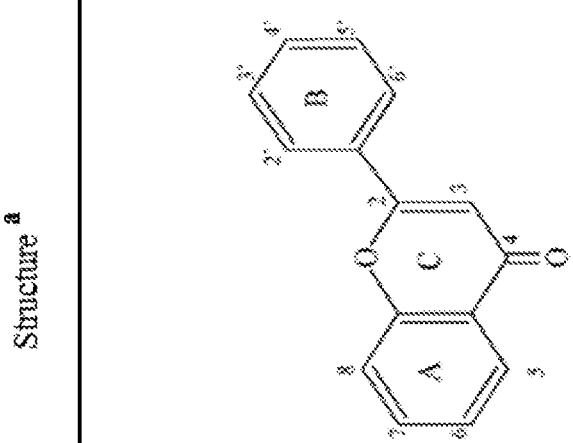 | 5,7,3',4'-Tetrahydroxyflavone | H | OH | H | OH | OH | OH | 1.01 |
| | 5,3',4'-Trihydroxyflavone | H | OH | H | H | OH | OH | 1.01 |
| | 5,7,4'-Trihydroxyflavone | H | OH | H | OH | H | OH | No effect |
| | 7,3',4'-Trihydroxyflavone | H | H | H | OH | OH | OH | No effect |
| | 5,7-Dihydroxyflavone | H | OH | H | OH | H | H | No effect |
| | 3',4'-Dihydroxyflavone | H | H | H | H | OH | OH | No effect |
| | 7,3'-Dihydroxyflavone | H | H | H | OH | OH | H | No effect |
| | 5,4'-Dihydroxyflavone | H | OH | H | H | H | OH | 5.48 |
| | 5,3'-Dihydroxyflavone | H | OH | H | H | OH | H | 0.53 |
| | 7,4'-Dihydroxyflavone | H | H | H | OH | H | OH | No effect |
| | 5-Hydroxyflavone | H | OH | H | H | H | H | >10 |
| | 3'-Hydroxyflavone | H | H | H | H | OH | H | No effect |
| | 5,3'-Dihydroxy-6,7,4'-trimethoxyflavone | H | OH | OCH$_3$ | OCH$_3$ | OH | OCH$_3$ | 4.17 |
| | 5,7,4'-Trihydroxy-3'-methoxyflavone | H | OH | H | OH | OCH$_3$ | OH | No effect |
| | 5,7,3'-Trihydroxy-4'-methoxyflavone | H | OH | H | OH | OH | OCH$_3$ | 1.37 |
| | 5,7,3',4'-Tetrahydroxy-3-methoxyflavone | OCH$_3$ | OH | H | OH | OH | OH | No effect |
| | 5,7,3',4'-Tetramethoxyflavone | H | OCH$_3$ | H | OCH$_3$ | OCH$_3$ | OCH$_3$ | No effect |

FIG. 19

METHODS AND COMPOSITIONS RELATING TO STEROID HORMONE RECEPTOR-DEPENDENT CANCERS

REFERENCE TO RELATED APPLICATION

This application claims priority from U.S. Provisional Patent Application Ser. No. 62/524,879, filed Jun. 26, 2017, the entire content of which is incorporated herein by reference.

FIELD OF THE INVENTION

According to general aspects described herein, compositions and methods are provided relating to steroid hormone receptor-dependent cancers. According to specific aspects, compositions and methods are provided relating to chemical compound structures I, II, III, IV, V, VI, VII, disclosed herein, along with a derivative of any thereof, and/or a pharmaceutically acceptable ester of any thereof, and/or a pharmaceutically acceptable salt of any thereof; and a pharmaceutically acceptable carrier, wherein a pharmaceutically acceptable carrier may be included in the compositions.

BACKGROUND OF THE INVENTION

There is a continuing need for methods and compositions relating to hormone-receptor-dependent cancers, including pharmaceutical compositions including one or more compounds having activity against steroid hormone-receptor-dependent cancer and methods of treatment of a steroid hormone-receptor-dependent cancer in a subject using said pharmaceutical compositions. ELK1 (ETS transcription factor (ELK1), transcript variant 1) is a steroid hormone receptor tethering protein that is implicated in hormone receptor dependent cancers. Compositions and methods according to aspects of the present invention inhibit the association of steroid hormone receptors with ELK1, providing activity against steroid hormone-receptor-dependent cancer.

SUMMARY OF THE INVENTION

Pharmaceutical compositions are provided according to aspects of the present invention which include one or more of: compound I, compound II, compound III, compound IV, compound V, compound VI, compound VII, and/or a derivative of any thereof, and/or a pharmaceutically acceptable ester of any thereof, and/or a pharmaceutically acceptable salt of any thereof; and a pharmaceutically acceptable carrier.

Pharmaceutical compositions are provided according to aspects of the present invention including a compound having structural formula VII:

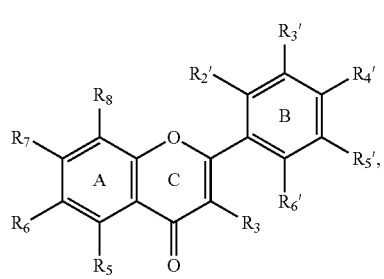

VII where $R_3$, $R_6$, $R_7$, $R_8$, $R_{2'}$, $R_{4'}$, and $R_{6'}$ are each independently selected from: H, alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, an alkoxy group, a fluorinated alkoxy group, a polar group, an ester and a charged group; and $R_5$, $R_{3'}$ and $R_{5'}$ are each independently selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, alkylheterocycloalkyl group, alkylcycloheteroalkyl group, aralkyl group, and heteroaralkyl group, a charged group, a polar group, OH, and F; and/or a pharmaceutically acceptable salt thereof, and/or a pharmaceutically acceptable ester thereof at any of $R_3$, $R_6$, $R_7$, $R_8$, $R_{2'}$, $R_{4'}$, $R_{6'}$, $R_{3'}$, $R_5$ and $R_{5'}$; and a pharmaceutically acceptable carrier. According to aspects, $R_{3'}$ is a pharmaceutically acceptable hydrolysable or pharmaceutically acceptable enzymatically cleavable ester. According to aspects, $R_{2'}$ and $R_{4'}$ are each independently selected from: H, methyl, ethyl, isopropyl, methoxy and trifluoromethoxy (—O—$CF_3$), with the proviso that at least one of $R_{2'}$ and $R_{4'}$ is not H. According to aspects of the present invention, $R_5$ is not methoxy and at least one of $R_{3'}$ and $R_{5'}$ is not methoxy.

Pharmaceutical compositions are provided according to aspects of the present invention including a compound having structural formula VII, where $R_3$, $R_6$, $R_7$, $R_8$, $R_{2'}$, $R_{2'}$, $R_{4'}$, and $R_{6'}$, are each independently selected from: H, alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, an alkoxy group, a fluorinated alkoxy group, a polar group, an ester and a charged group; where $R_{3'}$ is hydroxyl or a pharmaceutically acceptable hydrolysable ester or pharmaceutically acceptable enzymatically cleavable ester, $R_5$ is hydroxyl or a pharmaceutically acceptable hydrolysable ester or pharmaceutically acceptable enzymatically cleavable ester, $R_{5'}$ is selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, alkylheterocycloalkyl group, alkylcycloheteroalkyl group, aralkyl group, heteroaralkyl group, a charged group, a polar group, OH, and F; and/or a pharmaceutically acceptable salt thereof, and/or a pharmaceutically acceptable ester thereof; and a pharmaceutically acceptable carrier. According to aspects, $R_{2'}$ and $R_{4'}$ are each independently selected from: H, methyl, ethyl, isopropyl, methoxy and trifluoromethoxy (—O—$CF_3$), with the proviso that at least one of $R_{2'}$ and $R_{4'}$ is not H. According to aspects of the present invention, $R_{5'}$ is not methoxy.

Pharmaceutical compositions are provided according to aspects of the present invention including a compound having structural formula VII, where $R_3$, $R_6$, $R_7$, $R_8$, $R_{2'}$, $R_{4'}$, and $R_{6'}$ are each independently selected from: H, alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, an alkoxy group, a fluorinated alkoxy group, a polar group, an ester and a charged group; where at least one of $R_{3'}$ and $R_5$, or both, is a pharmaceutically acceptable hydrolysable ester or pharmaceutically acceptable enzymatically cleavable ester; and where $R_{5'}$ is selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, alkylheterocycloalkyl group, alkylcycloheteroalkyl group, aralkyl group, heteroaralkyl group, a charged group, a polar group, OH, and F; and/or a pharmaceutically acceptable salt thereof, and/or a pharmaceutically acceptable ester thereof; and a pharmaceutically acceptable carrier. According to aspects, $R_{2'}$ and $R_{4'}$ are each independently selected from: H, methyl, ethyl, isopropyl, methoxy and trifluoromethoxy (—O—CF$_3$), with the proviso that at least one of $R_{2'}$ and $R_{4'}$ is not H. According to aspects of the present invention, $R_5$ is not methoxy and at least one of $R_{3'}$ and $R_{5'}$ is not methoxy.

Pharmaceutical compositions are provided according to aspects of the present invention including a compound having structural formula VII, where $R_3$, $R_6$, $R_7$, $R_8$, $R_{2'}$, $R_{4'}$, and $R_{6'}$ are each independently selected from: H, alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, an alkoxy group, a fluorinated alkoxy group, a polar group, an ester and a charged group; where $R_{3'}$ is a pharmaceutically acceptable hydrolysable ester or pharmaceutically acceptable enzymatically cleavable ester; and where $R_5$ and $R_{5'}$ are selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, alkylheterocycloalkyl group, alkylcycloheteroalkyl group, aralkyl group, heteroaralkyl group, a charged group, a polar group, OH, and F; and/or a pharmaceutically acceptable salt thereof, and/or a pharmaceutically acceptable ester thereof; and a pharmaceutically acceptable carrier. According to aspects, $R_{2'}$ and $R_{4'}$ are each independently selected from: H, methyl, ethyl isopropyl, methoxy and trifluoromethoxy (—O—CF$_3$), with the proviso that at least one of $R_{2'}$ and $R_{4'}$ is not H. According to aspects of the present invention, $R_5$ is not methoxy and at least one of $R_{3'}$ and $R_{5'}$ is not methoxy.

Pharmaceutical compositions are provided according to aspects of the present invention including a compound having structural formula VII, where $R_3$, $R_6$, $R_7$, $R_8$, and $R_{6'}$ are each independently selected from: H, alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, an alkoxy group, a fluorinated alkoxy group, a polar group, an ester and a charged group; $R_{2'}$ and $R_{4'}$ are each independently selected from: H, methyl, ethyl, isopropyl, methoxy and trifluoromethoxy (—O—CF$_3$), with the proviso that at least one of $R_{2'}$ and $R_{4'}$ is not H; where at least one of $R_{3'}$ and $R_5$, or both, is a pharmaceutically acceptable hydrolysable ester or pharmaceutically acceptable enzymatically cleavable ester, and where $R_{5'}$ is selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, alkylheterocycloalkyl group, alkylcycloheteroalkyl group, aralkyl group, heteroaralkyl group, a charged group, a polar group, OH, and F; and/or a pharmaceutically acceptable salt thereof, and/or a pharmaceutically acceptable carrier. According to aspects of the present invention, $R_5$ is not methoxy and at least one of $R_{3'}$ and $R_{5'}$ is not methoxy.

Pharmaceutical compositions are provided according to aspects of the present invention including a compound having structural formula VII, where $R_{3'}$ is hydroxyl or a pharmaceutically acceptable hydrolysable ester or pharmaceutically acceptable enzymatically cleavable ester, $R_5$ is hydroxyl or a hydrolysable or enzymatically cleavable ester, $R_{5'}$ is H, $R_{2'}$ and $R_{4'}$ are each independently selected from: H, methyl, ethyl, isopropyl, methoxy and trifluoromethoxy (—O—CF$_3$), with the proviso that at least one of $R_{2'}$ and $R_{4'}$ is not H; $R_3$ is H, $R_6$ is H, $R_7$ is H, $R_8$ is H, and $R_{6'}$ is H. According to aspects of the present invention, $R_5$ is not methoxy and $R_{3'}$ is not methoxy.

Pharmaceutical compositions are provided according to aspects of the present invention including a compound having structural formula VII, where $R_{3'}$ is hydroxyl or a pharmaceutically acceptable hydrolysable ester or pharmaceutically acceptable enzymatically cleavable ester, $R_5$ is hydroxyl or a hydrolysable or enzymatically cleavable ester, $R_{5'}$ is H, R4' is methyl, $R_3$ is H, $R_6$ is H, $R_7$ is H, $R_8$ is H, $R_{2'}$ is H, and $R_{6'}$ is H, (5,3'-dihydroxy-4'-methylflavone or a pharmaceutically acceptable ester thereof). According to aspects of the present invention, $R_5$ is not methoxy.

Pharmaceutical compositions are provided according to aspects of the present invention including a compound having structural formula VII, where $R_{3'}$ is hydroxyl or a pharmaceutically acceptable hydrolysable ester or pharmaceutically acceptable enzymatically cleavable ester, $R_5$ is hydroxyl or a hydrolysable or enzymatically cleavable ester, $R_{5'}$ is H, R4' is an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, $R_3$ is H, $R_6$ is H, $R_7$ is H, $R_8$ is H, $R_{2'}$ is H, and $R_{6'}$ is H. According to aspects of the present invention, $R_5$ is not methoxy and $R_{3'}$ is not methoxy.

Pharmaceutical compositions are provided according to aspects of the present invention including a compound having structural formula VII, where $R_{3'}$ is hydroxyl or a pharmaceutically acceptable hydrolysable ester or pharmaceutically acceptable enzymatically cleavable ester, $R_5$ is hydroxyl or a hydrolysable or enzymatically cleavable ester, $R_{2'}$ is H, R4' is H, and $R_{5'}$, $R_3$, $R_6$, $R_7$, $R_8$, and $R_{6'}$ are each independently selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, an alkoxy group, a fluorinated alkoxy group, a polar group, an ester and a charged group.

Pharmaceutical compositions are provided according to aspects of the present invention including a compound having structural formula I (5,3'-dihydroxyflavone), and/or a pharmaceutically acceptable salt thereof, and/or a pharmaceutically acceptable ester thereof.

Pharmaceutical compositions are provided according to aspects of the present invention including a compound having structural formula II (5'-fluoro-5,3'-dihydroxyflavone), and/or a pharmaceutically acceptable salt thereof, and/or a pharmaceutically acceptable ester thereof.

Pharmaceutical compositions are provided according to aspects of the present invention including a compound having structural formula I, II, III, IV, V, VI or VII, and further including an additional therapeutic agent.

Methods of treatment of a hormone receptor-dependent cancer in a subject in need thereof, are provided according to aspects of the present invention which include administering a therapeutically effective dose of a pharmaceutical composition including a compound having structural formula VII:

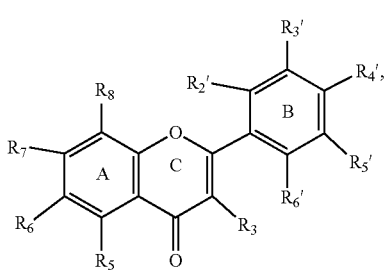

where $R_3$, $R_6$, $R_7$, $R_8$, $R_{2'}$, $R_{4'}$, and $R_{6'}$ are each independently selected from: H, alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, an alkoxy group, a fluorinated alkoxy group, a polar group, an ester and a charged group; and $R_5$, $R_{3'}$ and $R_{5'}$ are each independently selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, alkylheterocycloalkyl group, alkylcycloheteroalkyl group, aralkyl group, and heteroaralkyl group, a charged group, a polar group, OH, and F; and/or a pharmaceutically acceptable salt thereof, and/or a pharmaceutically acceptable ester thereof; and a pharmaceutically acceptable carrier. According to aspects, $R_3$ is a pharmaceutically acceptable hydrolysable ester or pharmaceutically acceptable enzymatically cleavable ester. According to aspects, $R_{2'}$ and $R_{4'}$ are each independently selected from: H, methyl, ethyl, isopropyl, methoxy and trifluoromethoxy (—O—CF$_3$), with the proviso that at least one of $R_{2'}$ and $R_{4'}$ is not H. According to aspects of the present invention, $R_5$ is not methoxy and at least one of $R_{3'}$ and $R_{5'}$ is not methoxy. Methods of treatment of a hormone receptor-dependent cancer in a subject in need thereof, are provided according to aspects of the present invention which further include administration of an additional therapeutic agent or adjunct therapy. According to aspects of the present invention the subject has an androgen receptor-dependent cancer. According to aspects of the present invention the subject has an androgen receptor-dependent prostate cancer. According to aspects of the present invention the subject has an androgen receptor-V7-dependent prostate cancer or other androgen receptor-splice variant-dependent prostate cancer. According to aspects of the present invention the subject has an estrogen receptor-dependent cancer. According to aspects of the present invention the subject has an estrogen receptor-dependent breast cancer. According to aspects of the present invention the subject has the treatment further includes an adjunct anti-cancer treatment. According to aspects of the present invention the subject has the treatment further includes administration of an additional therapeutic agent.

Methods of treatment of a hormone receptor-dependent cancer in a subject in need thereof, are provided according to aspects of the present invention which include administering a therapeutically effective dose of a pharmaceutical composition including a compound having structural formula VII, where $R_3$, $R_6$, $R_7$, $R_8$, $R_{2'}$, $R_{4'}$, and $R_{6'}$ are each independently selected from: H, alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, an alkoxy group, a fluorinated alkoxy group, a polar group, an ester and a charged group; where $R_{3'}$ is hydroxyl or a hydrolysable or enzymatically cleavable ester, $R_5$ is hydroxyl or a hydrolysable or enzymatically cleavable ester, $R_{5'}$ is selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, alkylheterocycloalkyl group, alkylcycloheteroalkyl group, aralkyl group, heteroaralkyl group, a charged group, a polar group, OH, and F; and/or a pharmaceutically acceptable salt thereof, and/or a pharmaceutically acceptable ester thereof; and a pharmaceutically acceptable carrier. According to aspects, $R_{2'}$ and $R_{4'}$ are each independently selected from: H, methyl, ethyl, isopropyl, methoxy and trifluoromethoxy (—O—CF$_3$), with the proviso that at least one of $R_{2'}$ and $R_{4'}$ is not H. According to aspects of the present invention, $R_{5'}$ is not methoxy. Methods of treatment of a hormone receptor-dependent cancer in a subject in need thereof, are provided according to aspects of the present invention which further include administration of an additional therapeutic agent or adjunct therapy. According to aspects of the present invention the subject has an androgen receptor-dependent cancer. According to aspects of the present invention the subject has an androgen receptor-dependent prostate cancer. According to aspects of the present invention the subject has an androgen receptor-V7-dependent prostate cancer or other androgen receptor-splice variant-dependent prostate cancer. According to aspects of the present invention the subject has an estrogen receptor-dependent cancer. According to aspects of the present invention the subject has an estrogen receptor-dependent breast cancer. According to aspects of the present invention the subject has the treatment further includes an adjunct anti-cancer treatment. According to aspects of the present invention the subject has the treatment further includes administration of an additional therapeutic agent.

Methods of treatment of a hormone receptor-dependent cancer in a subject in need thereof, are provided according to aspects of the present invention which include administering a therapeutically effective dose of a pharmaceutical composition including a compound having structural formula VII, where $R_3$, $R_6$, $R_7$, $R_8$, $R_{2'}$, $R_{4'}$, and $R_{6'}$ are each independently selected from: H, alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, an alkoxy group, a fluorinated alkoxy group, a polar group, an ester and a charged group; where at least one of $R_3$, and $R_5$, or both, is a pharmaceutically acceptable hydrolysable ester or pharmaceutically acceptable enzymatically cleavable ester; and where $R_{5'}$ is selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, alkylheterocycloalkyl group, alkylcycloheteroalkyl group, aralkyl group, heteroaralkyl group, a charged group, a polar group, OH, and F; and/or a pharmaceutically acceptable salt thereof, and/or a pharmaceutically acceptable ester thereof; and a pharmaceutically acceptable carrier. According to aspects, $R_{2'}$ and $R_{4'}$ are each independently selected from: H, methyl, ethyl, isopropyl, methoxy and trifluoromethoxy (—O—$CF_3$), with the proviso that at least one of $R_{2'}$ and $R_{4'}$ is not H. According to aspects of the present invention, $R_5$ is not methoxy and at least one of $R_{3'}$ and $R_{5'}$ is not methoxy. Methods of treatment of a hormone receptor-dependent cancer in a subject in need thereof, are provided according to aspects of the present invention which further include administration of an additional therapeutic agent or adjunct therapy. According to aspects of the present invention the subject has an androgen receptor-dependent cancer. According to aspects of the present invention the subject has an androgen receptor-dependent prostate cancer. According to aspects of the present invention the subject has an androgen receptor-V7-dependent prostate cancer or other androgen receptor-splice variant-dependent prostate cancer. According to aspects of the present invention the subject has an estrogen receptor-dependent cancer. According to aspects of the present invention the subject has an estrogen receptor-dependent breast cancer. According to aspects of the present invention the subject has the treatment further includes an adjunct anti-cancer treatment. According to aspects of the present invention the subject has the treatment further includes administration of an additional therapeutic agent.

Methods of treatment of a hormone receptor-dependent cancer in a subject in need thereof, are provided according to aspects of the present invention which include administering a therapeutically effective dose of a pharmaceutical composition including a compound having structural formula VII, where $R_3$, $R_6$, $R_7$, $R_5$, $R_{2'}$, $R_{4'}$ and $R_{6'}$ are each independently selected from: H, alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, an alkoxy group, a fluorinated alkoxy group, a polar group, an ester and a charged group; where $R_3$ is a pharmaceutically acceptable hydrolysable ester or pharmaceutically acceptable enzymatically cleavable ester; and where $R_5$ and $R_{5'}$ are selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, alkylheterocycloalkyl group, alkylcycloheteroalkyl group, aralkyl group, heteroaralkyl group, a charged group, a polar group, OH, and F; and/or a pharmaceutically acceptable salt thereof, and/or a pharmaceutically acceptable ester thereof; and a pharmaceutically acceptable carrier. According to aspects, $R_{2'}$ and $R_{4'}$ are each independently selected from: H, methyl, ethyl, isopropyl, methoxy and trifluoromethoxy (—O—$CF_3$), with the proviso that at least one of $R_{2'}$ and $R_{4'}$ is not H. According to aspects of the present invention, $R_5$ is not methoxy and at least one of $R_{3'}$ and $R_{5'}$ is not methoxy. Methods of treatment of a hormone receptor-dependent cancer in a subject in need thereof, are provided according to aspects of the present invention which further include administration of an additional therapeutic agent or adjunct therapy. According to aspects of the present invention the subject has an androgen receptor-dependent cancer. According to aspects of the present invention the subject has an androgen receptor-dependent prostate cancer. According to aspects of the present invention the subject has an androgen receptor-V7-dependent prostate cancer or other androgen receptor-splice variant-dependent prostate cancer. According to aspects of the present invention the subject has an estrogen receptor-dependent cancer. According to aspects of the present invention the subject has an estrogen receptor-dependent breast cancer. According to aspects of the present invention the subject has the treatment further includes an adjunct anti-cancer treatment. According to aspects of the present invention the subject has the treatment further includes administration of an additional therapeutic agent.

Methods of treatment of a hormone receptor-dependent cancer in a subject in need thereof, are provided according to aspects of the present invention which include administering a therapeutically effective dose of a pharmaceutical composition including a compound having structural formula VII, where $R_3$, $R_6$, $R_7$, $R_8$, and $R_{6'}$ are each independently selected from: H, alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, an alkoxy group, a fluorinated alkoxy group, a polar group, an ester and a charged group; $R_{2'}$ and $R_{4'}$ are each independently selected from: H, methyl, ethyl, isopropyl, methoxy and trifluoromethoxy (—O—$CF_3$), with the proviso that at least one of $R_{2'}$ and $R_{4'}$ is not H; where at least one of $R_3$ and $R_5$, or both, is a pharmaceutically acceptable hydrolysable ester or pharmaceutically acceptable enzymatically cleavable ester, and where $R_{5'}$ is selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, alkylheterocycloalkyl group, alkylcycloheteroalkyl group, aralkyl group, heteroaralkyl group, a charged group, a polar group, OH, and F; and/or a pharmaceutically acceptable salt thereof, and/or a pharmaceutically acceptable ester thereof; and a pharmaceutically acceptable carrier. According to aspects of the present invention, $R_5$ is not methoxy and at least one of $R_{3'}$ and $R_{5'}$ is not methoxy. Methods of treatment of a hormone receptor-dependent cancer in a subject in need thereof, are provided according to aspects of the present invention which further include administration of an additional therapeutic agent or adjunct therapy. According to aspects of the present invention the subject has an androgen receptor-dependent cancer. According to aspects of the present invention the subject has an androgen receptor-dependent prostate cancer. According to aspects of the present invention the subject has an androgen receptor-V7-dependent prostate cancer or other androgen receptor-splice variant-dependent prostate cancer. According to aspects of the present invention the subject has an estrogen receptor-dependent cancer. According to aspects of the present invention the subject has an estrogen receptor-dependent breast cancer. According to aspects of the present invention the subject has the treatment further includes an adjunct anti-cancer treatment. According to aspects of the present invention the subject has the treatment further includes administration of an additional therapeutic agent.

Methods of treatment of a hormone receptor-dependent cancer in a subject in need thereof, are provided according to aspects of the present invention which include administering a therapeutically effective dose of a pharmaceutical composition including a compound having structural formula VII, where $R_{3'}$ is hydroxyl or a pharmaceutically acceptable hydrolysable ester or pharmaceutically acceptable enzymatically cleavable ester, $R_5$ is hydroxyl or a pharmaceutically acceptable hydrolysable ester or pharmaceutically acceptable enzymatically cleavable ester, $R_{5'}$ is H, $R_{2'}$ and $R_{4'}$ are each independently selected from: H, methyl, ethyl, isopropyl, methoxy and trifluoromethoxy (—O—$CF_3$), with the proviso that at least one of $R_{2'}$ and $R_{4'}$ is not H; $R_3$ is H, $R_6$ is H, $R_7$ is H, $R_8$ is H, and $R_{6'}$ is H. According to aspects of the present invention. $R_5$ is not methoxy and $R_{3'}$ is not methoxy. Methods of treatment of a hormone receptor-dependent cancer in a subject in need thereof, are provided according to aspects of the present invention which further include administration of an additional therapeutic agent or adjunct therapy. According to aspects of the present invention the subject has an androgen receptor-dependent cancer. According to aspects of the present invention the subject has an androgen receptor-dependent prostate cancer. According to aspects of the present invention the subject has an androgen receptor-V7-dependent prostate cancer or other androgen receptor-splice variant-dependent prostate cancer. According to aspects of the present invention the subject has an estrogen receptor-dependent cancer. According to aspects of the present invention the subject has an estrogen receptor-dependent breast cancer. According to aspects of the present invention the subject has the treatment further includes an adjunct anti-cancer treatment. According to aspects of the present invention the subject has the treatment further includes administration of an additional therapeutic agent.

Methods of treatment of a hormone receptor-dependent cancer in a subject in need thereof, are provided according to aspects of the present invention which include administering a therapeutically effective dose of a pharmaceutical composition including a compound having structural formula VII, where $R_{3'}$ is hydroxyl or a pharmaceutically acceptable hydrolysable ester or pharmaceutically acceptable enzymatically cleavable ester, $R_5$ is hydroxyl or a pharmaceutically acceptable hydrolysable ester or pharmaceutically acceptable enzymatically cleavable ester, $R_{5'}$ is H, R4' is methyl, $R_3$ is H, $R_6$ is H, $R_7$ is H, $R_8$ is H, $R_{2'}$ is H, and $R_{6'}$ is H, (5,3'-dihydroxy-4'-methylflavone or a pharmaceutically acceptable ester thereof). According to aspects of the present invention, $R_5$ is not methoxy. Methods of treatment of a hormone receptor-dependent cancer in a subject in need thereof, are provided according to aspects of the present invention which further include administration of an additional therapeutic agent or adjunct therapy. According to aspects of the present invention the subject has an androgen receptor-dependent cancer. According to aspects of the present invention the subject has an androgen receptor-dependent prostate cancer. According to aspects of the present invention the subject has an androgen receptor-V7-dependent prostate cancer or other androgen receptor-splice variant-dependent prostate cancer. According to aspects of the present invention the subject has an estrogen receptor-dependent cancer. According to aspects of the present invention the subject has an estrogen receptor-dependent breast cancer. According to aspects of the present invention the subject has the treatment further includes an adjunct anti-cancer treatment. According to aspects of the present invention the subject has the treatment further includes administration of an additional therapeutic agent.

Methods of treatment of a hormone receptor-dependent cancer in a subject in need thereof, are provided according to aspects of the present invention which include administering a therapeutically effective dose of a pharmaceutical composition including a compound having structural formula VII, where $R_{3'}$ is hydroxyl or a hydrolysable or enzymatically cleavable ester, $R_5$ is hydroxyl or a pharmaceutically acceptable hydrolysable ester or pharmaceutically acceptable enzymatically cleavable ester, $R_{5'}$ is H, R4' is an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, $R_3$ is H, $R_6$ is H, $R_7$ is H, $R_8$ is H, $R_{2'}$ is H, and $R_{6'}$ is H. According to aspects of the present invention, $R_5$ is not methoxy and $R_{3'}$ is not methoxy. Methods of treatment of a hormone receptor-dependent cancer in a subject in need thereof, are provided according to aspects of the present invention which further include administration of an additional therapeutic agent or adjunct therapy. According to aspects of the present invention the subject has an androgen receptor-dependent cancer. According to aspects of the present invention the subject has an androgen receptor-dependent prostate cancer. According to aspects of the present invention the subject has an androgen receptor-V7-dependent prostate cancer or other androgen receptor-splice variant-dependent prostate cancer. According to aspects of the present invention the subject has an estrogen receptor-dependent cancer. According to aspects of the present invention the subject has an estrogen receptor-dependent breast cancer. According to aspects of the present invention the subject has the treatment further includes an adjunct anti-cancer treatment. According to aspects of the present invention the subject has the treatment further includes administration of an additional therapeutic agent.

Methods of treatment of a hormone receptor-dependent cancer in a subject in need thereof, are provided according to aspects of the present invention which include administering a therapeutically effective dose of a pharmaceutical composition including a compound having structural formula I (5,3'-dihydroxyflavone), and/or a pharmaceutically acceptable salt thereof, and/or a pharmaceutically acceptable ester thereof. Methods of treatment of a hormone receptor-dependent cancer in a subject in need thereof, are provided according to aspects of the present invention which further include administration of an additional therapeutic agent or adjunct therapy. According to aspects of the present invention the subject has an androgen receptor-dependent cancer. According to aspects of the present invention the subject has an androgen receptor-dependent prostate cancer. According to aspects of the present invention the subject has an androgen receptor-V7-dependent prostate cancer or other androgen receptor-splice variant-dependent prostate cancer. According to aspects of the present invention the subject has an estrogen receptor-dependent cancer. According to aspects of the present invention the subject has an estrogen receptor-dependent breast cancer. According to aspects of the present invention the subject has the treatment further includes an adjunct anti-cancer treatment. According to aspects of the present invention the subject has the treatment further includes administration of an additional therapeutic agent.

Methods of treatment of a hormone receptor-dependent cancer in a subject in need thereof, are provided according to aspects of the present invention which include administering a therapeutically effective dose of a pharmaceutical composition including a compound having structural formula II (5'-fluoro-5,3'-dihydroxyflavone), and/or a pharmaceutically acceptable salt thereof, and/or a pharmaceutically acceptable ester thereof. Methods of treatment of a hormone receptor-dependent cancer in a subject in need thereof, are provided according to aspects of the present invention which further include administration of an additional therapeutic agent or adjunct therapy. According to aspects of the present invention the subject has an androgen receptor-dependent cancer. According to aspects of the present invention the subject has an androgen receptor-dependent prostate cancer. According to aspects of the present invention the subject has an androgen receptor-V7-dependent prostate cancer or other androgen receptor-splice variant-dependent prostate cancer. According to aspects of the present invention the subject has an estrogen receptor-dependent cancer. According to aspects of the present invention the subject has an estrogen receptor-dependent breast cancer. According to aspects of the present invention the subject has the treatment further includes an adjunct anti-cancer treatment. According to aspects of the present invention the subject has the treatment further includes administration of an additional therapeutic agent.

Methods of treatment of a hormone receptor-dependent cancer in a subject in need thereof, are provided according to aspects of the present invention which include administering a therapeutically effective dose of a pharmaceutical composition including a compound having structural formula I, II, III, IV, V, VI or VII, and further including an additional therapeutic agent.

Methods of treatment of a hormone receptor-dependent cancer in a subject in need thereof, are provided according to aspects of the present invention which further include administration of an additional therapeutic agent or adjunct therapy. According to aspects of the present invention the subject has an androgen receptor-dependent cancer. According to aspects of the present invention the subject has an androgen receptor-dependent prostate cancer. According to aspects of the present invention the subject has an androgen receptor-V7-dependent prostate cancer or other androgen receptor-splice variant-dependent prostate cancer. According to aspects of the present invention the subject has an estrogen receptor-dependent cancer. According to aspects of the present invention the subject has an estrogen receptor-dependent breast cancer. According to aspects of the present invention the subject has the treatment further includes an adjunct anti-cancer treatment. According to aspects of the present invention the subject has the treatment further includes administration of an additional therapeutic agent.

Pharmaceutical compositions are provided according to aspects of the present invention which include 5,3'-dihydroxyflavone (compound I; also called KCI807 herein):

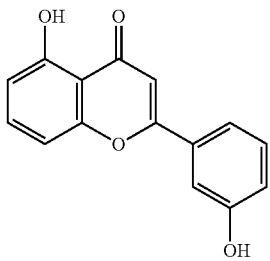 [SMILES: O=c1cc(-c2cccc(O)c2)oc2cccc(O)c12]

and/or a pharmaceutically acceptable salt of any thereof, and/or a derivative of any thereof, and/or a pharmaceutically acceptable ester of any thereof; and a pharmaceutically acceptable carrier.

Pharmaceutical compositions are provided according to aspects of the present invention which include 5'-fluoro-5,3'-dihydroxyflavone (compound II):

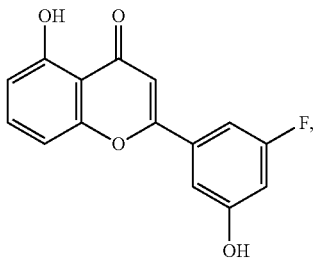 [SMILES: O=c1cc(-c2cc(O)cc(F)c2)oc2cccc(O)c12]

and/or a pharmaceutically acceptable salt of any thereof, and/or a derivative of any thereof, and/or a pharmaceutically acceptable ester of any thereof; and a pharmaceutically acceptable carrier.

Pharmaceutical compositions are provided according to aspects of the present invention which include 3-[2-(1,3-benzodioxol-5-yl)-2-oxoethylidene]-5-bromoindolin-2-one (compound III):

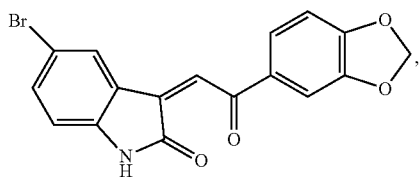 [SMILES: O=C1Nc2ccc(Br)cc2/C1=C/C(=O)c1ccc2c(c1)OCO2]

and/or a pharmaceutically acceptable salt of any thereof, and/or a derivative of any thereof, and/or a pharmaceutically acceptable ester of any thereof; and a pharmaceutically acceptable carrier.

Pharmaceutical compositions are provided according to aspects of the present invention which include 1-acetyl-3-[2-benzyloxy)phenyl]-5-(4-methoxyphenyl)-4,5-dihydro-1H-pyrazol-4-yl acetate (compound IV)

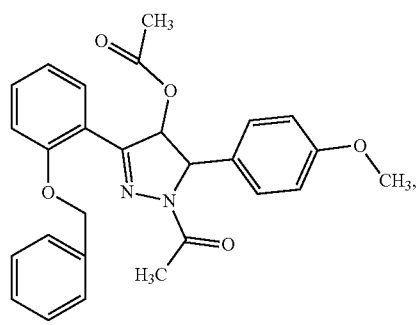 [SMILES: COc1ccc(C2C(OC(C)=O)C(c3ccccc3OCc3ccccc3)=NN2C(C)=O)cc1]

and/or a pharmaceutically acceptable salt of any thereof, and/or a derivative of any thereof, and/or a pharmaceutically acceptable ester of any thereof; and a pharmaceutically acceptable carrier.

Pharmaceutical compositions are provided according to aspects of the present invention which include [4-(4-chlorophenyl)-4,5,6,7-terahydothieno[3,2-c]pyridine-5-yl](4-methoxyphenyl)methanone (compound V)

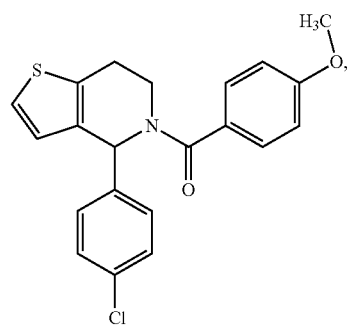 [SMILES: COc1ccc(C(=O)N2CCc3sccc3C2c2ccc(Cl)cc2)cc1]

and/or a pharmaceutically acceptable salt of any thereof, and/or a derivative of any thereof, and/or a pharmaceutically acceptable ester of any thereof; and a pharmaceutically acceptable carrier.

Pharmaceutical compositions are provided according to aspects of the present invention which include 2-(3,5-dimethyl-1-phenyl-1H-pyrazol-4-yl)-5-methoxybenzoic acid (compound VI):

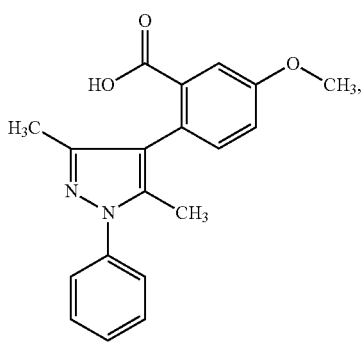 [SMILES: COc1ccc(-c2c(C)nn(-c3ccccc3)c2C)c(C(=O)O)c1]

and/or a pharmaceutically acceptable salt of any thereof, and/or a derivative of any thereof, and/or a pharmaceutically acceptable ester of any thereof; and a pharmaceutically acceptable carrier.

Pharmaceutical compositions are provided according to aspects of the present invention which include a compound having structural formula VII

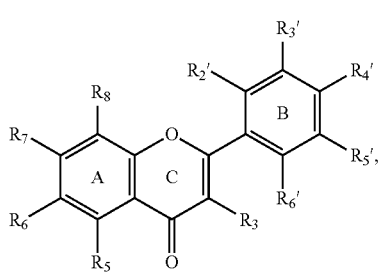

VII where $R_3$, $R_6$, $R_7$, $R_8$, $R_{2'}$, $R_{4'}$, and $R_{6'}$ are each independently selected from: H, a hydrophobic alkyl group with one to 20 carbon atoms, such as one to six carbon atoms, such as methyl, ethyl, isopropyl, such as alkoxy, such as trimethyloxy, such as methoxy and ethoxy groups, a hydrophobic aryl group such as a phenoxy group, a polar group, an ester and a charged moiety containing an amino group(s) or a carboxylic acid group(s); and where $R_5$, $R_{3'}$ and $R_{5'}$ are each independently selected from: H, moiety containing a hydrophobic alkyl group with one to six carbon atoms such as methoxy and ethoxy groups, a moiety containing a hydrophobic aryl group such as a phenoxy group and a charged moiety containing an amino group(s) or a carboxylic acid group(s), a polar group, OH, and F; and/or a pharmaceutically acceptable salt thereof, and/or a pharmaceutically acceptable ester thereof; and a pharmaceutically acceptable carrier.

Pharmaceutical compositions are provided according to aspects of the present invention which include a compound having structural formula VII:

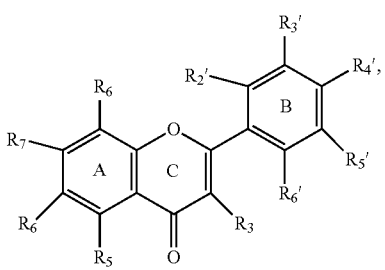

VII where $R_3$, $R_6$, $R_7$, $R_8$, $R_{2'}$, and $R_{6'}$ are each independently selected from: H, a moiety containing a hydrophobic alkyl group with one to six carbon atoms such as methoxy and ethoxy groups, a moiety containing a hydrophobic aryl group such as a phenoxy group, a polar group, an ester and a charged moiety containing an amino group(s) or a carboxylic acid group(s); and where $R_5$, $R_{3'}$ and $R_{5'}$ are each independently selected from: H, moiety containing a hydrophobic alkyl group with one to six carbon atoms such as methoxy and ethoxy groups, a moiety containing a hydrophobic aryl group such as a phenoxy group and a charged moiety containing an amino group(s) or a carboxylic acid group(s), a polar group, OH, and F; with the proviso that $R_5$ is not methoxy and at least one of $R_{3'}$ and $R_{5'}$ is not methoxy; and/or a pharmaceutically acceptable salt thereof, and/or a pharmaceutically acceptable ester thereof; and a pharmaceutically acceptable carrier. Pharmaceutical compositions are provided according to aspects of the present invention which further include an additional therapeutic agent.

Methods of treatment of a hormone receptor-dependent cancer in a subject in need thereof, are provided according to aspects of the present invention which include administering a therapeutically effective dose of a pharmaceutical composition including one or more of: compound I, compound II, compound III, compound IV, compound V, compound VI, compound VII, and/or a pharmaceutically acceptable salt of any thereof, and/or a derivative of any thereof, and/or a pharmaceutically acceptable ester of any thereof; and a pharmaceutically acceptable carrier, to the subject in need thereof. According to aspects of the present invention, the hormone receptor-dependent cancer is an androgen receptor-dependent cancer. According to aspects of the present invention, the hormone receptor-dependent cancer is an androgen receptor-dependent prostate cancer. According to aspects of the present invention, the hormone receptor-dependent cancer is an androgen receptor-V7-dependent prostate cancer. According to aspects of the present invention, the hormone receptor-dependent cancer is an estrogen receptor-dependent cancer. According to aspects of the present invention, the estrogen receptor-dependent cancer is an estrogen receptor-dependent breast cancer. According to aspects of the present invention, the method of treatment further includes an adjunct anti-cancer treatment. According to aspects of the present invention, the method of treatment further includes administration of an additional therapeutic agent.

Methods of treatment of a hormone receptor-dependent cancer in a subject in need thereof, are provided according to aspects of the present invention which include administering a therapeutically effective dose of a pharmaceutical composition including 5,3'-dihydroxyflavone (compound I; also called KCI807 herein):

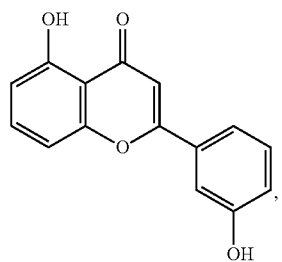 [SMILES: O=c1cc(-c2cccc(O)c2)oc2cccc(O)c12]

and/or a pharmaceutically acceptable salt of any thereof, and/or a derivative of any thereof, and/or a pharmaceutically acceptable ester of any thereof; and a pharmaceutically acceptable carrier, to the subject in need thereof. According to aspects of the present invention, the hormone receptor-dependent cancer is an androgen receptor-dependent cancer. According to aspects of the present invention, the hormone receptor-dependent cancer is an androgen receptor-dependent prostate cancer. According to aspects of the present invention, the hormone receptor-dependent cancer is an androgen receptor-V7-dependent prostate cancer. According to aspects of the present invention, the hormone receptor-dependent cancer is an estrogen receptor-dependent cancer. According to aspects of the present invention, the estrogen receptor-dependent cancer is an estrogen receptor-dependent breast cancer. According to aspects of the present invention, the method of treatment further includes an adjunct anti-cancer treatment. According to aspects of the present invention, the method of treatment further includes administration of an additional therapeutic agent.

Methods of treatment of a hormone receptor-dependent cancer in a subject in need thereof, are provided according to aspects of the present invention which include administering a therapeutically effective dose of a pharmaceutical composition including 5'-fluoro-5,3'-dihydroxyflavone (compound II):

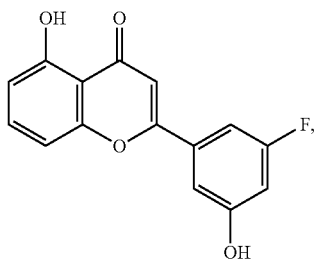 [SMILES: O=c1cc(-c2cc(O)cc(F)c2)oc2cccc(O)c12]

and/or a pharmaceutically acceptable salt of any thereof, and/or a derivative of any thereof, and/or a pharmaceutically acceptable ester of any thereof; and a pharmaceutically acceptable carrier, to the subject in need thereof. According to aspects of the present invention, the hormone receptor-dependent cancer is an androgen receptor-dependent cancer. According to aspects of the present invention, the hormone receptor-dependent cancer is an androgen receptor-dependent prostate cancer. According to aspects of the present invention, the hormone receptor-dependent cancer is an androgen receptor-V7-dependent prostate cancer. According to aspects of the present invention, the hormone receptor-dependent cancer is an estrogen receptor-dependent cancer. According to aspects of the present invention, the estrogen receptor-dependent cancer is an estrogen receptor-dependent breast cancer. According to aspects of the present invention, the method of treatment further includes an adjunct anti-cancer treatment. According to aspects of the present invention, the method of treatment further includes administration of an additional therapeutic agent.

Methods of treatment of a hormone receptor-dependent cancer in a subject in need thereof, are provided according to aspects of the present invention which include administering a therapeutically effective dose of a pharmaceutical composition including 3-[2-(1,3-benzodioxol-5-yl)-2-oxo-ethylidene]-5-bromoindolin-2-one (compound III):

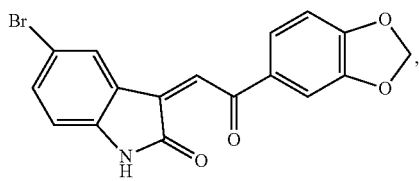 [SMILES: O=C1Nc2ccc(Br)cc2/C1=C/C(=O)c1ccc2c(c1)OCO2]

and/or a pharmaceutically acceptable salt of any thereof, and/or a derivative of any thereof, and/or a pharmaceutically acceptable ester of any thereof; and a pharmaceutically acceptable carrier, to the subject in need thereof. According to aspects of the present invention, the hormone receptor-dependent cancer is an androgen receptor-dependent cancer. According to aspects of the present invention, the hormone receptor-dependent cancer is an androgen receptor-dependent prostate cancer. According to aspects of the present invention, the hormone receptor-dependent cancer is an androgen receptor-V7-dependent prostate cancer. According to aspects of the present invention, the hormone receptor-dependent cancer is an estrogen receptor-dependent cancer. According to aspects of the present invention, the estrogen receptor-dependent cancer is an estrogen receptor-dependent breast cancer. According to aspects of the present invention, the method of treatment further includes an adjunct anti-cancer treatment. According to aspects of the present invention, the method of treatment further includes administration of an additional therapeutic agent.

Methods of treatment of a hormone receptor-dependent cancer in a subject in need thereof, are provided according to aspects of the present invention which include administering a therapeutically effective dose of a pharmaceutical composition including 1-acetyl-3-[2-benzyloxy)phenyl]-5-(4-methoxyphenyl)-4,5-dihydro-1H-pyrazol-4-yl acetate (compound IV):

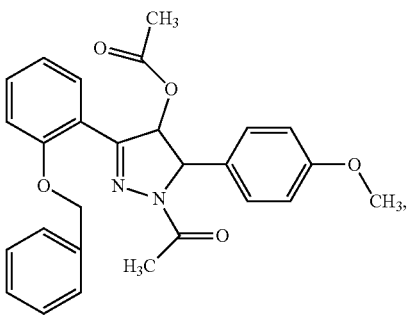 [SMILES: COc1ccc(C2C(OC(C)=O)C(c3ccccc3OCc3ccccc3)=NN2C(C)=O)cc1]

and/or a pharmaceutically acceptable salt of any thereof, and/or a derivative of any thereof, and/or a pharmaceutically acceptable ester of any thereof; and a pharmaceutically acceptable carrier, to the subject in need thereof. According to aspects of the present invention, the hormone receptor-dependent cancer is an androgen receptor-dependent cancer. According to aspects of the present invention, the hormone receptor-dependent cancer is an androgen receptor-dependent prostate cancer. According to aspects of the present invention, the hormone receptor-dependent cancer is an androgen receptor-V7-dependent prostate cancer. According to aspects of the present invention, the hormone receptor-dependent cancer is an estrogen receptor-dependent cancer. According to aspects of the present invention, the estrogen receptor-dependent cancer is an estrogen receptor-dependent breast cancer. According to aspects of the present invention, the method of treatment further includes an adjunct anticancer treatment. According to aspects of the present invention, the method of treatment further includes administration of an additional therapeutic agent.

Methods of treatment of a hormone receptor-dependent cancer in a subject in need thereof, are provided according to aspects of the present invention which include administering a therapeutically effective dose of a pharmaceutical composition including [4-(4-chlorophenyl)-4,5,6,7-terahydothieno[3,2-c]pyridine-5-yl](4-methoxyphenyl)methanone (compound V):

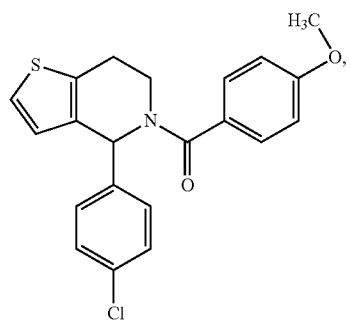 [SMILES: COc1ccc(C(=O)N2CCc3sccc3C2c2ccc(Cl)cc2)cc1]

and/or a pharmaceutically acceptable salt of any thereof, and/or a derivative of any thereof, and/or a pharmaceutically acceptable ester of any thereof; and a pharmaceutically acceptable carrier, to the subject in need thereof. According to aspects of the present invention, the hormone receptor-dependent cancer is an androgen receptor-dependent cancer. According to aspects of the present invention, the hormone receptor-dependent cancer is an androgen receptor-dependent prostate cancer. According to aspects of the present invention, the hormone receptor-dependent cancer is an androgen receptor-V7-dependent prostate cancer. According to aspects of the present invention, the hormone receptor-dependent cancer is an estrogen receptor-dependent cancer. According to aspects of the present invention, the estrogen receptor-dependent cancer is an estrogen receptor-dependent breast cancer. According to aspects of the present invention, the method of treatment further includes an adjunct anticancer treatment. According to aspects of the present invention, the method of treatment further includes administration of an additional therapeutic agent.

Methods of treatment of a hormone receptor-dependent cancer in a subject in need thereof, are provided according to aspects of the present invention which include administering a therapeutically effective dose of a pharmaceutical composition including 2-(3,5-dimethyl-1-phenyl-1H-pyrazol-4-yl)-5-methoxybenzoic acid (compound VI):

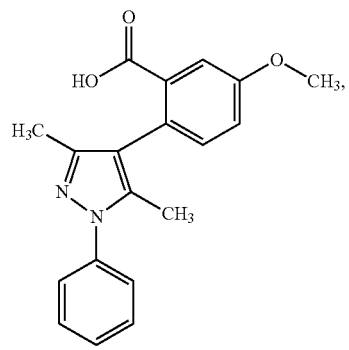 [SMILES: COc1ccc(-c2c(C)nn(-c3ccccc3)c2C)c(C(=O)O)c1]

and/or a pharmaceutically acceptable salt of any thereof, and/or a derivative of any thereof, and/or a pharmaceutically acceptable ester of any thereof; and a pharmaceutically acceptable carrier, to the subject in need thereof. According to aspects of the present invention, the hormone receptor-dependent cancer is an androgen receptor-dependent cancer. According to aspects of the present invention, the hormone receptor-dependent cancer is an androgen receptor-dependent prostate cancer. According to aspects of the present invention, the hormone receptor-dependent cancer is an androgen receptor-V7-dependent prostate cancer. According to aspects of the present invention, the hormone receptor-dependent cancer is an estrogen receptor-dependent cancer. According to aspects of the present invention, the estrogen receptor-dependent cancer is an estrogen receptor-dependent breast cancer. According to aspects of the present invention, the method of treatment further includes an adjunct anticancer treatment. According to aspects of the present invention, the method of treatment further includes administration of an additional therapeutic agent.

Methods of treatment of a hormone receptor-dependent cancer in a subject in need thereof, are provided according to aspects of the present invention which include administering a therapeutically effective dose of a pharmaceutical composition including a compound having structural formula VII:

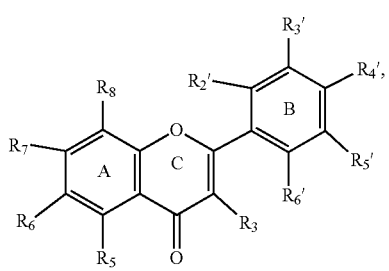

where $R_3$, $R_6$, $R_7$, $R_8$, $R_{2'}$, $R_{4'}$, and $R_{6'}$ are each independently selected from: H, a moiety containing a hydrophobic alkyl group with one to six carbon atoms such as methoxy and ethoxy groups, a moiety containing a hydrophobic aryl group such as a phenoxy group, a polar group, an ester and a charged moiety containing an amino group(s) or a carboxylic acid group(s); and where $R_5$, $R_{3'}$ and $R_{5'}$ are each independently selected from: H, moiety containing a hydrophobic alkyl group with one to six carbon atoms such as methoxy and ethoxy groups, a moiety containing a hydrophobic aryl group such as a phenoxy group and a charged moiety containing an amino group(s) or a carboxylic acid group(s), a polar group, OH, and F; and/or a pharmaceutically acceptable salt thereof, and/or a pharmaceutically acceptable ester thereof; and a pharmaceutically acceptable carrier, to the subject in need thereof. According to aspects of the present invention, the hormone receptor-dependent cancer is an androgen receptor-dependent cancer. According to aspects of the present invention, the hormone receptor-dependent cancer is an androgen receptor-dependent prostate cancer. According to aspects of the present invention, the hormone receptor-dependent cancer is an androgen receptor-V7-dependent prostate cancer. According to aspects of the present invention, the hormone receptor-dependent cancer is an estrogen receptor-dependent cancer. According to aspects of the present invention, the estrogen receptor-dependent cancer is an estrogen receptor-dependent breast cancer. According to aspects of the present invention, the method of treatment further includes an adjunct anti-cancer treatment. According to aspects of the present invention, the method of treatment further includes administration of an additional therapeutic agent.

Methods of treatment of a hormone receptor-dependent cancer in a subject in need thereof, are provided according to aspects of the present invention which include administering a therapeutically effective dose of a pharmaceutical composition including a compound having structural formula VII:

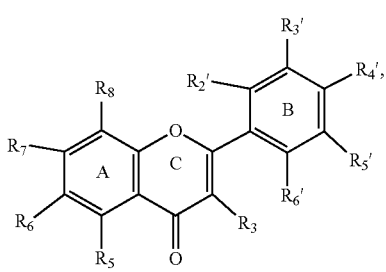

VII where $R_3$, $R_6$, $R_7$, $R_8$, $R_{2'}$, $R_{4'}$, and $R_{6'}$ are each independently selected from: H, a moiety containing a hydrophobic alkyl group with one to six carbon atoms such as methoxy and ethoxy groups, a moiety containing a hydrophobic aryl group such as a phenoxy group, a polar group, an ester and a charged moiety containing an amino group(s) or a carboxylic acid group(s); and where $R_5$, $R_{3'}$ and $R_{5'}$ are each independently selected from: H, moiety containing a hydrophobic alkyl group with one to six carbon atoms such as methoxy and ethoxy groups, a moiety containing a hydrophobic aryl group such as a phenoxy group and a charged moiety containing an amino group(s) or a carboxylic acid group(s), a polar group, OH, and F; with the proviso that $R_5$ is not methoxy and at least one of $R_{3'}$ and $R_{5'}$ is not methoxy; and/or a pharmaceutically acceptable salt thereof, and/or a pharmaceutically acceptable ester thereof; and a pharmaceutically acceptable carrier. Pharmaceutical compositions are provided according to aspects of the present invention which further include an additional therapeutic agent, to the subject in need thereof. According to aspects of the present invention, the hormone receptor-dependent cancer is an androgen receptor-dependent cancer. According to aspects of the present invention, the hormone receptor-dependent cancer is an androgen receptor-dependent prostate cancer. According to aspects of the present invention, the hormone receptor-dependent cancer is an androgen receptor-V7-dependent prostate cancer. According to aspects of the present invention, the hormone receptor-dependent cancer is an estrogen receptor-dependent cancer. According to aspects of the present invention, the estrogen receptor-dependent cancer is an estrogen receptor-dependent breast cancer. According to aspects of the present invention, the method of treatment further includes an adjunct anti-cancer treatment. According to aspects of the present invention, the method of treatment further includes administration of an additional therapeutic agent.

BRIEF DESCRIPTION OF THE DRAWINGS

FIG. 1B shows the chemical structure of 5,7,3',4'-tetrahydroxyisoflavone and a graph showing a dose response curve for 5,7,3',4'-tetrahydroxyisoflavone for inhibition of promoter activation by testosterone in the primary screening assay (ELK1-dependent promoter activation by AR) compared with the counter screening assay (ARE-dependent promoter activation by AR). The cells were simultaneously treated with compound and testosterone for 6h and promoter activity was measured as reporter luciferase activity.

FIG. 2A is a graph showing surface plasmon resonance (SPR) kinetic curves for quantitative analyses of KCI807 binding to AR. AR was immobilized and KCI807 (analyte) was diluted in a series (0, 10, 20, 40, 80, 160, and 320 nM). The calculated $k_{on}$, $k_{off}$ and $k_d$ values are $3.67 \times 10^4$ M$^{-1}$ s$^{-1}$, $2.54 \times 10^{-3}$ s$^{-1}$ and $6.92 \times 10^{-8}$ M respectively.

FIG. 2B is a graph showing SPR kinetic curves for quantitative analysis of inhibition of binding of AR (used as analyte) to immobilized ELK1 by KCI807. A fixed concentration of AR (200 nM) was combined with KCI807 diluted in a series (0, 50, 100, 200, 400, 800, and 1600 nM).

FIG. 2C is a graph showing SPR kinetic curves for quantitative analysis of enzalutamide binding to AR. AR was immobilized and enzalutamide (analyte) was diluted in a series (0, 6.25, 12.5, 25, 50, 100, 200 nM). The calculated $k_{on}$, $k_{off}$ and $k_d$ values are $3.4 \times 105$ M$^{-1}$ s$^{-1}$, $5.8 \times 10^{-4}$ s$^{-1}$ and $1.70 \times 10^{-9}$M respectively.

FIG. 2D is a graph showing SPR kinetic curves to test for inhibition of binding of AR (used as analyte) to immobilized ELK1 by enzalutamide. AR (200 nM) was combined with enzalutamide (0 uM or 1 uM).

FIGS. 2E and 2F are graphs showing results of tests in which LNCaP cells were treated with R1881 (10 nM), R1881 (10 nM)+KCI807 (20 uM), or vehicle for 2h. The cells were fixed and subjected to the chromatin immunoprecipitation (ChIP) assay using antibody to AR. ChIP signals from established sites of AR recruitment by ELK1 (FIG. 2E) or from canonical ARE enhancer sites associated with the KLK3 and TMPRSS2 genes (FIG. 2F) are plotted as percent of input DNA.

FIG. 3A shows results of tests in which 22Rv1 cells were infected with lentivirus expressing shRNA selective for full length AR or ELK1 shRNA or control shRNA. The cell lysates were analyzed by western blot to confirm knockdown of full length AR (top left panel) or ELK1 (top right panel). Real time RT-PCR was used to confirm depletion of mRNA for full length AR (bottom left panel) or ELK1 mRNA (bottom right panel).

FIG. 3B is a graph showing that in the 22Rv1 cells in which full length AR was depleted, the mRNAs for the indicated panel of genes were measured by real time RT-PCR.

FIG. 3C is a graph showing that in In the 22Rv1 cells in which ELK1 was depleted, the mRNAs for the same panel of genes were measured by real time RT-PCR.

FIG. 3D is a graph showing that in 22Rv1 cells were treated with 10 μM of KCI807 for 72h and real time RT-PCR was used to measure mRNAs for the indicated panel of genes tested in FIG. 3B and FIG. 3C.

FIG. 3E is a Venn diagram showing overlaps among genes showing ≥2 fold elevated expression in the control treated 22Rv1 cells compared to cells treated with AR shRNA, ELK1shRNA or KCI807 (10 uM). The p value was based on the hypergeometric test.

FIG. 4A is an image of 22Rv1 cells that were seeded in phenol red-free growth media and treated with the indicated concentration of KCI807, replenishing the treatments every 48h. Colonies were stained with crystal violet 10 days after plating. Treatments were conducted in triplicate. Representative images are shown.

FIG. 4B is a graph showing data from replicate colony formation assays shown in FIG. 4A are plotted as a histogram. Each bar represents the average number of colonies for each triplicate treatment.

FIGS. 4C and 4D are graphs showing the growth inhibitory effects of KCI807 simultaneously compared with the effect of enzalutamide using the MTT assay. Twenty four hours after plating the 22Rv1 cells, they were treated with the indicated concentrations of KCI807 (FIG. 4C) or with the indicated concentrations of enzalutamide (ENZ) (FIG. 4D).

FIGS. 4E and 4F are graphs showing the growth inhibitory effects of KCI807 simultaneously compared with the effect of enzalutamide using the MTT assay. Twenty four hours after plating the LNCaP cells, they were treated with the indicated concentrations of KCI807 (FIG. 4E) or with the indicated concentrations of enzalutamide (ENZ) (FIG. 4F).

FIGS. 4G and 4H are graphs showing the growth inhibitory effects of KCI807 simultaneously compared with the effect of enzalutamide using the MTT assay. Twenty four hours after plating the VCaP cells, they were treated with the indicated concentrations of KCI807 (FIG. 4G) or with the indicated concentrations of enzalutamide (ENZ) (FIG. 4H).

FIG. 5A is a graph showing results obtained when tumor xenografts of 22Rv1 cells were implanted sc into male SCID mice (5 mice per group) in both flanks. Drugs were administered beginning on Day 3 of implantation. The treatments include 250 mg/Kg of KCI807 injected intraperitoneally, on alternate days or vehicle control. In parallel, groups of 5 mice similarly administered KCI807 were sacrificed precisely 6h after the last injection of KCI807 on Day 3, Day 11 and Day 19 for analysis of plasma levels of unmetabolized KCI807 (dashed line, right side vertical axis). For comparison of anti-tumor efficacy, enzalutamide was administered to a separate group of mice following the standard regimen of daily oral administration of 50 mg/Kg. Tumor volume curves and plasma concentration-time profiles are plotted as median and an interval of semi-interquartile range on the basis of their raw values. The p-values were obtained using a linear mixed-effects model after a log-transformation of the raw values. Tumor volumes were monitored as described herein.

FIG. 5B is a graph showing results obtained when PDX-PR011 tumor xenografts were implanted sc into male SCID mice in both flanks. The vehicle control and KCI807 were administered as described for FIG. 5A with the exception that treatment was begun on Day 1 after tumor implantation. Tumor volumes were monitored as described herein.

FIG. 6A is a schematic diagram of the reporter system for the primary screening assay. Recombinant HeLa cells used in this assay harbor the Gal4-TATA-Luc promoter-reporter, and stably express a Gal4-ELK1 fusion protein as well as the androgen receptor (AR). Gal4-ELK1 is bound to the Gal4 elements in the promoter. In the absence of testosterone (small circle), AR is localized in the cytoplasm. When testosterone is present it binds to AR causing AR to translocate to the nucleus where it then binds to Gal4-ELK1 and activates the downstream luciferase reporter.

FIG. 6B is a schematic diagram of the reporter system for the counter screening assay. Recombinant HeLa cells used in this assay are identical to the primary screening cells except for the absence of Gal4-ELK1 and substitution of the Gal4 elements in the promoter with a canonical ARE. In this case, testosterone causes cytosolic AR to translocate to the nucleus and bind to the ARE in the promoter resulting in activation of the luciferase reporter.

FIG. 7A is a graph showing results using recombinant HeLa cells in the primary screen by treatment with either vehicle (ethanol) or 10 nM testosterone together with 10 uM of Enzalutamide or solvent (DMSO) control. Cells were harvested and reporter luciferase activity was measured 24 h post-treatment. In all panels, the error bars represent standard deviation of experimental triplicates. *P<0.001

FIG. 7B is a graph showing results using recombinant HeLa cells in the counter screen by treatment with either vehicle (ethanol) or 10 nM testosterone together with 10 uM of Enzalutamide or solvent (DMSO) control. Cells were harvested and reporter luciferase activity was measured 24 h post-treatment. In all panels, the error bars represent standard deviation of experimental triplicates. *P<0.001

FIG. 9A shows surface plasmon resonance (SPR) kinetic curves for quantitative analyses of compounds binding to AR. AR was immobilized and the 5-Hydroxyflavone (analyte) was diluted in a series (0, 10, 20, 40, 80, 1600, and 320 nM).

FIG. 19 is a table (Table 1) showing structure-activity analysis using derivatives of "Hit1" (5,7,3',4'-tetrahydroxyflavone)[a] $R_8$, $R_{2'}$, $R_{5'}$ and $R_{6'}$ are H in all cases [b] $IC_{50}$ for inhibition of ELK1-dependent promoter activation by AR. The primary screening assay (ELK1-dependent promoter activation by AR) was used to determine the IC50 values for Hit1 and its various derivatives, using a compound dose range of 0.1-10 µM.

DETAILED DESCRIPTION OF THE INVENTION

Figure 1A:
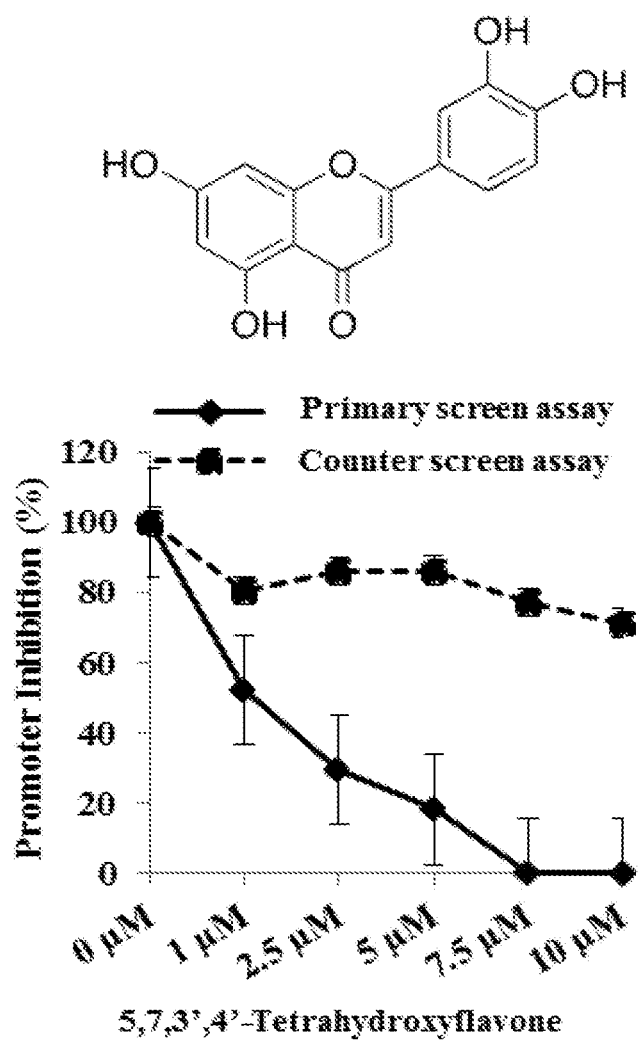
FIG. 1A shows the chemical structure of 5,7,3',4'-tetrahydroxyflavone ("hit 1") and a graph showing a dose response curve for 5,7,3',4'-tetrahydroxyflavone for inhibition of promoter activation by testosterone in the primary screening assay (ELK1-dependent promoter activation by AR) compared with the counter screening assay (ARE-dependent promoter activation by AR). The cells were simultaneously treated with compound and testosterone for 6h and promoter activity was measured as reporter luciferase activity.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Engelke, D. R., RNA Interference (RNAi): Nuts and Bolts of RNAi Technology, DNA Press LLC, Eagleville, P A, 2003; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 9780470151808; Chu, E. and Devita, V. T., Eds., Physicians' Cancer Chemotherapy Drug Manual, Jones & Bartlett Publishers, 2005; J. M. Kirkwood et al., Eds., Current Cancer Therapeutics, 4th Ed., Current Medicine Group, 2001; Remington: The Science and Practice of Pharmacy, Lippincott Williams & Wilkins, 21st Ed., 2005; L. V. Allen, Jr. et al., Ansel's Pharmaceutical Dosage Forms and Drug Delivery Systems, 8th Ed., Philadelphia, Pa.: Lippincott, Williams & Wilkins, 2004; and L. Brunton et al., Goodman & Gilman's The Pharmacological Basis of Therapeutics, McGraw-Hill Professional, 12th Ed., 2011.

The singular terms "a," "an," and "the" are not intended to be limiting and include plural referents unless explicitly stated otherwise or the context clearly indicates otherwise.

The term "nucleic acid" refers to RNA or DNA molecules having more than one nucleotide in any form including single-stranded, double-stranded, oligonucleotide, or polynucleotide. The term "nucleotide sequence" refers to the ordering of nucleotides in a nucleic acid.

Pharmaceutical compositions and methods of treatment

Cancers treated using methods and compositions described herein are characterized by abnormal cell proliferation and are hormone-receptor-dependent, including, but not limited to, pre-neoplastic hyperproliferation, cancer in-situ, neoplasms and metastases.

The term "hormone-sensitive cancer" as used herein refers to a cancer that is dependent on a steroid hormone for growth and/or survival. The term "hormone-receptor-dependent cancer" as used herein includes steroid hormone-sensitive cancer as well as cancers that depend on a steroid receptor for a steroid hormone acting independent of the steroid hormone or that depend on variant forms of the steroid hormone receptor that cannot bind steroid hormone. The terms "hormone-sensitive cancer" and "hormone-receptor-dependent cancer" include, but are not limited to, estrogen-sensitive cancers or otherwise estrogen receptor-dependent cancers and androgen-sensitive cancers or otherwise androgen receptor-dependent cancers. Non-limiting examples of hormone sensitive cancers and otherwise hormone-receptor-dependent cancers include testosterone-sensitive prostate cancer and testosterone-independent but androgen receptor-dependent prostate cancer including castration resistant prostate cancer (CRPC). Further examples include estrogen-sensitive breast cancer and estrogen-independent but estrogen receptor-dependent breast cancer.

Pharmaceutical compositions for use in treating a hormone-receptor-dependent cancer are provided which include one or more anti-hormone-receptor-dependent cancer compounds selected from: 5,3'-dihydroxyflavone (compound I; also called KCI807 herein); 5'-fluoro-5,3'-dihydroxyflavone (compound II); 3[2-(1,3-benzodioxol-5-yl)-2-oxoethylidene]-5-bromoindolin-2-one (compound III); 1-acetyl-3-[2-benzyloxy)phenyl]-5-(4-methoxyphenyl)-4,5-dihydro-1H-pyrazol-4-yl acetate (compound IV); [4-(4-chlorophenyl)-4,5,6,7-terahydothieno[3,2-c]pyridine-5-yl](4-methoxyphenyl)m ethanone (compound V); and 2-(3,5-dimethyl-1-phenyl-1H-pyrazol-4-yl)-5-methoxybenzoic acid (compound VI).

5,3'-dihydroxyflavone (compound I; also called KCI807 herein):

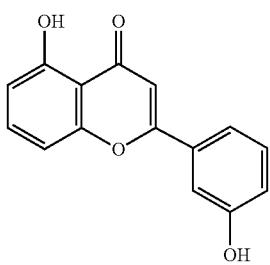 [SMILES: O=c1cc(-c2cccc(O)c2)oc2cccc(O)c12]

5'-fluoro-5,3'-dihydroxyflavone (compound II)

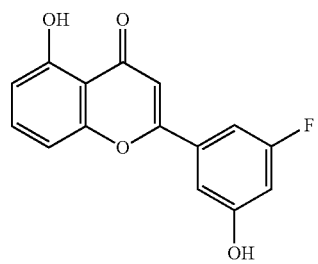 [SMILES: O=c1cc(-c2cc(O)cc(F)c2)oc2cccc(O)c12]

3-[2-(1,3-Benzodioxol-5-Yl)-2-Oxoethylidene]-5-Bromoindolin-2-One (Compound III)

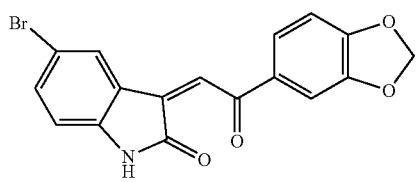 [SMILES: O=C1Nc2ccc(Br)cc2/C1=C/C(=O)c1ccc2c(c1)OCO2]

1-Acetyl-3-[2-Benzyloxy)Phenyl]-5-(4-Methoxyphenyl)-4,5-Dihydro-1H-Pyrazol-4-Yl Acetate (Compound IV)

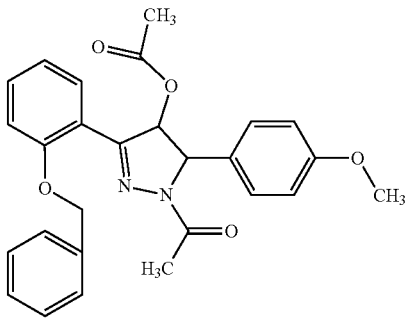 [SMILES: COc1ccc(C2C(OC(C)=O)C(c3ccccc3OCc3ccccc3)=NN2C(C)=O)cc1]

[4-(4-Chlorophenyl)-4,5,6,7-Terahydothieno[3,2-c] Pyridine-5-Yl](4-Methoxyphenyl)Methanone (Compound V)

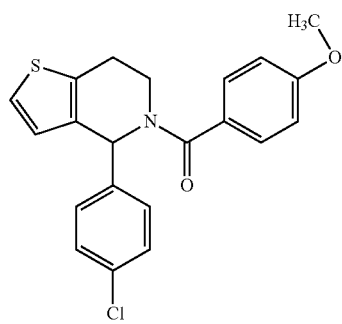 [SMILES: COc1ccc(C(=O)N2CCc3sccc3C2c2ccc(Cl)cc2)cc1]

2-(3,5-Dimethyl-1-Phenyl-1H-Pyrazol-4-Yl)-5-Methoxybenzoic Acid (Compound VI)

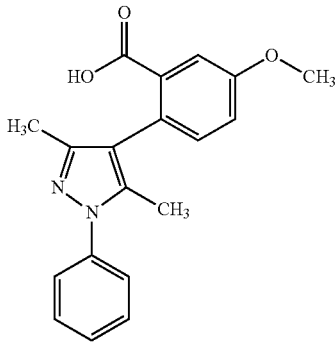

Pharmaceutical compositions of compounds I, II, III, IV, V, VI and VII can be provided as pharmaceutically acceptable salts and/or pharmaceutically acceptable esters and/or derivatives of any of compounds I, II, III, IV, V, VI and WI having anti-hormone-receptor-dependent cancer activity.

As used herein, the term "derivative" is used to refer to a compound whose structure is sufficiently similar to those disclosed herein such that, based upon that similarity, it would be expected, by one skilled in the art, to exhibit the same or similar activities and utilities as the disclosed compounds.

Based on structure-activity studies in Table 1, see FIG. 19, further chemical group substitutions may be made in Compound I (KCI807) to enhance the pharmaceutical properties of the drug. Compound VII below illustrates derivatives of Compound I included in pharmaceutical compositions for use in treating a hormone-receptor-dependent cancer.

VII

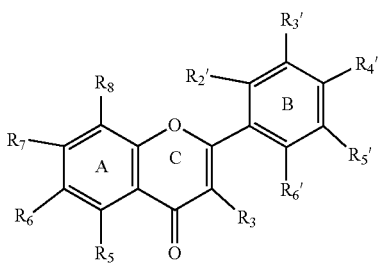

According to aspects of the present invention, in structure VII, $R_5$, $R_{3'}$ and $R_{5'}$ are each independently selected from: H, acyl, OH and F. According to aspects of the present invention, $R_5$ and $R_3$ or $R_{5'}$ are each independently selected from: H, acyl, OH and F. Optionally, one or both of $R_5$ and $R_3$ or $R_{5'}$ in structure VII is F.

In structure VII, optionally, one or both of $R_5$ and $R_3$ or $R_{5'}$ is a pharmaceutically acceptable ester group.

In structure VII, $R_3$, $R_5$, $R_6$, $R_7$, $R_8$, Rr, $R_{3'}$, $R_{4'}$, $R_{5'}$ and $R_{6'}$ are each independently selected from: a hydrogen, a moiety containing a hydrophobic alkyl group with one to six carbon atoms such as methoxy and ethoxy groups, a moiety containing a hydrophobic aryl group such as a phenoxy group, a polar group, an ester and a charged moiety containing an amino group(s) or a carboxylic acid group(s).

According to aspects of the present invention, pharmaceutical compositions having structural formula VII are provided, where $R_3$, $R_5$, $R_6$, $R_7$, $R_8$, $R_{2'}$, $R_{3'}$, $R_{4'}$, $R_{5'}$ and $R_{6'}$ are each independently selected from: a hydrogen, a moiety containing a hydrophobic alkyl group with one to six carbon atoms such as methoxy and ethoxy groups, a moiety containing a hydrophobic aryl group such as a phenoxy group, a polar group, an ester and a charged moiety containing an amino group(s) or a carboxylic acid group(s) with the proviso that $R_5$ is not methoxy and at least one of $R_{3'}$ and $R_{5'}$ is not methoxy.

Pharmaceutical compositions are provided according to aspects of the present invention including a compound having structural formula VII:

VII

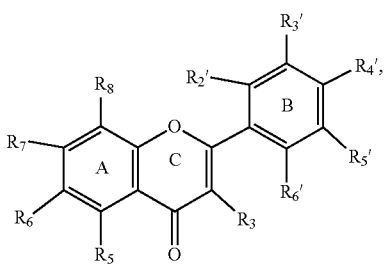

where $R_3$, $R_6$, $R_7$, $R_8$, $R_{2'}$, $R_{4'}$, and $R_{6'}$ are each independently selected from: H, alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, an alkoxy group, a fluorinated alkoxy group, a polar group, an ester and a charged group; and $R_5$, $R_3$ and $R_{5'}$ are each independently selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, alkylheterocycloalkyl group, alkylcyclohetroalkyl group, aralkyl group, and heteroaralkyl group, a charged group, a polar group, OH, and F; and/or a pharmaceutically acceptable salt thereof, and/or a pharmaceutically acceptable ester thereof; and a pharmaceutically acceptable carrier. According to aspects, $R_3$ is a hydrolysable or enzymatically cleavable ester. According to aspects, $R_{2'}$ and $R_{4'}$ are each independently selected from: H, methyl, ethyl, isopropyl, methoxy and trifluoromethoxy ($-O-CF_3$), with the proviso that at least one of $R_{2'}$ and $R_{4'}$ is not H. According to aspects of the present invention, $R_5$ is not methoxy and at least one of $R_{3'}$ and $R_{5'}$ is not methoxy.

Pharmaceutical compositions are provided according to aspects of the present invention including a compound having structural formula VII, where $R_3$, $R_6$, $R_7$, $R_8$, $R_{2'}$, $R_{4'}$, and $R_{6'}$ are each independently selected from: H, alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, an alkoxy group, a fluorinated alkoxy group, a polar group, an ester and a charged group; where $R_3$ is hydroxyl or a hydrolysable or enzymatically cleavable ester, $R_5$ is hydroxyl or a hydrolysable or enzymatically cleavable ester, $R_{5'}$ is selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, alkylheterocycloalkyl group, alkylcycloheteroalkyl group, aralkyl group, heteroaralkyl group, a charged group, a polar group, OH, and F; and/or a pharmaceutically acceptable salt thereof, and/or a pharmaceutically acceptable ester thereof; and a pharmaceutically acceptable carrier. According to aspects, $R_{2'}$ and $R_{4'}$ are each independently selected from: H, methyl, ethyl, isopropyl, methoxy and trifluoromethoxy (—O—$CF_3$), with the proviso that at least one of $R_{2'}$ and $R_{4'}$ is not H. According to aspects of the present invention, $R_{5'}$ is not methoxy.

Pharmaceutical compositions are provided according to aspects of the present invention including a compound having structural formula VII, where $R_3$, $R_6$, $R_7$, $R_8$, $R_{2'}$, $R_{4'}$, and $R_{6'}$ are each independently selected from: H, alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, an alkoxy group, a fluorinated alkoxy group, a polar group, an ester and a charged group; where at least one of $R_{3'}$ and $R_5$, or both, is a hydrolysable or enzymatically cleavable ester; and where $R_{5'}$ is selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, alkylheterocycloalkyl group, alkylcycloheteroalkyl group, aralkyl group, heteroaralkyl group, a charged group, a polar group, OH, and F; and/or a pharmaceutically acceptable salt thereof, and/or a pharmaceutically acceptable ester thereof; and a pharmaceutically acceptable carrier. According to aspects, $R_{2'}$ and $R_{4'}$ are each independently selected from: H, methyl, ethyl, isopropyl, methoxy and trifluoromethoxy (—O—$CF_3$), with the proviso that at least one of $R_{2'}$ and $R_{4'}$ is not H. According to aspects of the present invention, $R_5$ is not methoxy and at least one of $R_{3'}$ and $R_{5'}$ is not methoxy.

Pharmaceutical compositions are provided according to aspects of the present invention including a compound having structural formula VII, where $R_3$, $R_6$, $R_7$, $R_8$, $R_{2'}$, $R_{4'}$, and $R_{6'}$ are each independently selected from: H, alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, an alkoxy group, a fluorinated alkoxy group, a polar group, an ester and a charged group; where $R_3$ is a hydrolysable or enzymatically cleavable ester; and where $R_5$ and $R_{5'}$ are selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, alkylheterocycloalkyl group, alkylcycloheteroalkyl group, aralkyl group, heteroaralkyl group, a charged group, a polar group, OH, and F; and/or a pharmaceutically acceptable salt thereof, and/or a pharmaceutically acceptable ester thereof; and a pharmaceutically acceptable carrier. According to aspects, $R_{2'}$ and $R_{4'}$ are each independently selected from: H, methyl, ethyl, isopropyl, methoxy and trifluoromethoxy (—O—$CF_3$), with the proviso that at least one of $R_{2'}$ and $R_{4'}$ is not H. According to aspects of the present invention, $R_5$ is not methoxy and at least one of $R_{3'}$ and $R_{5'}$ is not methoxy.

Pharmaceutical compositions are provided according to aspects of the present invention including a compound having structural formula VII, where $R_3$, $R_6$, $R_7$, $R_8$, and $R_{6'}$ are each independently selected from: H, alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, an alkoxy group, a fluorinated alkoxy group, a polar group, an ester and a charged group; $R_{2'}$ and $R_{4'}$ are each independently selected from: H, methyl, ethyl, isopropyl, methoxy and trifluoromethoxy (—O—$CF_3$), with the proviso that at least one of $R_{2'}$ and $R_{4'}$ is not H; where at least one of $R_{3'}$ and $R_8$, or both, is a hydrolysable or enzymatically cleavable ester, and where $R_{5'}$ is selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, alkylheterocycloalkyl group, alkylcycloheteroalkyl group, aralkyl group, heteroaralkyl group, a charged group, a polar group, OH, and F; and/or a pharmaceutically acceptable salt thereof, and/or a pharmaceutically acceptable ester thereof; and a pharmaceutically acceptable carrier. According to aspects of the present invention, $R_5$ is not methoxy and at least one of $R_{3'}$ and $R_{5'}$ is not methoxy.

Pharmaceutical compositions are provided according to aspects of the present invention including a compound having structural formula VII, where $R_3$ is hydroxyl or a hydrolysable or enzymatically cleavable ester, $R_5$ is hydroxyl or a hydrolysable or enzymatically cleavable ester, $R_{5'}$ is H, $R_{2'}$ and $R_{4'}$ are each independently selected from: H, methyl, ethyl, isopropyl, methoxy and trifluoromethoxy (—O—$CF_3$), with the proviso that at least one of $R_{2'}$ and $R_{4'}$ is not H; $R_3$ is H, $R_6$ is H, $R_7$ is H, $R_8$ is H, and $R_{6'}$ is H. According to aspects of the present invention, $R_5$ is not methoxy and $R_{3'}$ is not methoxy.

Pharmaceutical compositions are provided according to aspects of the present invention including a compound having structural formula VII, where $R_{3'}$ is hydroxyl or a hydrolysable or enzymatically cleavable ester, $R_5$ is hydroxyl or a hydrolysable or enzymatically cleavable ester, $R_{5'}$ is H, $R_{4'}$ is methyl, $R_3$ is H, $R_6$ is H, $R_7$ is H, $R_8$ is H, $R_{2'}$ is H, and $R_{6'}$ is H, (5,3'-dihydroxy-4'-methylflavone or a pharmaceutically acceptable ester thereof). According to aspects of the present invention, $R_5$ is not methoxy.

Pharmaceutical compositions are provided according to aspects of the present invention including a compound having structural formula VII, where $R_{3'}$ is hydroxyl or a hydrolysable or enzymatically cleavable ester, $R_5$ is hydroxyl or a hydrolysable or enzymatically cleavable ester, $R_{5'}$ is H, $R_{4'}$ is an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, $R_3$ is H, $R_6$ is H, $R_7$ is H, $R_8$ is H, $R_{2'}$ is H, and $R_{6'}$ is H. According to aspects of the present invention, $R_5$ is not methoxy and $R_{3'}$ is not methoxy.

Pharmaceutical compositions are provided according to aspects of the present invention including a compound having structural formula VII, where $R_{3'}$ is hydroxyl or a hydrolysable or enzymatically cleavable ester, $R_5$ is hydroxyl or a hydrolysable or enzymatically cleavable ester, $R_{2'}$ is H, $R_{4'}$ is H, and $R_{5'}$, $R_3$, $R_6$, $R_7$, $R_8$, and $R_{6'}$ are each independently selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, an alkoxy group, a fluorinated alkoxy group, a polar group, an ester and a charged group.

Pharmaceutical compositions are provided according to aspects of the present invention including a compound having structural formula I (5,3'-dihydroxyflavone), and/or a pharmaceutically acceptable salt thereof, and/or a pharmaceutically acceptable ester thereof.

Pharmaceutical compositions are provided according to aspects of the present invention including a compound having structural formula II (5'-fluoro-5,3'-dihydroxyflavone), and/or a pharmaceutically acceptable salt thereof, and/or a pharmaceutically acceptable ester thereof.

Pharmaceutical compositions are provided according to aspects of the present invention including a compound having structural formula I, II, III, IV, V, VI or VII, and further including an additional therapeutic agent.

The term "alkyl group" as used herein refers to a straight or branched chain, or cyclic hydrocarbon, having the number of carbon atoms indicated. An included alkyl group can have, but is not limited to, one to 20 carbon atoms. Examples of alkyl groups include, but are not limited to, methyl, ethyl, n-propyl, isopropyl, n-butyl, t-butyl, isobutyl, sec-butyl, n-pentyl, n-hexyl, n-heptyl, n-octyl, and the like. According to aspects, an included alkyl group includes 1 to six carbon atoms (i.e. C1-C6). According to aspects, an included alkyl group includes 1 to three carbon atoms (i.e. C1-C3). According to aspects, an included alkyl group is a methyl group or ethyl group. One or more heteroatoms may be included in an alkyl group, replacing a carbon atom of the carbon backbone of the alkyl group, i.e. a heteroalkyl group.

The term "alkoxy group" as used herein refers to an oxygen atom connected to an alkyl group. An alkoxy group can be attached to the remainder of the molecule through the oxygen atom. Examples of linear alkoxy groups include, but are not limited to, methoxy, ethoxy, propoxy, butoxy, pentyloxy, hexyloxy, and the like. Examples of branched alkoxy groups include, but are not limited to, isopropoxy, sec-butoxy, tert-butoxy, isopentyloxy, isohexyloxy, and the like. Examples of cyclic alkoxy include, but are not limited to, cyclopropyloxy, cyclobutyloxy, cyclopentyloxy, cyclohexyloxy, and the like. An included alkoxy group can have, but is not limited to, one to 20 carbon atoms. According to aspects, an included alkoxy group includes 1 to six carbon atoms (i.e. C1-C6). According to aspects, an included alkoxy group includes 1 to three carbon atoms (i.e. C1-C4). According to aspects, an included alkoxy group is a methoxy group, ethoxy group, methyltrimethoxy group, methyltriethoxy group, propoxy group, isopropoxy group, butoxy group, t-butoxy group, or any two or more thereof. One or more heteroatoms may be included in an alkoxy group, replacing a carbon atom of the carbon backbone of the alkoxy group, i.e. a heteroalkoxy group. According to aspects, an included alkoxy group is a haloalkoxy group. The terms "haloalkoxy" or "haloalkoxyl" as used herein, refer to an alkoxy group, as defined herein, which further includes 1 or more (e.g., 1, 2, 3, or 4) halogen atoms (e.g., fluorine, chlorine, bromine, or iodine), wherein the alkoxy group is substituted with one or more halogen atoms. According to aspects, an included alkoxy group is a fluorinated alkoxy group, such as, but not limited to, trifluoromethoxy ($-O-CF_3$).

The term "aryl" as used herein refers to a polyunsaturated, aromatic, hydrocarbon substituent that includes a single ring or multiple rings, preferably from 1 to 3 rings, wherein the two or more of the multiple rings may be fused and wherein each ring contains 3-7 carbon atoms, preferably wherein each ring contains 5 or 6 carbon atoms. An aryl group can be attached to the remainder of the molecule through a heteroatom, such as N, O, or S, e.g. an aryloxy, such as a phenoxy group. One or more heteroatoms may be included in an aryl group, i.e. a heteroaryl group, wherein one or more of the 3-7 carbon atoms of each ring, independently, is a heteroatom or wherein one or more of the 5-6 carbon atoms of each ring, independently, is a heteroatom. Non-limiting examples of aryl groups are phenyl, biphenyl, naphthyl indacenyl, azulenyl, heptalenyl, fluorenyl, phenanthrenyl, and the like. One or more heteroatoms may be included in a aryl group, replacing a carbon atom of the carbon backbone of the aryl group, i.e. a heteroaryl group. A "heteroaryl" refers to an aryl group that contains one or more heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Aryl groups can be unsubstituted or substituted. Exemplary aryl groups include substituted or unsubstituted phenyl and substituted or unsubstituted naphthyl.

The term "alkenyl" refers to a straight or branched hydrocarbon chain having one or more double bonds. One or more heteroatoms may be included in an alkenyl group, i.e. a heteroalkenyl group.

The terms "cycloalkyl" and "cycloheteroalkyl" refer to cyclic versions of "alkyl" and "heteroalkyl," respectively. A heteroatom of a cycloheteroalkyl group can occupy the position at which the cycloheteroalkyl group is attached to the remainder of structure VII. Examples of cycloalkyl include, but are not limited to, cyclopropyl, cyclobutyl, cyclopentyl, cyclohexyl, 1-cyclohexenyl, 3-cyclohexenyl, cycloheptyl, cyclooctanyl, and the like. Examples of cycloheteroalkyl include, but are not limited to, 1-piperidinyl, 2-piperidinyl, 3-piperidinyl, 1-piperazinyl, 2-piperazinyl, 3-morpholinyl, 4-morpholinyl, tetrahydrofuran-2-yl, tetrahydrofuran-3-yl, tetrahydrothien-2-yl, tetrahydrothien-3-yl, and the like.

The term "alkylcycloalkyl" refers to a monovalent saturated hydrocarbon ring system, typically monocyclic, bicyclic, or tricyclic, linked to an alkyl group. Specific examples of an alkylcycloalkyl group include a cyclopropylmethyl group, a cyclopropylethyl group, and a cyclohexylethyl group. One or more heteroatoms may be included in an alkylcycloalkyl group, replacing a carbon atom of the carbon backbone of the alkylcycloalkyl group, i.e. a alkylheterocycloalkyl or alkylcycloheteroalkyl group.

The term "aralkyl" also known as "arylalkyl" refers to an alkyl group with an aryl substituent. One or more heteroatoms may be included in an aralkyl group, replacing a carbon atom of the carbon backbone of the aralkyl group, i.e. a heteroaralkyl.

The term "alkynyl," as used herein, refers to a straight or branched chain group, typically from 2 to 20 carbon atoms (e.g., from 2 to 4, from 2 to 6, or from 2 to 10 carbons) containing a carbon-carbon triple bond. Alkynyls are exemplified by ethynyl, 1-propynyl, and the like. One or more heteroatoms may be included in an alkynyl group, replacing a carbon atom of the carbon backbone of the alkynyl group, i.e. a heteroalkynyl.

Unless otherwise specified, each instance of an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group is independently optionally substituted with one or more substituents. The term "substituted" means that at least one hydrogen present on an alkyl group, heteroalkyl group, aryl group, and/or heteroaryl group is replaced with a permissible substituent. A permissible substituent is one which upon substitution results in a stable compound which does not spontaneously undergo an undesired transformation such as by rearrangement, cyclization, elimination, or other reaction. Such substituents include, for example, amino, hydroxy, cyano, carboxy, nitro, thio, alkoxy, and halogen, such as fluoro, iodo, bromo, chloro, trihaloalkyl, such as trihalomethyl, trihaloalkoxy, such as trihalomethoxy. Such substituents include, for example, alkyl, alkenyl, alkynyl, aryl, aralkyl, aryloxy, aralkoxy, carboxy, aroyl, alkoxycarbonyl, aryloxycarbonyl, aralkoxycarbonyl, acyloxy, acylamino, aroylamino, carbamoyl, alkylcarbamoyl, dialkylcarbamoyl, arylthio, alkylthio, and alkylene.

The term "polar group" can include uncharged and charged (both positively and negatively) polar groups. Typical examples of such polar groups include, but are not limited to, halogen, amine groups, hydroxyl groups, phosphate groups, phosphonate groups, sulfate groups, sulfhydryl groups, sulfonate groups, e.g. sulfonic acid, sulfonic salts and sulfonic esters, sulfonyl groups such as sulfonamides, carbonyl groups such as carboxylic acids and carboxylic amides, alkylamine groups, alkylammonium groups, and arylammonium groups. A charged group containing an amino group(s) or a carboxylic acid group(s) can be included.

The term "ester" includes compounds or moieties which contain a carbon or a heteroatom bound to an oxygen atom which is bonded to the carbon of a carbonyl group. According to aspects of the present invention, the ester is a valinyl ester (ester of the amino acid valine) of a 3'-hydroxyl and/or of a 5-hydroxyl in structure VII. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting a free base or free acid function with a suitable reagent, as described generally below.

For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Compositions are provided according to aspects of the present invention in prodrug form. The term "prodrug" refers to a pharmaceutical agent that is converted into a therapeutically active agent, typically from a less active form into a corresponding more active form, such as from a less bioavailable form to a more bioavailable form, under physiological conditions, such as in vivo. Such prodrugs may be pharmaceutically acceptable esters of compositions provided according to aspects of the present invention. According to aspects, any one of $R_3$, $R_6$, $R_7$, $R_8$, $R_{2'}$, $R_{4'}$, $R_{6'}$, $R_{3'}$, $R_5$, and $R_{5'}$ of structure VII is modified to include a moiety such that the compound is a prodrug. Pharmaceutically acceptable prodrugs of the compounds of this invention include, without limitation, esters, amino acid esters, phosphate esters, and sulfonate esters. Examples of prodrug forms are described in Sloan, K. B., Prodrugs, M. Dekker, New York, 1992; and Testa, B. and Mayer, J. M., Hydrolysis in drug and prodrug metabolism: chemistry, biochemistry, and enzymology, Wiley-VCH, Zurich, 2003. According to aspects of the present invention, a prodrug includes one or more moieties that are hydrolyzed under physiological conditions, such as in vivo, to produce a desired therapeutically active molecule. According to aspects of the present invention, a prodrug is converted by an enzymatic activity under physiological conditions, such as in vivo. According to aspects, $R_3$ of structure VII is hydroxyl or a hydrolysable or enzymatically cleavable ester and/or $R_8$ of structure VII is hydroxyl or a hydrolysable or enzymatically cleavable ester, The term "pharmaceutically acceptable ester", as used herein, refers to esters that hydrolyze, or are enzymatically cleaved, in vivo and include those that break down readily in the human body to leave the parent compound or a salt thereof. Suitable pharmaceutically acceptable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular pharmaceutically acceptable esters include formates, acetates, propionates, butyrates, acrylates and ethylsuccinates. Pharmaceutically acceptable esters include, in a non-limiting example aliphatic L-amino acid esters such as leucyl, isoleucyl and valyl. According to aspects, any one of $R_3$, $R_6$, $R_7$, $R_8$, $R_{2'}$, $R_{4'}$, $R_{6'}$, $R_{3'}$, $R_5$, and $R_{5'}$ of structure VII is a hydrolysable pharmaceutically acceptable ester or enzymatically cleavable pharmaceutically acceptable ester. According to aspects, any one of $R_3$, $R_6$, $R_7$, $R_8$, $R_{2'}$, $R_{4'}$, $R_{6'}$, $R_{3'}$, $R_5$, and $R_{5'}$ of structure VII is a pharmaceutically acceptable ester selected from: an amino acid ester, phosphate ester, sulfonate ester, an ester derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms, a formate, an acetate, a propionate, a butyrate, an acrylate or an ethylsuccinate. According to aspects, any one of $R_3$, $R_6$, $R_7$, $R_8$, $R_{2'}$, $R_{4'}$, $R_{6'}$, $R_{3'}$, $R_5$, and $R_{5'}$ of structure VII is a pharmaceutically acceptable ester selected from aliphatic L-amino acid esters such as leucyl, isoleucyl and valyl.

Compounds I, II, III, IV, V, VI, VII and pharmaceutically acceptable salts and/or esters thereof can be synthesized using standard chemical synthetic methodology.

Methods of treatment of a subject having, or at risk of having hormone receptor-dependent cancer are provided according to aspects of the present invention which include administering one or more of compounds I, II, III, IV, V, VI, VII and/or one or more pharmaceutically acceptable esters and/or pharmaceutically acceptable salts thereof.

Methods and compositions of the present invention can be used for prophylaxis as well as amelioration of signs and/or symptoms of hormone receptor-dependent cancer. The terms "treating" and "treatment" used to refer to treatment of a hormone receptor-dependent cancer in a subject include: preventing, inhibiting or ameliorating the hormone receptor-dependent cancer in the subject, such as slowing progression of the hormone receptor-dependent cancer and/or reducing or ameliorating a sign or symptom of the hormone receptor-dependent cancer.

A therapeutically effective amount of one or more of compounds I, II, III, IV, V, VI, VII and/or one or more pharmaceutically acceptable esters and/or salts thereof is an amount which has a beneficial effect in a subject being treated. In subjects having hormone receptor-dependent cancer or at risk for having hormone receptor-dependent cancer, such as a condition characterized by abnormal hormone receptor-dependent cell proliferation including, but not limited to, pre-neoplastic hyperproliferation of hormone receptor-dependent cells, hormone receptor-dependent cancer in-situ, hormone receptor-dependent neoplasms, hormone receptor-dependent metastasis, a hormone receptor-dependent tumor, a benign hormone receptor-dependent growth or other hormone receptor-dependent abnormal cell proliferation condition responsive to a composition of the present invention, a therapeutically effective amount of a composition of the present invention is effective to ameliorate or prevent one or more signs and/or symptoms of the hormone receptor-dependent abnormal cell proliferation condition.

A subject treated according to methods and using compositions of the present invention can be mammalian or non-mammalian. A mammalian subject can be any mammal including, but not limited to, a human; a non-human primate; a rodent such as a mouse, rat, or guinea pig; a domesticated pet such as a cat or dog; a horse, cow, pig, sheep, goat, or rabbit. A non-mammalian subject can be any non-mammal including, but not limited to, a bird such as a duck, goose, chicken, or turkey. Subjects can be either gender and can be any age. In aspects of methods including administration of an inventive pharmaceutical composition to a subject, the subject is human. The terms "subject" and "patient" are used interchangeably herein.

Combinations of: 1) one or more of compounds I, II, III, IV, V, VI, VII and/or one or more pharmaceutically acceptable esters and/or salts of any thereof; and 2) one or more additional therapeutic agents are administered according to aspects of the present invention to treat hormone receptor-dependent cancer.

The term "additional therapeutic agent" is used herein to refer to a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues which is a biologically, physiologically, or pharmacologically active substance (or substances) that acts locally or systemically in a subject.

Additional therapeutic agents included according to aspects of methods and compositions of the present invention include, but are not limited to, antibiotics, antivirals, antineoplastic agents, anti-cancer agents, analgesics, antidepressants, antipsychotics, antipyretics, anti histamines, anti-osteoporosis agents, anti-osteonecrosis agents, antiinflammatory agents, anxiolytics, chemotherapeutic agents, diuretics, growth factors, non-steroidal anti-inflammatory agents, and vasoactive agents.

Additional therapeutic agents for treatment of hormone receptor (AR)-dependent prostate cancer, included according to aspects of methods and compositions of the present invention include, but are not limited to, agents for chemical castration of a subject having hormone receptor (AR)-dependent prostate cancer. Agents for chemical castration of a subject having hormone receptor (AR)-dependent prostate cancer include an analog of the luteinizing hormone releasing hormone (LHRH) and/or an androgen antagonist, such as bicalutamide. Castration resistant hormone receptor (AR)-dependent prostate cancer (CRPC) is typically treated with an androgen synthesis inhibitor (abiraterone) and a high affinity androgen antagonist (enzalutamide). Abiraterone and enzalutamide are ineffective against prostate tumors that depend on splice variants of AR which do not bind or require androgen and hence cannot bind, these drugs.

Compositions of the present invention are effective in the spectrum of prostate cancer, including early stage prostate cancer, CRPC and enzalutamide resistant and abiraterone resistant CRPC. Compositions of the present invention are effective against AR splice variants. Compositions of the present invention are or in various combinations with castration, chemical castration, abiraterone and AR antagonists such as bicalutamide and enzalutamide, with or without other anti-cancer drugs mentioned herein.

Hormone receptor-dependent breast cancer is commonly treated using the partial ER antagonist, tamoxifen and less commonly the partial ER antagonist toremifene. In advanced stages a pure ER antagonist (an ER downregulator) such as fulvestrant may be used. In post-menopausal women, it is also commonly treated with an aromatase inhibitor (inhibitor of estrogen synthesis) such as anastrozole or letrozole. Pre-menopausal women may be treated with LHRH agents to suppress estrogen production in the ovary. Additional hormone therapies that are sometimes used, include megestrol (a drug with actions similar to progesterone) or fluoxymesterone, an anabolic steroid that reduces estrogen.

Compositions of the present invention are effective in both early and advanced stage breast cancer, either individually or in various combinations with the hormonal therapies listed above.

Compositions, commercial packages and methods of treatment of hormone receptor (AR)-dependent prostate cancer are provided which include a composition according to the present invention and one or more of: an agent for chemical castration such as an analog of the luteinizing hormone releasing hormone (LHRH) and/or an androgen antagonist, such as bicalutamide; an androgen synthesis inhibitor such as abiraterone; and a high affinity androgen antagonist such as enzalutamide.

Compositions, commercial packages and methods of treatment of hormone receptor-dependent breast cancer are provided which include a composition according to the present invention and one or more of: the partial estrogen receptor (ER) antagonist, tamoxifen and/or the partial ER antagonist toremifene; an ER antagonist; an ER downregulator, such as fulvestrant; an aromatase inhibitor (inhibitor of estrogen synthesis) such as anastrozole or letrozole; an LHRH agent to suppress estrogen production in the ovary; megestrol (a drug with actions similar to progesterone); or fluoxymesterone, an anabolic steroid that reduces estrogen.

According to aspects of the present invention, combination therapies include: (1) administration of a pharmaceutical composition that includes a pharmaceutical combination composition including two or more of: compound I, compound II, compound III, compound IV, compound V, compound VI, compound VII and/or pharmaceutically acceptable esters and/or salts thereof, formulated together in a single pharmaceutical composition; and/or (2) co-administration of two or more of: compound I, compound II, compound III, compound IV, compound V, compound VI, compound VII and/or pharmaceutically acceptable esters and/or salts thereof, wherein the two or more have not been formulated in the same composition. When using separate formulations the two or more compounds and/or pharmaceutically acceptable salts thereof may be administered during a course of treatment at the same time, intermittent times, staggered times, prior to, subsequent to, or combinations thereof.

According to aspects of the present invention, combination therapies include: (1) administration of a pharmaceutical composition that includes a) and b) wherein a) is: at least one of: compound I, compound II, compound III, compound IV, compound V, compound VI, compound VII, and/or pharmaceutically acceptable esters and/or salts thereof; and wherein b) is: a therapeutic agent, wherein a) and b) are formulated together in a single pharmaceutical composition; and/or (2) co-administration of a) and b). When using separate formulations a) and b) may be administered during a course of treatment at the same time, intermittent times, staggered times, prior to, subsequent to, or combinations thereof.

Combination treatments can allow for reduced effective dosage and increased therapeutic index compared to treatment with a single active agent.

The term "course of treatment" refers to a period of time over which a subject is treated for a specified condition. The course of treatment may be a single administration extending minutes, hours, days or months (such as continuous intravenous administration for example) or may include multiple administrations of a pharmaceutical composition with intervening periods between each administration, wherein the intervening period may extend minutes, hours, days or months. In general, a course of treatment extends minutes, hours, days or months, even years, until the desired beneficial effect is achieved, e.g. amelioration of signs or symptoms of hormone receptor-dependent cancer.

An additional therapeutic agent is an anti-cancer agent according to aspects of the present invention.

Anti-cancer agents are described, for example, in Goodman et al., Goodman and Gilman's The Pharmacological Basis of Therapeutics, 8th Ed., Macmillan Publishing Co., 1990.

Anti-cancer agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bevacizumab, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflornithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochloride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin.

According to aspects of the present invention, one or more correlative biomarkers of therapeutic activity of: one or more of: compound I, compound II, compound III, compound IV, compound V, compound VI, compound VII, and/or pharmaceutically acceptable esters and/or salts thereof, formulated together in a single pharmaceutical composition; and/or (2) co-administration of two or more of: compound I, compound II, compound III, compound IV, compound V, compound VI, compound VII, and/or pharmaceutically acceptable esters and/or salts thereof, administered to treat cancer in a subject are assayed to assess treatment of the cancer in the subject. Thus, for example, the inhibition of tumor growth is a correlative biomarker of therapeutic activity of treatment administered as a combination treatment of the present invention to treat cancer in a subject in need thereof. Inhibition of tumor growth is measured according to standard methodologies, for example as described herein.

Optionally, a method of treating cancer in a subject in need thereof further includes an adjunct anti-cancer treatment. An adjunct anti-cancer treatment can be a radiation treatment of a subject or an affected area of a subject's body.

The dosage of any one of compound I, compound II, compound III, compound IV, compound V, compound VI, compound VII, and/or pharmaceutically acceptable esters and/or salts thereof, as well as any optional additional therapeutic agent will vary based on factors such as, but not limited to, the route of administration; the age, health, sex, and weight of the subject to whom the composition is to be administered; the nature and extent of the subject's symptoms, if any, and the effect desired. Dosage may be adjusted depending on whether treatment is to be acute or continuing. One of skill in the art can determine a pharmaceutically effective amount in view of these and other considerations typical in medical practice.

In general it is contemplated that a daily dosage of any one of compound I, compound II, compound III, compound IV, compound V, compound VI, compound VII, and/or pharmaceutically acceptable esters and/or salts thereof, and any optional additional therapeutic agent is in the range of about 0.001 to 250 milligrams per kilogram of a subject's body weight. A daily dose may be administered as two or more divided doses to obtain the desired effect. A pharmaceutical composition including any one or more of: compound I, compound II, compound III, compound IV, compound V, compound VI, compound VII, and/or pharmaceutically acceptable esters and/or salts thereof, and any optional additional therapeutic agent, may also be formulated for sustained release to obtain desired results.

In particular aspects of inventive methods, the amount of the adjunct anti-cancer treatment and/or anti-cancer agent administered is less than an amount of the adjunct anti-cancer treatment and/or anti-cancer agent necessary to achieve a therapeutic effect if administered without one or more of: compound I, compound II, compound III, compound IV, compound V, compound VI, compound VII, and/or pharmaceutically acceptable esters and/or pharmaceutically acceptable salts thereof. Thus, in particular aspects of the present invention, the amount of an anti-cancer treatment and/or agent administered is at least 5%, at least 10%, at least 15%, at least 20%, at least 25%, at least 30%, at least 35%, at least 40%, at least 50%, at least 55%, at least 60%, at least 65%, at least 70%, at least 75%, at least 80%, at least 85%, or at least 90%, less than an amount of the adjunct anti-cancer treatment and/or agent necessary to achieve a therapeutic effect when administered without a combination treatment of the present invention additionally including administration of compound I, compound II, compound III, compound IV, compound V, compound VI, compound VII, and/or pharmaceutically acceptable esters and/or pharmaceutically acceptable salts thereof.

Methods of the present invention include administration of a pharmaceutical composition of the present invention by a route of administration including, but not limited to, oral, rectal, nasal, pulmonary, epidural, ocular, otic, intraarterial, intracardiac, intracerebroventricular, intradermal, intravenous, intramuscular, intraperitoneal, intraosseous, intrathecal, intravesical, subcutaneous, topical, transdermal, and transmucosal, such as by sublingual, buccal, vaginal, and inhalational, routes of administration.

Combination Pharmaceutical Compositions

A combination pharmaceutical composition including two or more of compound I, compound II, compound III, compound IV, compound V, compound VI, compound VII, and/or pharmaceutically acceptable esters and/or pharmaceutically acceptable salts thereof, according to the invention generally includes about 0.1-99% w/v of each and a pharmaceutically acceptable carrier.

A pharmaceutical composition of the present invention may be in any dosage form suitable for administration to a subject, illustratively including solid, semi-solid and liquid dosage forms such as tablets, capsules, powders, granules, suppositories, pills, solutions, suspensions, ointments, lotions, creams, gels, pastes, sprays and aerosols. Liposomes and emulsions are well-known types of pharmaceutical formulations that can be used to deliver a pharmaceutical agent, particularly a hydrophobic pharmaceutical agent. Pharmaceutical compositions of the present invention generally include a pharmaceutically acceptable carrier such as an excipient, diluent and/or vehicle. Delayed release formulations of compositions and delayed release systems, such as semipermeable matrices of solid hydrophobic polymers can be used.

A pharmaceutical formulation of a composition of the present invention can include a pharmaceutically acceptable carrier. The term "pharmaceutically acceptable carrier" refers to a carrier which is suitable for use in a subject without undue toxicity or irritation to the subject and which is compatible with other ingredients included in a pharmaceutical composition.

Pharmaceutically acceptable carriers, methods for making pharmaceutical compositions and various dosage forms, as well as modes of administration are well-known in the art, for example as detailed in Pharmaceutical Dosage Forms: Tablets, eds. H. A. Lieberman et al., New York: Marcel Dekker, Inc., 1989; and in L. V. Allen, Jr. et al., Ansel's Pharmaceutical Dosage Forms and Drug Delivery Systems, 8th Ed., Philadelphia, Pa.: Lippincott, Williams & Wilkins, 2004; A. R. Gennaro, Remington: The Science and Practice of Pharmacy, Lippincott Williams & Wilkins, 21st ed., 2005, particularly chapter 89; and J. G. Hardman et al., Goodman & Gilman's The Pharmacological Basis of Therapeutics, McGraw-Hill Professional, 10th ed., 2001.

A solid dosage form for administration or for suspension in a liquid prior to administration illustratively includes capsules, tablets, powders, and granules. In such solid dosage forms, one or more active agents, is admixed with at least one carrier illustratively including a buffer such as, for example, sodium citrate or an alkali metal phosphate illustratively including sodium phosphates, potassium phosphates and calcium phosphates; a filler such as, for example, starch, lactose, sucrose, glucose, mannitol, and silicic acid; a binder such as, for example, carboxymethylcellulose, alignates, gelatin, polyvinylpyrrolidone, sucrose, and acacia; a humectant such as, for example, glycerol; a disintegrating agent such as, for example, agar-agar, calcium carbonate, plant starches such as potato or tapioca starch, alginic acid, certain complex silicates, and sodium carbonate; a solution retarder such as, for example, paraffin; an absorption accelerator such as, for example, a quaternary ammonium compound; a wetting agent such as, for example, cetyl alcohol, glycerol monostearate, and a glycol; an adsorbent such as, for example, kaolin and bentonite; a lubricant such as, for example, talc, calcium stearate, magnesium stearate, a solid polyethylene glycol or sodium lauryl sulfate; a preservative such as an antibacterial agent and an antifungal agent, including for example, sorbic acid, gentamycin and phenol; and a stabilizer such as, for example, sucrose, EDTA, EGTA, and an antioxidant.

Solid dosage forms optionally include a coating such as an enteric coating. The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied having a thickness such that the entire coating does not dissolve in the gastrointestinal fluids at pH below 3 associated with stomach acids, yet dissolves above pH 3 in the small intestine environment. It is expected that any anionic polymer exhibiting a pH-dependent solubility profile is readily used as an enteric coating in the practice of the present invention to achieve delivery of the active agent to the lower gastrointestinal tract. The selection of the specific enteric coating material depends on properties such as resistance to disintegration in the stomach; impermeability to gastric fluids and active agent diffusion while in the stomach; ability to dissipate at the target intestine site; physical and chemical stability during storage; non-toxicity; and ease of application.

Suitable enteric coating materials illustratively include cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl; vinyl polymers and copolymers such as polyvinyl pyrrolidone, polyvinyl acetate, polyvinyl acetate phthalate, vinylacetate crotonic acid copolymer, and ethylene-vinyl acetate copolymers; shellac; and combinations thereof. A particular enteric coating material includes acrylic acid polymers and copolymers described for example U.S. Pat. No. 6,136,345.

The enteric coating optionally contains a plasticizer to prevent the formation of pores and cracks that allow the penetration of the gastric fluids into the solid dosage form. Suitable plasticizers illustratively include, triethyl citrate (Citroflex 2), triacetin (glyceryl triacetate), acetyl triethyl citrate (Citroflex A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g. hydroxypropylcellulose, acids or bases) to solubilize or disperse the coating material, and to improve coating performance and the coated product.

Liquid dosage forms for oral administration include one or more active agents and a pharmaceutically acceptable carrier formulated as an emulsion, solution, suspension, syrup, or elixir. A liquid dosage form of a composition of the present invention may include a colorant, a stabilizer, a wetting agent, an emulsifying agent, a suspending agent, a sweetener, a flavoring, or a perfuming agent.

For example, a composition for parenteral administration may be formulated as an injectable liquid. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of a desirable particle size in the case of dispersions, and/or by the use of a surfactant, such as sodium lauryl sulfate. A stabilizer is optionally included such as, for example, sucrose, EDTA, EGTA, and an antioxidant.

For topical administration, a composition can be formulated for administration to the skin such as for local effect, and/or as a "patch" formulation for transdermal delivery. Pharmaceutical formulations suitable for topical administration include, for example, ointments, lotions, creams, gels, pastes, sprays and powders. Ointments, lotions, creams, gels and pastes can include, in addition to one or more active agents, a base such as an absorption base, water-removable base, water-soluble base or oleaginous base and excipients such as a thickening agent, a gelling agent, a colorant, a stabilizer, an emulsifying agent, a suspending agent, a sweetener, a flavoring, or a perfuming agent.

Transdermal formulations can include percutaneous absorption enhancers such as acetone, azone, dimethyl acetamide, dimethyl formamide, dimethyl sulfoxide, ethanol, oleic acid, polyethylene glycol, propylene glycol and sodium lauryl sulfate. Ionotophoresis and/or sonophoresis can be used to enhance transdermal delivery.

Powders and sprays for topical administration of one or more active agents can include excipients such as talc, lactose and one or more silicic acids. Sprays can include a pharmaceutical propellant such as a fluorinated hydrocarbon propellant, carbon dioxide, or a suitable gas. Alternatively, a spray can be delivered from a pump-style spray device which does not require a propellant. A spray device delivers a metered dose of a composition contained therein, for example, using a valve for regulation of a delivered amount.

Ophthalmic formulations of one or more active agents can include ingredients such as a preservative, a buffer and a thickening agent.

Suitable surface-active agents useful as a pharmaceutically acceptable carrier or excipient in the pharmaceutical compositions of the present invention include non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, non-substituted or substituted ammonium salts of higher fatty acids (C10-C22), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, non-substituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidylcholine, dipalmitoylphoshatidyl-choline and their mixtures.

Suitable non-ionic surfactants useful as pharmaceutically acceptable carriers or excipients in the pharmaceutical compositions of the present invention include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with polypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants useful as pharmaceutically acceptable carriers or excipients in the pharmaceutical compositions of the present invention include quaternary ammonium salts, preferably halides, having 4 hydrocarbon radicals optionally substituted with halo, phenyl, substituted phenyl or hydroxy; for instance quaternary ammonium salts containing as N-substituent at least one C8-C22 alkyl radical (e.g. cetyl, lauryl, palmityl, myristyl, oleyl and the like) and, as further sub-stituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, New Jersey, 1981), "Tensid-Taschenbuch", 2nd ed. (Hanser Verlag, Vienna, 1981) and "Encyclopedia of Surfactants (Chemical Publishing Co., New York, 1981).

Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

In particular aspects, a pharmaceutically acceptable carrier is a particulate carrier such as lipid particles including liposomes, micelles, unilamellar or multilamellar vesicles; polymer particles such as hydrogel particles, polyglycolic acid particles or polylactic acid particles; inorganic particles such as calcium phosphate particles such as described in for example U.S. Pat. No. 5,648,097; and inorganic/organic particulate carriers such as described for example in U.S. Pat. No. 6,630,486.

A particulate pharmaceutically acceptable carrier can be selected from among a lipid particle; a polymer particle; an inorganic particle; and an inorganic/organic particle. A mixture of particle types can also be included as a particulate pharmaceutically acceptable carrier.

A particulate carrier is typically formulated such that particles have an average particle size in the range of about 1 nm-10 microns. In particular aspects, a particulate carrier is formulated such that particles have an average particle size in the range of about 1 nm-100 nm.

Detailed information concerning customary ingredients, equipment and processes for preparing dosage forms is found in Pharmaceutical Dosage Forms: Tablets, eds. H. A. Lieberman et al., New York: Marcel Dekker, Inc., 1989; and in L. V. Allen, Jr. et al., Ansel's Pharmaceutical Dosage Forms and Drug Delivery Systems, 8th Ed., Philadelphia, Pa.: Lippincott, Williams & Wilkins, 2004; A. R. Gennaro, Remington: The Science and Practice of Pharmacy, Lippincott Williams & Wilkins, 21st ed., 2005, particularly chapter 89; and J. G. Hardman et al., Goodman & Gilman's The Pharmacological Basis of Therapeutics, McGraw-Hill Professional, 10th ed., 2001.

Commercial packages according to aspects of the present invention include pharmaceutical compositions for use in treatment of cancer in a subject including one or more of: compound I, compound II, compound III, compound IV, compound V, compound VI, compound VII, and/or pharmaceutically acceptable esters and/or pharmaceutically acceptable salts thereof.

Commercial packages according to aspects of the present invention include pharmaceutical compositions for use in treatment of cancer in a subject including two or more of: compound I, compound II, compound III, compound IV, compound V, compound VI, compound VII, and/or pharmaceutically acceptable esters and/or pharmaceutically acceptable salts thereof, wherein the two or more are formulated in combination or separately.

Instructions for administering pharmaceutical compositions for use in treatment of cancer in a subject including any of: compound I, compound II, compound III, compound IV, compound V, compound VI, compound VII, and/or pharmaceutically acceptable esters and/or pharmaceutically acceptable salts thereof, are included in commercial packages according to aspects of the invention. One or more ancillary components is optionally included in commercial packages of the present invention, such as a buffer or diluent.

Assay Systems and Methods

Assay systems for identifying a compound characterized by anti-hormone receptor-dependent cancer activity are provided according to aspects of the present invention which include: A) a first recombinant cell having a nucleus, the first recombinant cell comprising: 1) a reporter gene expression construct including a DNA binding domain recognition sequence in operable linkage with a nucleotide sequence encoding a reporter; 2) an expression construct encoding a fusion protein, the fusion protein including a DNA binding domain and ELK1 (ETS transcription factor (ELK1), transcript variant 1) lacking an ETS (E-twenty-six) DNA binding domain wherein the DNA binding domain is substituted for the ETS DNA binding domain of ELK1; and 3) an expression construct encoding human androgen receptor (AR); wherein the DNA binding domain of the DNA binding domain-ELK1 fusion protein specifically binds to the DNA binding domain recognition sequence of the reporter gene expression construct, and wherein, in the presence of androgen, the AR enters the nucleus of the first recombinant cell and specifically binds to ELK1 in the DNA binding domain-ELK1 fusion protein, thereby activating expression of the reporter gene in the first recombinant cell; and B) a second recombinant cell, the second recombinant cell including: an androgen response element (ARE)-reporter gene expression construct including an ARE in operable linkage with a nucleic acid encoding a reporter; and an expression construct encoding human androgen receptor (AR), wherein in the presence of androgen, the AR enters the nucleus of the second recombinant cell and specifically binds to the ARE, thereby activating expression of the reporter gene in the second recombinant cell.

According to particular aspects, the DNA binding domain recognition sequence of the reporter gene expression construct of the first recombinant cell includes one or more contiguous Gal4 DNA binding domain recognition sequences; wherein the DNA binding domain of the fusion protein is a Gal4 DNA binding domain that specifically binds to the one or more Gal4 DNA binding domain recognition sequences.

According to particular aspects one, two or all of the expression constructs selected from the group consisting of: the reporter gene expression construct; the expression construct encoding a fusion protein; the expression construct encoding AR, is stably integrated in the genome of the first recombinant cell.

According to particular aspects one or both of the expression constructs selected from the group consisting of: the ARE-reporter gene expression construct; and the expression construct encoding AR, is stably integrated in the genome of the second recombinant cell.

Optionally, the reporter gene expression construct of the first recombinant cell and the reporter gene expression construct of the second recombinant cell both encode the same reporter. According to particular aspects, the reporter gene expression construct of the first recombinant cell and the reporter gene expression construct of the second recombinant cell both encode firefly luciferase. Accordingly, assay of reporter expression of the first recombinant cell and the second recombinant cell are performed separately, such as in separate assay vessels, to distinguish the expression of their respective reporters.

Optionally, the reporter gene expression construct of the first recombinant cell and the reporter gene expression construct of the second recombinant cell encode different reporters. Accordingly, assay of reporter expression of the first recombinant cell and the second recombinant cell are performed together or separately, such as in the same or separate assay vessels, to distinguish the expression of their respective reporters.

Assay vessels for performing an assay include, but are not limited to, cell culture plates.

Recombinant cells described herein in detail are genetically modified HeLa cells. Other suitable cell types which can be used include mammalian cells which are "steroid hormone receptor positive." The term "steroid hormone receptor positive" refers to cells which express a particular steroid hormone receptor of interest, such as estrogen receptor and/or androgen receptor. The cells natively express steroid hormone receptor or are genetically modified to express the steroid hormone receptor of interest. As noted herein, the hormone receptor of interest is stably integrated via an expression construct into the cells according to aspects of the present invention.

Regarding the reporter gene nucleic acid expression construct and nucleic acid expression construct encoding a DNA binding domain-ELK1 fusion protein wherein the ETS DNA binding domain of ELK1 is not present and an exogenous DNA binding domain is substituted for the ETS DNA binding domain of ELK1 of the first recombinant cell, the exogenous DNA binding domain specifically binds to the DNA binding domain recognition sequence of the reporter gene expression construct. The identity of the DNA binding domain recognition sequence and exogenous DNA binding domain is not limited and can be any suitable DNA binding domain recognition sequence/DNA binding domain pair which specifically bind to each other. According to aspects described herein, the DNA binding domain recognition sequence is a Gal4 DNA binding domain recognition sequence and the DNA binding domain is a Gal4 DNA binding domain, both of which are well-known in the art, along with variants of each which can be used. More than one Gal4 DNA binding domain recognition sequence is optionally included, such as 2, 3, 4, 5 or more contiguous Gal4 DNA binding domain recognition sequences. See FIGS. 6A and 6B.

Nucleotide sequences encoding human androgen receptor (AR) and androgen response element (ARE) are well-known in the art, along with variants of each which can be used. In particular, the amino-terminal AB domain of AR [AR(A/B)] is sufficient to bind to ELK1, such that AR splice variants containing the AR(A/B) or the AR(A/B) alone are optionally encoded in a nucleic acid expression construct stably incorporated in the genome of the first recombinant cell according to aspects of the present invention.

Splice variants of AR: The ligand binding domain is truncated in most AR splice variants. AR-V7 is a major AR splice variant that confers resistance to castration, enzalutamide and abiraterone. Other AR splice variants lacking the ligand binding domain include AR-V1, AR-V3 and AR-V12. There are a number of additional, less common AR splice variants.

ELK1 is a downstream effector of the MAPK signaling pathway and belongs to the ternary complex factor (TCF) sub-family of the ETS family of transcription factors. ELK1 characteristically binds to purine-rich GGA core sequences, see Shaw PE, et al., Int. J. Biochem. Cell Biol., 2003; 35(8):1210-26. ELK1 is in a repressive association with many cell growth genes. Phosphorylation by ERK transiently stimulates ELK1 to activate its target genes including association with serum response factor (SRF) for activation of immediate early genes, see Shaw PE, et al., Int. J. Biochem. Cell Biol., 2003; 35(8):1210-26; Sharrocks AD., Nature Rev. Mol. Cell Biol., 2001; 2(11):827-37; Shaw PE, et al., EMBO J., 1989; 8(9):2567-74; Gille H, et al., Nature, 1992; 358(6385):414-7; Gille H, et al., EMBO J., 1995; 14(5):951-62; and Zhang HM, et al., NAR, 2008; 36(8): 2594-607. The N-terminal A/B domain of AR [AR(A/B)], which lacks the ligand binding site, is adequate for interaction with ELK1, see Patki M, et al., J. Biol. Chem., 2013; 288(16):11047-65. AR splice variants, which have C-terminal deletions and lack the ligand binding domain (LBD), also synergize with ELK1 and support growth, Rosati R, et al., J. Biol. Chem., 2016; 291(50):25983-25998.

Nucleotide sequences encoding human ELK1 are well-known in the art, along with variants which can be used. Systematic in situ mapping of the ELK1 polypeptide using mammalian two-hybrid assays precisely identified its two ERK docking sites [D-box and DEF (Docking site for ERK, FXFP) motif], and excluded its transactivation domain, as the essential motifs for its cooperation with AR(A/B), wtAR and AR-V7. Surface plasmon resonance (SPR) showed direct binding of purified ELK1 and AR with a dissociation constant of $1.9 \times 10^{-8}$ M. A purified mutant ELK1 in which the D-box and DEF motifs were disrupted did not bind AR. An ELK1 mutant with deletion of the D-box region had a dominant-negative effect on androgen-dependent growth of PCa cells that were insensitive to MEK inhibition.

Compositions and methods of the present invention are not limited to particular amino acid and nucleic sequences identified by SEQ ID. NO herein and variants of a reference nucleic acid or protein may be used.

As used herein, the term "variant" refers to naturally occurring genetic variations and recombinantly engineered variations in a nucleotide sequence or, amino acid sequence which contains one or more changes in its sequence compared to a specified reference sequence while retaining the desired functional properties of the specified reference sequence.

Such changes include those in which one or more amino acid residues have been modified by amino acid substitution, addition or deletion. The term "variant" encompasses orthologs of human nucleotide sequences and amino acid sequences described herein, including for example those derived from mammals and birds, such as, but not limited to orthologs from a non-human primate, cat, dog, sheep, goat, horse, cow, pig, bird, poultry and rodent such as but not limited to mouse and rat.

Mutations can be introduced using standard molecular biology techniques, such as site-directed mutagenesis and PCR-mediated mutagenesis. One of skill in the art will recognize that one or more nucleotide sequence mutations or amino acid sequence mutations can be introduced without altering the functional properties of the specified reference nucleotide sequence or specified reference protein.

Variants of a specified nucleic acid encoding a specified protein described herein are nucleic acids having a nucleotide sequence that has at least 70%, 75%, 80%, 85%, 90%, 91%, 92%, 93%, 94%, 95%, 96%, 97%, 98%, 99% or greater, identity to a nucleotide sequence set forth herein. Variants of a specified nucleotide sequence can encode an amino acid sequence identical to that of a specified protein (due to degeneracy of the genetic code) or a variant of the specified protein.

Variants of a specified protein described herein are proteins having an amino acid sequence that has at least 70%, 75%, 80%, 85%, 90%, 91%, 92%, 93%, 94%, 95%, 96%, 97%, 98%, 99% or greater, identity to an amino acid sequence set forth herein.

Conservative amino acid substitutions can be made in a specified protein to produce a protein variant. Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

Protein variants can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

To determine the percent identity of two amino acid sequences or of two nucleotide sequences, the sequences are aligned for optimal comparison purposes (e.g., gaps can be introduced in the sequence of a first amino acid or nucleotide sequence for optimal alignment with a second amino acid or nucleotide sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/ total number of positions X 100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, PNAS 87:2264 2268, modified as Karlin and Altschul, 1993, PNAS. 90:5873 5877. Such an algorithm is incorporated into the NBLAST and) XBLAST programs of Altschul et al., 1990, J. Mol. Biol. 215:403. BLAST nucleotide searches are performed with the NBLAST nucleotide program parameters set, e.g., for score=100, wordlength=12 to obtain nucleotide sequences homologous to a nucleic acid molecules of the present invention. BLAST protein searches are performed with the) (BLAST program parameters set, e.g., to score 50, wordlength=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389 3402. Alternatively, PSI BLAST is used to perform an iterated search which detects distant relationships between molecules (Id.). When utilizing BLAST, Gapped BLAST, and PSI Blast programs, the default parameters of the respective programs (e.g., of XBLAST and NBLAST) are used (see, e.g., the NCBI website). Another preferred, non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

Proteins and nucleic acids described herein may be generated recombinantly, such as by expression using an expression construct. Proteins and nucleic acids may also be chemically synthesized by well-known methods.

A reporter encoded by expression constructs in the first and second recombinant cells can be any of various reporters that can be used to produce a detectable signal indicative of expression, such as, chloramphenicol acetyltransferase (CAT), alkaline phosphatase, beta-galactosidase, luciferase, and fluorescent proteins such as, Green Fluorescent Protein (GFP), yellow fluorescent protein, cyan fluorescent protein, DsRed and fluorescent variants of any thereof. Methods of detecting a detectable signal of a reporter are well-known in the art.

An expression construct is introduced into the genome of a cell producing a stably integrated genetic modification of the genome of the cell according to aspects of the present invention. The term "stable," "stably integrated" and grammatical equivalents in reference to genetically modified cells refers to the long-term or permanent integration of exogenous DNA into the genome of the cell. Insertion of an expression construct in a cell genome can be confirmed by various well-known methods, including PCR and Southern blot analysis.

The term "genetically modified" and grammatical equivalents in reference to genetically modified cells as used herein refers to the introduction of an exogenous nucleic acid into a cell by genetic engineering techniques or a descendant of such a cell that has inherited at least a portion of the introduced exogenous nucleic acid.

An expression construct is introduced into target cells in order to produce a cell including the expression construct in the genome of the cell using well-known methods, such as lentivirus transduction or other viral transduction methods, microinjection, electroporation, calcium-phosphate precipitation, or lipofection.

Following transduction or transfection, the cells are grown in a medium optimized for the particular cell line. Transduced or transfected cells are typically selected for by including an antibiotic in the medium according to well-established methods.

Integration of an expression construct into the genome of a cell can be determined by genetic analysis, such as PCR, Southern blot, or nucleotide sequencing, and expression of an encoded protein can be determined by protein expression analysis such as by protein analysis (immunocytochemistry, Western blot, ELISA) and/or functional assays.

The terms "expression construct" and "expression cassette" are used herein to refer to a double-stranded recombinant nucleotide sequence containing a desired coding sequence and containing one or more regulatory elements necessary or desirable for the expression of the operably-linked coding sequence. The term "regulatory element" as used herein refers to a nucleotide sequence that controls some aspect of the expression of nucleotide sequences. Exemplary regulatory elements illustratively include an enhancer, a TATA box, an internal ribosome entry site (IRES), an intron, an origin of replication, a polyadenylation signal (pA), a promoter, a transcription termination sequence, and an upstream regulatory domain, which contribute to the replication, transcription, and post-transcriptional processing of a nucleotide sequence. Those of ordinary skill in the art are capable of selecting and using these and other regulatory elements in an expression construct with no more than routine experimentation. Expression constructs may be generated recombinantly or synthetically using well-known methodology.

The term "operably-linked" as used herein refers to a nucleotide sequence in a functional relationship with a second nucleotide sequence.

A regulatory element included in an expression cassette may be a promoter. The term "promoter" as used herein refers to a regulatory nucleotide sequence operably-linked to a coding nucleotide sequence to be transcribed such as a nucleotide sequence encoding a desired sequence of amino acids. A promoter is generally positioned upstream of a nucleotide sequence to be transcribed and provides a site for specific-binding by RNA polymerase and other transcription factors. A promoter may be a constitutive promoter or an inducible promoter. A promoter may provide ubiquitous, tissue-specific, or cell-type specific expression.

In addition to a promoter, one or more enhancer sequences may be included such as, but not limited to, the cytomegalovirus (CMV) early enhancer element and the SV40 enhancer element.

Additional included sequences include an intron sequence such as the beta globin intron or a generic intron, a transcription termination sequence, and an mRNA polyadenylation (pA) sequence such as, but not limited to SV40-pA, beta-globin-pA, and AAT-pA.

An expression construct may include sequences necessary for amplification in bacterial cells, such as a selection marker (e.g., a kanamycin or ampicillin resistance gene) and an origin of replication.

Assays to identify a compound characterized by anti-hormone receptor-dependent cancer activity, including: providing the first recombinant cell and the second recombinant cell; contacting the first recombinant cell and the second recombinant cell with a test compound; and determining the effect of the test compound on expression of a reporter gene in the first recombinant cell and the second recombinant cell compared to an appropriate control, wherein 1) a decrease in expression of the reporter gene in the first recombinant cell compared to a positive control and 2) no change in expression of the reporter gene in the second recombinant cell compared to the positive control, together indicate that the test compound inhibits interaction of the AR with ELK1, thereby identifying a compound characterized by anti-hormone receptor-dependent cancer activity.

Controls are well-known in the art and one of skill in the art would readily recognize an appropriate control and be able to determine an appropriate control for a method of the present invention with no more than routine experimentation.

Testosterone can be used as a negative control in an assay using an assay system according to aspects of the present invention. In the first recombinant cell of the primary screen, testosterone interacts with the AR causing the AR to enter the nucleus. In the nucleus, the AR binds to the DNA binding domain-ELK1 fusion protein, which is bound to the DNA binding domain recognition sequence of the reporter gene expression construct, thereby activating expression of the reporter gene in the first recombinant cell. Testosterone is likewise a negative control in the second recombinant cell in which testosterone interacts with the AR causing the AR to enter the nucleus. In the nucleus, the AR binds to the androgen response element of the androgen response element-reporter gene expression construct, thereby activating expression of the reporter gene in the second recombinant cell.

A positive control can be used. A positive control in this context is a compound that completely inhibits the effect of testosterone in both the primary and counter screen assays. An example of a useful positive control compound in these assays is enzalutamide, which competes with testosterone and binds to AR preventing AR from entering the nucleus. Enzalutamide is regarded as the positive control as it produces the effect that an inhibitory compound would.

An appropriate control may be a reference level of reporter gene expression obtained from similar tests previously and stored in a print or electronic medium for recall and comparison.

A reporter gene included in the first recombinant cell and the second recombinant cell can be the same or different, producing the same or different detectable signal. Where the reporter gene included in the first recombinant cell and the second recombinant cell is different, the cells are optionally assayed for response to a test substance in the same assay vessel and the different detectable signals from different reporter genes in the first and second recombinant cells are detected. Where the reporter gene included in the first recombinant cell and the second recombinant cell is the same, the cells are assayed for response to a test substance in different assay vessels and the detectable signals from the reporter genes in the first and second recombinant cells are detected.

A test compound used in a method of the present invention can be any chemical entity, illustratively including a synthetic or naturally occurring compound or a combination of a synthetic or naturally occurring compound, a small organic or inorganic molecule, a protein, a peptide, a nucleic acid, a carbohydrate, an oligosaccharide, a lipid or a combination of any of these. A test compound may be a naturally-occurring or synthetic chemical compound, or a mixture of two or more thereof. A test compound can be an extract of an environmental sample or organism, such as soil, bacteria, insects or plants, which contain several characterized or uncharacterized components. The components can be further isolated and tested to identify one or more of the components with the desired activity.

In one embodiment, the test compound is a small molecule compound. Individual small molecule test compounds may be identified from combinatorial chemistry libraries, and then further optimized through chemical alterations if desired.

The amount of test compound used in an assay according to aspects of the present invention is generally in the range of about 0.01 nM to 1 mM, for example from 0.1 nM to 100 µM, but more, or less, can be used.

Embodiments of inventive compositions and methods are illustrated in the following examples. These examples are provided for illustrative purposes and are not considered limitations on the scope of inventive compositions and methods.

EXAMPLES

Cell Culture and Reagents

LNCaP, CWR22Rv1, VCaP, DU145, HEK293, H1650 and HeLa cell lines were obtained from the American Type Culture Collection (Manassas, Va.); 293FT cells were obtained from Invitrogen. LNCaP, CWR22Rv1 and H1650 cells were routinely grown at 37° C. in 5% $CO_2$ in RPMI 1640 medium supplemented with 10% FBS (Invitrogen), 100 units/ml penicillin, 100 µg/ml streptomycin, 2 mM L-glutamine mixture (Invitrogen), with the exception that sodium pyruvate (1 mM) (Invitrogen) was included in the LNCaP culture medium alone. VCaP, HEK293, DU145 and HeLa cells were grown in DMEM medium supplemented with 10% FBS (Invitrogen), 100 units/ml penicillin, 100 µg/ml streptomycin, 2 mM L-glutamine mixture (Invitrogen). For hormone depletion, LNCaP cells were grown in phenol-red free RPMI 1640 medium supplemented with 10% heat-inactivated and charcoal-stripped FBS (Sigma) and 100 units/ml penicillin, 100 µg/ml streptomycin, 2 mM L-glutamine mixture for 96 hours before each experiment. Affinity-purified rabbit anti-human antibody to AR (sc-7305) and mouse antibody to GAPDH (sc-47724) were purchased from Santa Cruz Biotechnology (Santa Cruz, Calif.). Rabbit monoclonal anti-human antibody to ELK1 (ab32106) was from Abcam (Cambridge, Mass.). Testosterone was obtained from Sigma-Aldrich. Lipofectamine™ 2000 was purchased from Thermo Scientific (product number 78410). 5,7,3',4'-Tetrahydroxyflavone was from Selleckchem (S2320); 5,7,3',4'-Tetrahydroxyisoflavone was obtained from BOC Sciences (480-23-9). The following compounds were obtained from INDOFINE Chemical Company: 5,7,3',4'-Tetrahydroxyflavanone (021111S); 5,3',4'-Tetrahydroxyflavone (T-406); 5,3'-Dihydroxyflavone (D-409); 7,4'-Dihydroxyflavone (D-412); 5-Hydroxyflavone (H-025); 3'-Hydroxyflavone (H-410); 5,3'-Dihydroxy-6,7,4'-trimethoxyflavone (D-123). The following compounds were obtained from Extrasynthase: 3',4',7-Trihydroxyflavone (1223); 5,7-Dihydroxyflavone (1362S); 3',4'-Dihydroxyflavone (1204); 4',5,7-Trihydroxy-3'-methoxyflavone (1104S); 3',4',5,7-Tetrahydroxyflavone-3-methoxyflavone (1342); 3',4',5,7-Tetramethoxyflavone (1204). The following compounds were from Cayman Chemical: 4',5,7-Trihydroxyflavone (Ser. No. 10/010,275) and 5,7,3'-Trihydroxy-4'-methoxyflavone (18649). 7,3'-Dihydroxyflavone was from Sigma-Aldrich (CDS06791). 4',5-Dihdyroxyflavone was obtained from Santa Cruz Biotechnology (Santa Cruz, Calif.) (sc-267859). shRNAs targeting AR and ELK1 and non-targeting control shRNA in the lentiviral expression vector pLKO1-puro were purchased from Sigma-Aldrich. The pLVX-AR-V7 plasmid and pLVX control plasmid were obtained from Dr Yan Dong from Tulane University (New Orleans, La.).

Gal4 DNA binding domain recognition sequence, vector containing luciferase reporter gene attached to a TATA box containing promoter and the manner in which the Gal4-TATA-Luciferase construct was generated Custom synthesized PCR primers were used to amplify and clone the five tandem Gal4 elements from the pG5luc vector (Promega) into the pGreenFire1™-mCMV-EF1-Neo (Plasmid) at SpeI (upstream) and BamHI (downstream) sites. pG5luc Vector is well known and the complete sequence has NCBI accession #AF264724

Generation of the Gal4-ELK1 fusion protein construct

The Gal4 fusion with ELK1 in which the DNA binding domain of ELK1 (amino acids 1-86) was deleted was constructed by PCR using the ELK-pCMV expression plasmid (Origene, Rockville, Md.) as the template and the appropriate primers subcloned at BamHI (upstream) and NotI (downstream) sites in a vector expressing Gal4 fusions (pBind). The Gal4 ELK1 fusion sequence was then cloned into the pCDH-CMV-MSC-EF1-Hygro cDNA cloning and expression vector at XbaI site (upstream) and BamHI (downstream) sites.

Generation of recombinant cell lines for high throughput screening and counter screening of small molecule libraries HeLa HLR cells obtained from Dr. Johann Hofman (Innsbruck Medical University), which were originally designed to serve as a cell-based assay system to measure modulation of MAPK activity. HeLa HLR cells have a stably integrated minimal promoter-luciferase reporter containing five upstream Gal4 elements (Gal4-TATA-Luc) and also constitutively express a Gal4-ELK1 fusion protein in which the Gal4 DNA binding domain is substituted for the ETS DNA binding domain of ELK1. In order to produce recombinant cell lines for high throughput screening and counter screening of small molecule libraries, HeLa HLR were stably transduced with a vector expressing the full-length AR. A sequence encoding the full length AR (SEQ ID NO:9) was subcloned from the pCMV expression vector (Origene) into the pCDH-CMV-MCS-EF1-Puro cDNA Cloning and Expression Vector (System Biosciences) at NheI (upstream) and BamHI (downstream) sites. The lentiviral vector expressing full length AR was then packaged in lentivirus and the HeLa HLR cells were infected as described below in the sub-section "Lentivirus-mediated-Transduction." After 72 hours (h) of infection, 2 ug/mL of puromycin was added to the culture medium to select for the transduced cells. The cells were plated at low density for colony formation (20-40 colonies) in a 100 mm dish. Clonal cells were isolated using cloning cylinders from CORNING (Cat. #3166-8). The selected clones were further expanded and then tested for luciferase induction by testosterone. The clone that gave the greatest luciferase signal to noise ratio in response to testosterone treatment was then chosen for use in the primary screening assay for high throughput small molecule screening.

The cells generated for counter screening, are HeLa cells stably transduced with a lentiviral plasmid construct containing a minimal promoter-luciferase reporter and an upstream androgen response element (ARE) sequence. These HeLa cells were also transduced with a lentiviral expression plasmid encoding the full-length AR. These lentiviral constructs were made as follows. Custom synthesized PCR primers were used to amplify and clone the ARE sequence from a pG5luc plasmid construct containing an ARE sequence element into the pGreenFire1 ™-mCMV-EF1-Neo (Plasmid) at SpeI (upstream) and BamHI (downstream) sites. pG5luc Vector is well known and the complete sequence has NCBI accession #AF264724. The ARE containing pG5luc plasmid is described in detail in Patki et al., 2013, J Biol Chem, 288:11047-11065. The lentiviral vector expressing ARE-luciferase reporter was then packaged in lentivirus and parental HeLa cells were infected as described below under the heading "Lentivirus-mediated-Transduction." After 72h of infection, 400 ug/mL of Geneticin was added to the culture medium to select for the transduced cells. These cells were then infected with the lentivirus containing the full length AR expression plasmid described above. After 72h of infection, 2 ug/mL of Puromycin was added to the culture medium to select for the transduced cells. Clonal cells harboring both the ARE-promoter-luciferase reporter and also stably expressing AR were then isolated using cloning cylinders as described above. The selected clones were further expanded and then tested for luciferase induction by testosterone. The clone that gave the greatest luciferase signal to noise ratio in response to testosterone treatment was then chosen for use in the counter screening assay for high throughput small molecule screening. All of the plasmid constructs generated above were sequenced to verify DNA sequences before, the constructs were used.

The recombinant HeLa cells generated above were routinely grown in DMEM supplemented with 10% FBS and 100 units/ml penicillin, 100 μg/ml streptomycin, 2 mM L-glutamine mixture (Invitrogen) and the appropriate selection antibiotics. The antibiotics used in the culture media for the primary screening cells included 100 μg/ml Hygromycin (Invitrogen) (to maintain Gal4-ELK1), 100 μg/ml Geneticin (Invitrogen) (to maintain Gal4-TATA-Luc) and 2 μg/ml Puromycin (Sigma-Aldrich) (to maintain AR). The antibiotics used in the culture media for the counter screening cells included 400ug/ml Geneticin (Invitrogen) (to maintain ARE-TATA-Luc) 2 μg/ml Puromycin (Sigma-Aldrich) (to maintain AR).

High Throughput Screening

For high throughput screening, recombinant primary screening cells were first depleted of hormone by growing them for 24h in medium in which the serum used was heat-inactivated and charcoal-stripped. The cells were then plated in 384-well white flat bottom plates (5,000 cells/well) (Corning Product #3570) using a Multidrop (Thermo Fisher Scientific, Waltham, Mass.). The plates were then incubated for 24h prior to adding test compounds. The following day test compounds from the LOPAC, Prestwick, or Maybridge Hitfinder libraries were added precisely in a 0.2 μL volume in the test wells using a Biomek FX liquid handler (Beckman Coutler, Break, Calif.) to achieve final media concentration of 10 μM of each test compound. Using the Multidrop (ThermoLab Systems, Helsinki, Finland), testosterone was added in addition to the test compounds to achieve a final media concentration of 10 nM. As the test compounds were re-constituted from powder stocks using dimethyl sulfoxide (DMSO) as the solvent, the final media concentration of DMSO was 0.4% v/v. For the assay negative control on each plate, one row of wells on each plate contained 10 nM testosterone and 0.4% v/v of DMSO. For the assay positive control on each plate, one row of wells on each plate contained 10 nM testosterone and 10 uM enzalutamide dissolved in DMSO (0.4% v/v of DMSO in the wells). The plates were incubated for 24h at 37° C. in 5% $CO_2$. The medium was then aspirated leaving a residual volume 10 μl using an Elx 405-plate washer (Bio Tek U.S.). Then, 10 uL of the assay reagent Bright-Glo (Promega Corp., Madison Wis.) was added to each well. Luciferase activities in the wells were then measured using a PHEROStar plate reader (BMG Labtech, Ortenburg, Germany. A total of 18,270 compounds were tested in the primary screen. A 'hit' was initially defined using relatively low stringency criteria as a compound able to reduce luciferase activity in the test well ≥3 standard deviations below the negative control wells or to a level ≥40% of the enzalutamide control wells. For the primary assay this definition produced 1613 hits for an overall hit rate of 8.8%. The 1613 compounds were then tested again in the primary screening assay in parallel with the counter screening assay in triplicate at 10 uM, with compound additions to plates using Mosquito X1 (Hertfordshire, UK). A hit was now redefined as a test compound able to reduce luciferase activity in the test wells ≥3 standard deviations below the negative control wells and that was unable to reduce luciferase activity ≥50% in the counter screen. By this definition, 92 hits were obtained. Compounds were further triaged based on their ability to reduce luciferase activity in the primary screen by ≥80% and produced no inhibition in the counter screen. One of the top hits was prioritized for this study.

Purified Proteins

Full length human AR expressed in insect cells and purified to ≥95% by affinity chromatography and FPLC chromatography (ab82609) was purchased from Abcam (Cambridge Mass.). Recombinant his-tagged ELK1 expressed from baculovirus infected Sf9 cells were purified using nickel agarose affinity chromatography as described in Rosati R, et al., JBC, 2016, 291(50):25983. The proteins were eluted with 200 mM imidazole and dialysed against 20 M HEPES, pH 7.9 containing 10% glycerol, 20 mM KCl, 2 mM $MgCl_2$, 0.2 mM EDTA, 0.5 mM benzamidine and 0.5 mM DTT. Purity of the proteins was estimated to be ≥85% by SDS-polyacrylamide gel electrophoresis.

Surface Plasmon Resonance

Amine Coupling Kit, CM5 sensor chip and HBS-N buffer (GE Healthcare) were used for surface plasmon resonance (SPR) analysis. The rate and equilibrium binding constants of the interaction of AR with KCI807 was determined using Biacore 3000 (Biacore, Piscataway, N.J.). Depending on the experimental plan, affinity-purified AR or ELK1 polypeptide (ligand) was immobilized on a CM5 research grade sensor chip by an amine coupling method according to the method described in Johnsson B et al., Anal. Biochem., 1991; 198(2):268-77. The immobilization involved activation of carboxymethyl groups on a dextran-coated chip by reaction with N-hydroxysuccinimide, followed by covalent bonding of the ligand (AR) to the chip surface via amide linkages. Reference surfaces were prepared in the same manner but blocked with ethanolamine and thus contained no ligand. To examine binding of KCI807 or enzalutamide, kinetic binding analysis was carried out, by injecting the KCI807 or enzalutamide (analyte) at different concentrations (0-320 nM for KCI807 or 0-200 nM for enzalutamide) into the flow cells (ligand and reference cell). The interaction (response units, RU) between analyte and ligand was recorded as the ligand RU minus the reference RU. Kinetic values were determined using BIAevaluation software (Biacore), and the data were fitted with the model showing closest match, according to methods described in Drescher DG et al., Methods Mol. Biol., (Clifton, N. J.). 2009; 493:323-43; and Selvakumar D et al., JBC, 2013; 288(10):7215-29. A 1:1 Langmuir binding model was generally selected, in which all the sensorgrams representing the different analyte concentrations were fitted simultaneously with the wide window of association and dissociation phases. Individual concentration curves were also evaluated to confirm the fitting data. The equilibrium dissociation constant ($K_d$) was calculated by $k_d=k_{off}/k_{on}$. In all cases, baseline was established in the presence of the vehicle used for the compounds (DMSO) appropriately diluted in BBS-N buffer.

Competition binding experiments were executed on the Biacore 3000 system at a flow rate of 5-10 µl/min in BBS-N buffer according to methods described in Gao Y et al., Anal. Methods. 2012; 4(11):3718-23; and Bahloul A et al., Human molecular genetics. 2010; 19(18):3557-65. A fixed concentration (200 nM) of AR in the presence of increasing concentrations of KCI807 or enzalutamide was passed over a covalently stabilized ELK1 sensor surface for 5 min at 50 µl min$^{-1}$. The sensor surface was regenerated between experiments by dissociating any formed complex in HBS-N buffer for 30 min, followed by a further 30-min stabilization period. After regeneration, the SPR signal returned to the original level (baseline). In all cases, baseline was established in the presence of the vehicle used for the compounds (DMSO) appropriately diluted in HBS-N buffer. The binding curves were analyzed using the heterogeneous analyte competition model. The kinetic curves were analyzed for a one-to-one Langmuir fitting model provided by with the Biacore 3000 instrument software.

Transfections and Reporter Luciferase Assays

Hela Cells were plated in a 24-well plate at a concentration of 75,000 cells/well in antibiotic-free red DMEM. The following day the cells were transfected with a total of 300 ng of plasmid DNA/well using Lipofectamine 2000. The cells were incubated for 24h then lysed using luciferase assay lysis buffer 5X from Promega. The luciferase activity of the cell lysates were measured using firefly substrate from Promega and a luminometer (Lumat LB9501, Berthold, Wildbad, Germany).

Lentivirus-mediated-Transduction shRNAs for ELK1, AR, and non-targeting control shRNA were packaged in 293FT cells. The lentiviral vector expressing ARE-luciferase reporter was packaged in 293FT cells. The lentiviral particles were generated using lipofectamine and three plasmids, pMD2G, pMDLg/RRE, and pRSV/Rev which all code for essential elements of the virus. The virus containing supernatant was harvested at 48 and 72 h after transfection. Cells were plated in 6-well poly-D-lysine coated plates (BD Falcon) in phenol red-free medium supplemented with 10% heat-inactivated charcoal-stripped FBS and 2 mM L-glutamine. The following day, cells were infected with ARE-luciferase reporter, control shRNA, ELK1 shRNA, or AR shRNA lentivirus with Polybrene (8 µg/ml) for a 5h duration, followed by an additional 5h. After infection, the virus was replaced with fresh phenol red-free growth medium.

Colony Growth Assay

Cells were trypsinized, and 1000 cells/well were seeded in poly-D-lysine coated 6-well plates in phenol red-free regular growth media. The cells were treated with the indicated concentration of KCI807, which was replenished every 48h. The cells were grown at 37° C. in 5% $CO_2$ for 10 days until colonies-grew to the desired size in the untreated control wells. Colonies were fixed with methanol and stained with crystal violet. Each treatment was conducted in triplicate and the number of colonies was counted using the GelCount™ colony counter and a 350 size cutoff.

Cell Monolayer Growth Assay

Cells were trypsinized and 3000-4000 cells/well were seeded in 96-well plates coated with poly-D-lysine. The cells were seeded in phenol red-free medium supplemented with 10% FBS, 100 units/ml penicillin, 100 µg/ml streptomycin, 2 mM L-glutamine mixture and sodium pyruvate (1 mM) for LNCaP cells and phenol red-free medium supplemented with 10% FBS, 100 units/ml penicillin, 100 µg/ml streptomycin and 2 mM L-glutamine mixture for VCaP, 22Rv1, DU145, HeLa, HEK293 and H1650 cells. The cells were grown at 37° C. in 5% $CO_2$. Twenty four hours after seeding in the 96-well plates, the cells were treated with the indicated concentration of KCI807 or DMSO (vehicle). The cells were re-treated on Day 3 by removing half the volume of medium and replacing it with fresh treated medium. Cell viability was determined using the MTT assay from day zero until day five. MTT (10 µL, 5 mg/mL) was added to each well and incubated for 2h at 37° C. The formazan crystal sediments were dissolved in 100 µL of DMSO, and the absorbance at 570 nm was measured using the BioTek Synergy 2 Microplate Reader (BioTek, Winooski, Vt.). The assay was conducted in sextuplicate wells and values were normalized to day zero.

Western Blot Analysis

The treated cells were washed once with phosphate buffered saline (PBS) and then lysed with RIPA buffer (150 mM NaCl, 1% Nonidet P-40, 0.5% sodium deoxycholate, 0.1% SDS, 50 mM Tris of pH 8.0) containing a protease inhibitor cocktail (Pierce, Thermo Fisher Scientific). The cell lysates were then incubated on ice for 40 minutes and vortexed every 10 minutes. Total protein concentrations were estimated using the Bradford Assay (Bio-Rad). Ten micrograms of each protein sample was heated at 95° C. for 5 minutes and resolved by electrophoresis on 8% polyacrylamide-SDS gels and electrophoretically transferred to PVDF membranes (Millipore, Billerica, Mass.). The membranes were then probed overnight at 4° C. with the appropriate primary antibody followed by the appropriate horseradish peroxidase-conjugated secondary antibody. The blots were then developed to visualize the protein bands using the HyGLO Chemiluminescent HRP Antibody Detection Reagent (Denville Scientific, Metuchen, NI).

RNA isolation, Reverse Transcription, and Real Time PCR.

Total RNA was isolated from cells using the RNeasy Mini Kit (Qiagen). Reverse transcription PCR was then performed using 500 ng of total RNA with random primers and using the high-capacity complementary DNA Archive kit (Applied Biosystems). The complementary DNA from this reaction was measured using quantitative real time PCR using the StepONE Plus Real Time PCR system (Life Technologies Corporation, Carlsbad, Calif.). All reactions were performed in triplicate and normalized to glyceraldehyde-3-phosphate-dehydrogenase values in the same samples. All primers and Taqman probes were purchased from the applied Biosystems inventory (Invitrogen)

mRNA expression profiling mRNA expression profiling was performed at RUCDR Infinite Biologics, Piscataway, N.J. using Clariom D Arrays. The samples were amplified using Ovation Pico WTA System Version 2 kits from Nugen (P/N: 3302-96) following the procedure detailed in the User Guide from an original input of 40ng of RNA. The amplification was automated on the Caliper Sciclone liquid handling workstation from Perkin Elmer (P/N: 124901). The amplified cDNA underwent a QC check using the Trinean Dropsense96 to confirm that a sufficient amount was generated and that it was of an appropriate quality to be used for the next step. Amplified cDNA was then fragmented and labeled using the Encore Biotin Module from Nugen (P/N: 4200-96) following the procedure detailed in the User Guide. Following fragmentation, 2 uL of the fragmented product was used for a QC check on the Caliper LabChip GX from Perkin Elmer to confirm that the samples were adequately fragmented and were within the correct size range. Fragmented and labeled cDNA was hybridized to the Affymetrix Clariom D cartridge array (P/N: 902922) using the GeneChip Hybridization, Wash, and Stain Kit (P/N: 900720) and following the procedure detailed in the User Guide. The cartridges were placed in a rotisserie hybridization oven at 45° C. for 16 h to hybridize. The hybridized cartridges were then washed and stained on the GeneChip Fluidics Station 450 (P/N: 00-0079) from Affymetrix following the procedure detailed in the User Guide. They were then immediately scanned on the GeneChip Scanner 3000 7G (P/N: 00-00212) from Affymetrix. After the scans were complete, the Cel data files were run through a QC check using Affymetrix Expression Console software (now part of Transcriptome Analysis Console (TAC) Software). The PM means were checked to ensure consistency across the processed samples and to meet a minimum threshold. Hybridization controls were graphed to ensure consistent hybridization within the samples. Feature intensity and probeset means were also graphed and checked.

Measurement of intracellular and serum levels of compounds

Chromatographic and mass-spectrometric conditions

Instrumentation

All LC-MS/MS analyses were performed on an AB SCIEX (Foster City, Calif.) QTRAP 6500 LC-MS/MS system, which consists of a SHIMADZU (Kyoto, Japan) Nexera ultra-high performance liquid chromatography (UPLC) coupled with a hybrid triple quadrupole/linear ion trap mass spectrometer. The UPLC system is equipped with two X2 LC-30AD pumps, an X2 SIL-30AC autosampler, a CBM-20A communication bus module, an X2 CTO-30A column oven, and two DGU-20A degassing units. Analyst®1.6 software was used for system control and data acquisition, and MultiQuant 3.0 software was used for data processing and quantitation.

Liquid Chromatography

Chromatographic separation was achieved on a Waters XBridge C18 (2.1×50 mm, 3.5 µm) column using an optimized gradient elution consisting of mobile phase A (0.1% formic acid in water) and mobile phase B (0.1% formic acid in acetonitrile), at a flow rate of 0.3 mL/min. The elution gradient program was as follows [shown as the time (min), (% mobile phase B)]: 0-2.5 min, 40%; 2.5-4.5 min, 40-55%; 4.5-5 min, 55-100%; 5-6 min, 100%; 6-6.5 min, 100-40%; 6.5-10 min, 40%. Column oven temperature was maintained at 40° C. To minimize the carryover, external and internal washes were implemented prior to and post the injection for both the auto-sampler syringe and injection port, as follows: 50% methanol (for $R_3$) was used for external wash with one second rinse dip and 500 µL volume, and the mixture of IPA:MeOH:Acetonitrile:$H_2O$ 1:1:1:1 (for $R_1$) and 40% acetonitrile (R0) was used in the internal wash with sequence $R_1$ to R0.

Mass spectrometry (MS)

The QTRAP 6500 mass spectrometer was operated in electrospray positive ionization using multiple reaction monitoring mode (MRM). The MS parameters were optimized to obtain the most sensitive and specific MS transitions for 5,3'-dihydroxyflavone, 5,3',4'-trihydroxyflavone, and 5,7,3',4'-tetrahydroxyflavone by direct infusion 0.5 µM of the standard solutions into the ion source with a syringe pump. The Turbo ion-spray voltage was set at 4500 V and the source temperature was set at 500° C. Collision gas was optimized at medium level with curtain gas, ion source gas 1 and ion source gas 2 delivered at 20, 30 and 30 psi, respectively. The dwell time was set for 50 ms. For each compound, four most sensitive MS transitions were selected and the corresponding decluttering potential, collision energy, collision cell exit potential, and entrance potential were optimized as shown in Table 2.

TABLE 2

| Q1 | Q3 | time | ID | DP | CE | CXP |
|---|---|---|---|---|---|---|
| 255 | 137.1 | 50 | 5,3'-dihydroxyflavone_1 | 130 | 41.5 | 23.3 |
| 255 | 152 | 50 | 5,3'-dihydroxyflavone_2 | 130 | 61.9 | 25.8 |
| 255 | 181 | 50 | 5,3'-dihydroxyflavone_3 | 130 | 43.5 | 16.9 |
| 255 | 155 | 50 | 5,3'-dihydroxyflavone_4 | 130 | 54.1 | 25 |
| 271.3 | 117.1 | 50 | 5,3',4'-trihydroxyflavone_1 | 99.7 | 46.2 | 13.8 |
| 271.3 | 135 | 50 | 5,3',4'-trihydroxyflavone_2 | 99.1 | 39.1 | 11.9 |
| 271.3 | 137.1 | 50 | 5,3',4'-trihydroxyflavone_3 | 97 | 39.7 | 12.3 |
| 271.3 | 225.1 | 50 | 5,3',4'-trihydroxyflavone_4 | 97.4 | 41.8 | 13.6 |
| 287.5 | 135 | 50 | 5,7,3',4'-tetrahydroxyflavone_1 | 118.9 | 39.2 | 15.7 |
| 287.5 | 153 | 50 | 5,7,3',4'-tetrahydroxyflavone_2 | 120 | 41.8 | 13.9 |
| 287.5 | 160.9 | 50 | 5,7,3',4'-tetrahydroxyflavone_3 | 112.4 | 44.9 | 22.1 |
| 287.5 | 241 | 50 | 5,7,3',4'-tetrahydroxyflavone_4 | 82.3 | 41 | 13.9 |

Sample Preparation

Stock solutions, calibration standards, and quality control (QC) samples

The stock solutions were prepared in DMSO at a final concentration of 5 mM, and stored in brown glass vials at −20° C. The working solutions were prepared freshly by serial dilutions of the stock solution with DMSO on each day of analysis. For the concentration determination in mouse serum or cell samples, the calibration standards were prepared by spiking 5 µL of working solution into 95 µL of blank human plasma or untreated cell lysate, respectively. All standards were prepared fresh daily.

Mouse serum samples for the determination of serum concentrations of 5,3'-dihydroxyflavone Frozen serum samples were thawed at room temperature. An aliquot of 100 µL serum was transferred into a micro centrifuge tube, and 1000 µL ethyl acetate was added. The mixture was vortex-mixed for 15 minutes and centrifuged at 14000 rpm at 40 C for 15 min. 950 uL of the supernatant was transferred to a new 1.7 mL centrifuge tube, and dried under a steam of nitrogen at room temperature. The sample was then reconstituted with 100 µL 40% acetonitrile, and 5 µL was injected into the LC-MS/MS system.

Cell samples for the determination of intracellular concentrations of 5,3'-dihydroxyflavone, 5,3',4'-trihydroxyflavone, or 5,7,3',4'-tetrahydroxyflavone The suspended cells were sonicated to cell lysate, and then 1000 µL ethyl acetate was added. The mixture was vortex-mixed for 15 minutes and centrifuged at 14000 rpm at 40 C for 15 min. 950 uL of the supernatant was transferred to a new 1.7 mL centrifuge tube, and dried under a steam of nitrogen at room temperature. The sample was then reconstituted with 100 µL 40% acetonitrile, and 5 µL was injected into the LC-MS/MS system. Measured concentrations were normalized to cell protein concentrations.

Determination of serum levels of KCI807 and identification of its metabolites by LC-MS/MS Determination of KCI807 serum levels The concentrations of KCI807 in mouse serum samples were quantitatively determined by liquid chromatography coupled with tandem mass spectrometry (LC-MS/MS). In brief, 50 µL of mouse serum was acidified by adding 50 µL 1% formic acid, followed by extraction with 0.5 mL ethyl acetate. The top layer was transferred to a new tube and evaporated to dryness under a stream of nitrogen in a water bath at 37° C. The residual was reconstituted in 50 µL mobile phase, and the supernatant was subjected to the LC-MS/MS analysis. LC-MS/NIS analyses were performed on an AB SCIEX (Foster City, Calif.) QTRAP 6500 LC-MS/MS system, which consists of a SHIMADZU (Kyoto, Japan) Nexera ultra high performance liquid chromatography system coupled with a hybrid triple quadrupole/linear ion trap mass spectrometer. Chromatographic separation was performed on a Waters Xterra C18 column (50×2.1 mm, 3.5 µm) under a gradient elution consisting of mobile phase A (0.1% formic acid in water) and mobile phase B (0.1% formic acid in acetonitrile), at the flow rate of 0.3 mL/min. KCI807 was monitored using the multiple reaction monitoring mode under positive electrospray ionization. Mass spectrometer parameters were optimized to obtain the most sensitive and specific mass transitions for KCI807 by direct infusion 0.5 µM of the standard solution into the ion source with a syringe pump. The Turbo ion-spray voltage was set at 4500 V and the source temperature was set at 500° C. Collision gas was optimized at medium level with curtain gas, ion source gas 1 and ion source gas 2 delivered at 20, 30 and 30 psi, respectively. The dwell time was set for 50 ms. KCI807 was monitored at the most sensitive and specific mass transition of m/z, 254.9>137.0. The linear calibration curve was established at KCI807 concentration range of 5-1000 nM in mouse serum. The intra- and inter-day precision, and accuracy of the quality control samples were within the generally acceptable criteria for bioanalytical methods (<15%).

Metabolite Identification

To identify potential metabolites of KCI807 in mice, serum and liver samples collected from the control (untreated) and KCI807-treated mice were subjected to the LC-MS/MS analysis. Sample preparation and chromatographic separation were the same as that described above. Column eluents of the control and drug-treated samples were surveyed using different scan modes including full scan, product scan, and multiple reaction monitoring scan. Due to the lack of adequate sensitivity in the full scan and product scan modes, the multiple reaction monitoring scan mode was selected to detect potential metabolites of KCI807, including those involved in methylation, oxidation, reduction, glucuronidation, glycosylation, acetylation, sulfation, as well as double-modifications (e.g., glucuronide-glucuronide, glucuronide-sulfate, glucuronide-glycosylate, and sulfate-glycosylate double conjugates). The LC-MS/NIS was operated under the optimized condition as for KCI807, and hypothesized theoretical mass transitions for potential metabolites were monitored (see Tables 3 and 4).

Table 3 shows hypothesized theoretical mass transitions for KCI807 Potential metabolites with a single chemical modification

TABLE 3

| Modification | Form | Mass shifted from KCI807 | Hypothesized Q1 | Hypothesized Q3 | | |
|---|---|---|---|---|---|---|
| | | | | Q3-1 | Q3-2 | Q3-3 |
| Glucuronidation | +C6H8O6 | 176.03 | 431.09 | 255 | 313.03 | 137 |
| methylation | +CH2 | 14.02 | 267.07 | 255 | 151.02 | 137 |
| oxidation | +O | 15.99 | 271.05 | — | 153 | 137 |
| reduction | −O | −15.99 | 239.07 | — | 121.02 | 137 |
| glycosylation | +C6H10O5 | 162 | 417.11 | 255 | 299.05 | 137 |
| acetylation | +C2H2O | 42.01 | 299.07 | 255 | 179.02 | 137 |
| Sulfation | +O3S | 79.96 | 335.02 | 255 | 216.97 | 137 |

Q1, mass charge ratio for the parent ion of the metabolite;

Q3, mass charge ratio for the product ion of the metabolite

Table 4 shows hypothesized theoretical mass transitions for KCI807 potential metabolites with double chemical modifications

TABLE 4

| Modifications | Form | Mass shifted | Hypothesized Q1 | Hypothesized Q3 | | | | | |
|---|---|---|---|---|---|---|---|---|---|
| | | | | Q3-1 | Q3-2 | Q3-3 | Q3-4 | Q3-5 | Q3-6 |
| Glucuronide-glucuronide | +C12H16O12 | 352.06 | 607.12 | 431.09 | N/A | 255.06 | 313.03 | N/A | 137 |
| Glucuronide-sulfate | +C6H8O9S | 255.99 | 511.05 | 335.02 | 431.09 | 255.06 | 313.03 | 216.96 | 137 |
| Glucuronide-glycosylate | +C12H18O11 | 338.03 | 593.09 | 417.06 | 431.09 | 255.06 | 313.03 | 299 | 137 |
| Sulfate-glycosylate | +C6H10O8S | 241.96 | 497.02 | 417.06 | 335.02 | 255.06 | 216.96 | 299 | 137 |

Figure 20:
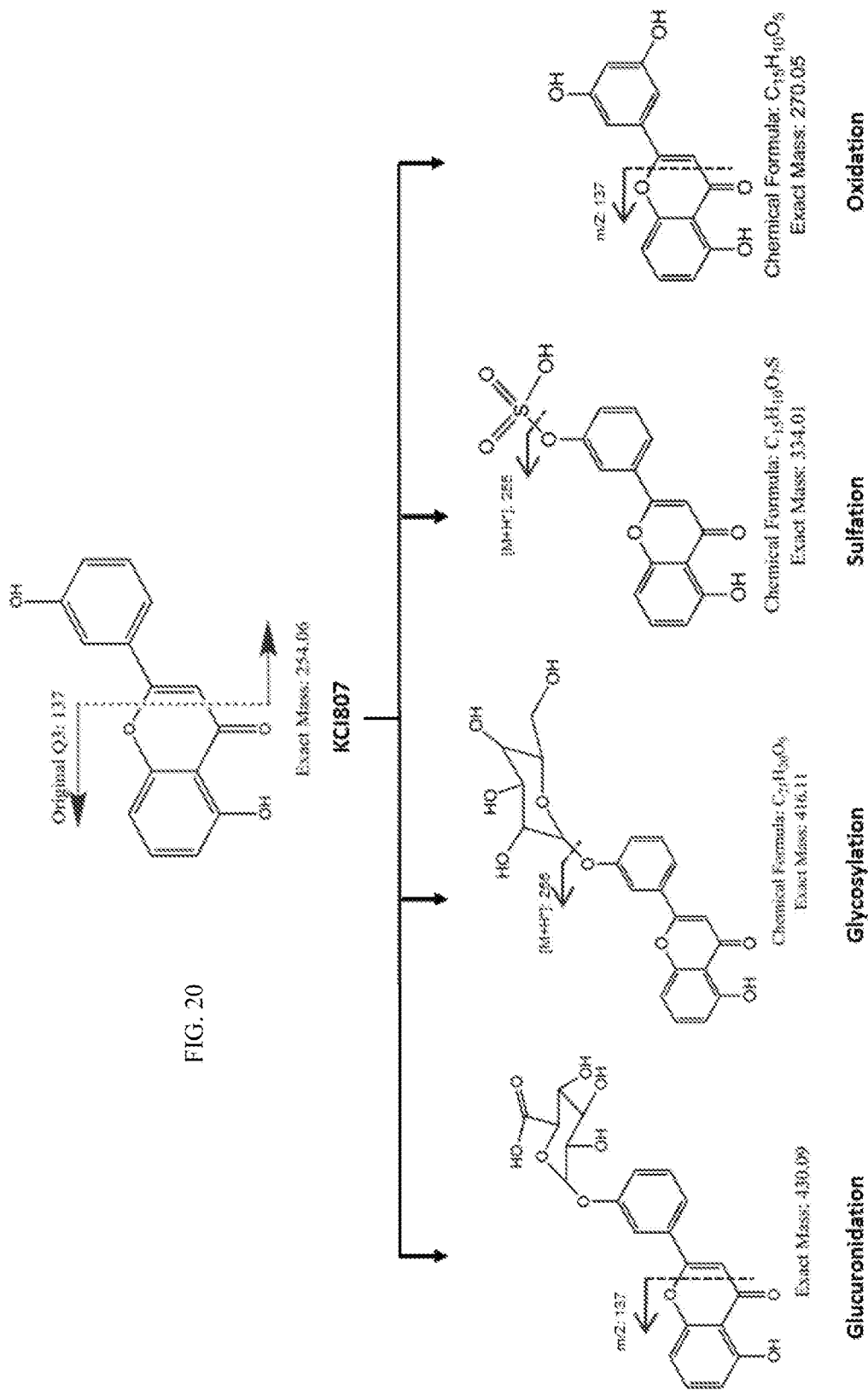
FIG. 20 is a diagram showing chemical structures and major fragmented positions for KCI807 and metabolites detected in the KCI807-treated mouse serum samples.
Figure 21:
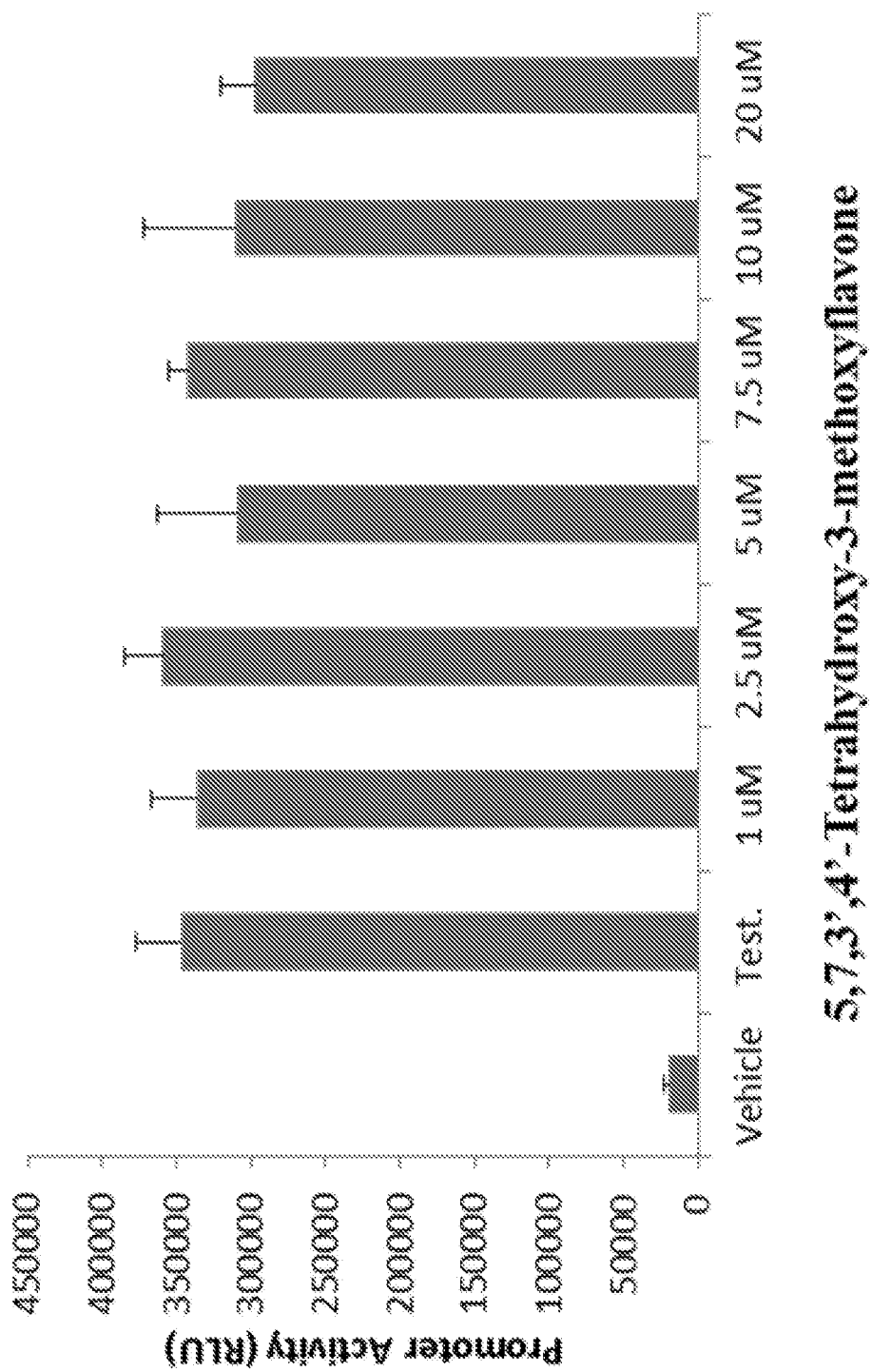
FIG. 21 is a graph showing the effect of 5,7,3',4'-tetrahydroxy-3-methoxyflavone on ELK1-dependent promoter activation by AR. The recombinant HeLa cells used for the primary compound screening assay were treated with vehicle or testosterone and the indicated concentrations of the compound for 6 hours at 37 degrees Celsius and the luciferase reporter activity was then measured. The data shows lack of inhibition of the promoter activity by 5,7,3',4'-tetrahydroxy-3-methoxyflavone, indicating that methoxy substitution on C3 abrogates activity of the compound.

Q1, mass charge ratio for the parent ion of the metabolite;
Q3, mass charge ratio for the production of the metabolite If a chromatographic peak monitored at the theoretical transition(s) corresponding to a particular metabolite was identified in the drug-treated samples but not in the control (untreated) samples, this metabolite was identified as a metabolite of KCI807, see FIG. 20.

Tumor Xenograft Model Studies

The 22Rv1 human CRPC xenograft model was established by bilateral subcutaneous (SC) implant of 22Rv1 cells and serial passaging of the tumors in male SCID mice. KCI807 was administered intraperitoneally (IP) in a volume of 0.2 mL/20 g mouse with the following formulation: 5% DMSO (v/v) with 0.5% NaHCO$_3$ (v/v), in 1% carboxymethylcellulose (CMC). For preliminary dose determinations, mice were given a single dose of the compound daily×3 days, with escalation if no symptoms were noted e.g. 100, 150 and 250 mg/Kg body weight. Mice were then observed for immediate and peri-acute post-injection toxicity by monitoring weight and body condition for 7 days. As the mice were asymptomatic post all doses given, the highest dose range of 250-260 mg/Kg body weight was used for anti-tumor efficacy studies of the compound. Enzalutamide was administered orally by a well-established regimen of 50 mg/kg daily. Male SCID mice were implanted bilaterally SC with 30-50 mg tumor fragments by 12 gauge trocar, and randomly distributed to various treatment and vehicle control groups (5 mice per group). Treatment typically began 3 days post-implant to determine antitumor efficacies and to further evaluate potential cumulative toxicities. Tumors were measured with a caliper 3 times/week and tumor masses (in mg) estimated by the formula, mg=(a×b2)/2, where "a" and "b" are tumor length and width in mm, respectively. Mice were sacrificed when cumulative tumor burdens reached 5-10% of body weight (1-2 g) in the control group. In a parallel experiment, groups of 5 mice were administered KCI807 as described above but were sacrificed on Days 3, 11 and 19 at 6h following the last injection to monitor plasma levels of unmetabolized KCI807.

Figure 13:
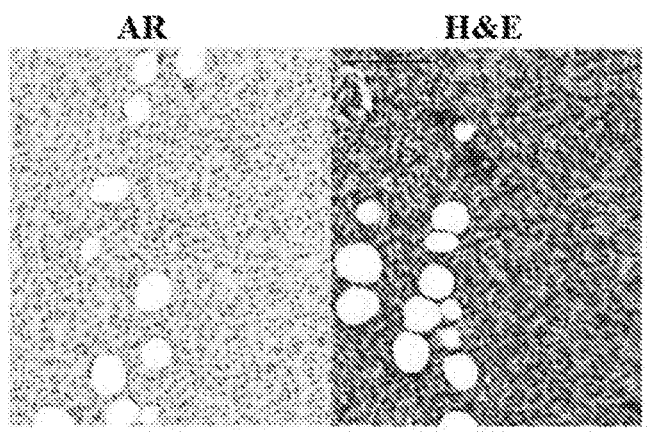
FIG. 13 shows images of a PDX-PR011 tumor from serial passage 8 obtained from the mouse host sectioned and stained by immunohistochemistry (IHC) to detect AR (left panel); or stained with hematoxylin and eosin (right panel).
Figure 12A:
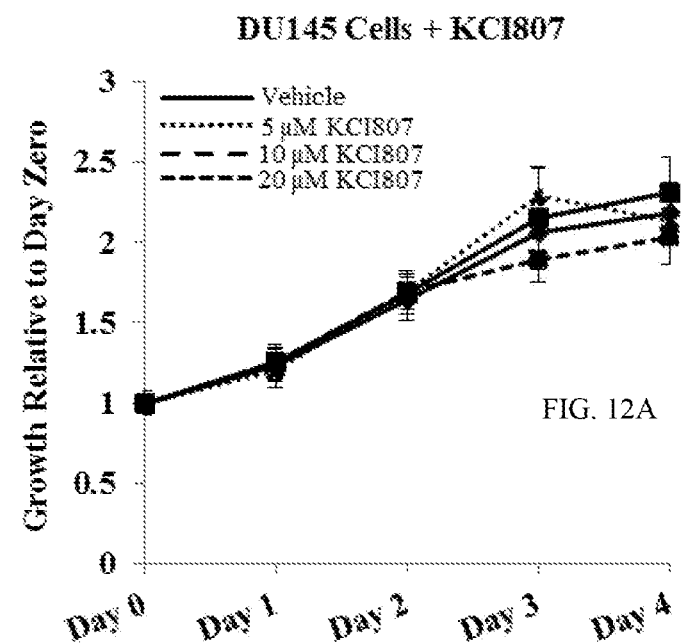
FIG. 12A is a graph showing the effect of KCI807 on in vitro growth of AR-negative cell line Du145 cells measured by the MTT assay. All values were plotted relative to the Day zero value.
Figure 12B:
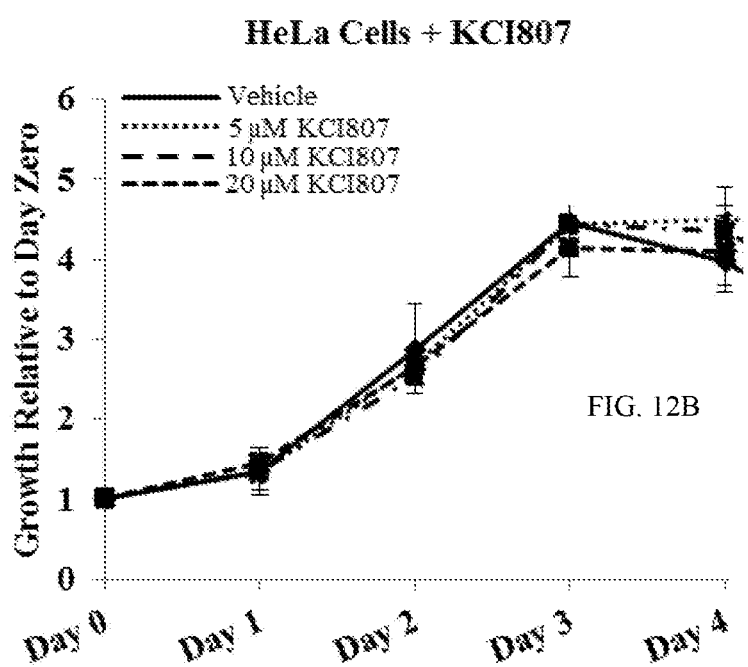
FIG. 12B is a graph showing the effect of KCI807 on in vitro growth of AR-negative cell line HeLa cells measured by the MTT assay. All values were plotted relative to the Day zero value.
Figure 12C:
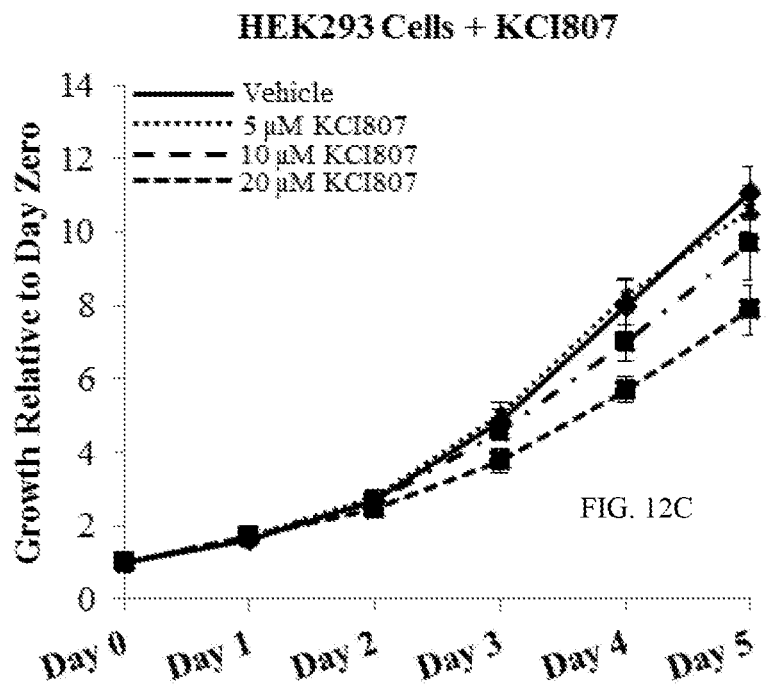
FIG. 12C is a graph showing the effect of KCI807 on in vitro growth of AR-negative cell line HEK293 cells measured by the MTT assay. All values were plotted relative to the Day zero value.
Figure 12D:
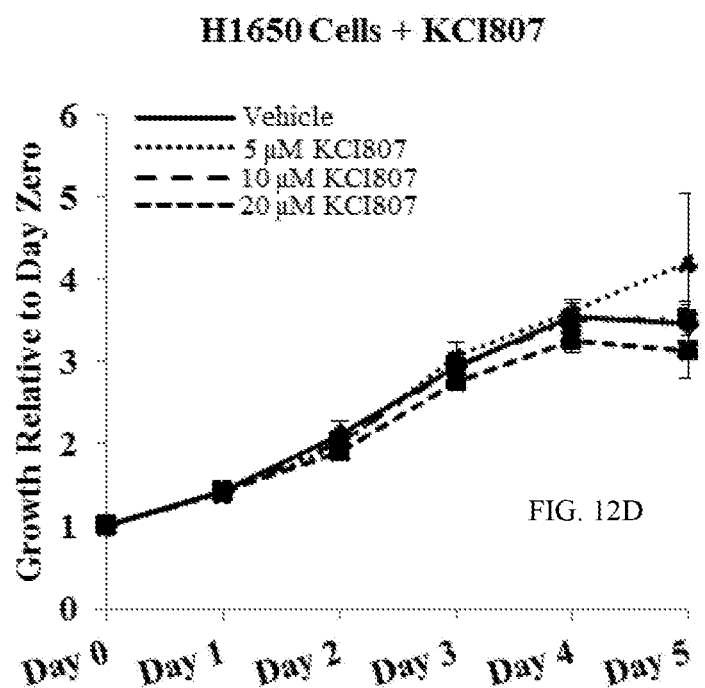
FIG. 12D is a graph showing the effect of KCI807 on in vitro growth of AR-negative cell line H1650 cells measured by the MTT assay. All values were plotted relative to the Day zero value.

PDX-PR011 is a prostate tumor xenograft derived from an initial bone biopsy donated by a CRPC patient at Karmanos Cancer Institute. The biopsy was implanted subcutaneously into a SCID male mouse and ultimately metastasized to the lungs. The metastatic lungs were harvested and implanted into a fresh mouse, which then subsequently formed a subcutaneous tumor. The tumor xenograft retained AR expression (FIG. 13). Tumor implantation in mice, the KCI807 treatment regimen and tumor growth measurements were conducted as described above with the exception that treatment with KCI807 was initiated within 1 day of tumor implantation because of the relatively more aggressive growth rate of the tumors.

Statistical Methods

All of the in vitro experiments were repeated at least three times. The error bars in all graphs represent the standard deviation, unless otherwise stated. Statistical analysis was performed using two-sample t-test or one-way ANOVA with post-hoc LSD (Least Square Differences).

In the gene expression analysis using the mRNA profiling data, the differentially expressed genes were identified using the following cutoff definitions: 2-fold change and unadjusted p-value (by a 2-sided two-sample t-test)<0.05. These genes were analyzed by Venn diagram and the hypergeometric test was used to assess whether the intersection of separately identified genes with elevated expression was statistically significant. The canonical pathway analyses were further carried out for these genes by IPA (Ingenuity Pathway Analysis, http://www.ingenuity.com) with the following parameters: genes only reference set, direct and indirect relationships, experimentally observed confidence, and human species. The detected canonical pathways were statistically tested by a hypergeometric test at a 5% significance level and the ratios of molecules present in the dataset out of all the function related molecules were calculated for each of detected canonical pathways.

In the mouse xenograft studies, a total of 5 mice were used for each of three treatment groups, resulting in a total of 15 mice, and each mouse had two tumors, implanted in their left and right flanks. The tumor growth rates were statistically compared among five treatment groups using a linear mixed-effects model and, in particular, in order to consider flank side-specific variation, the flank side was introduced as another level for each group in addition to the mouse-specific level. Non-zero tumor volumes were log-transformed to meet the normality assumption before linear mixed-effects modeling. The reported p-values were not adjusted for multiple comparisons. The tumor volume curves were depicted by median and an interval of semi-interquartile range on the basis of the raw tumor volume values.

For the drug concentration-time profile, groups of 5 mice were used for each of three time points at Day 3, 11, and 19, resulting in a total of 15 mice, and the measurements of drug concentrations at each time point were repeated 4 times. The comparisons between two time points (Day 3 vs. Day 11 and Day 11 vs. Day 19) were performed using a linear mixed-effects model by considering within- and between-mouse variations. All concentrations were log-transformed before linear mixed-effects modeling and the p-values were adjusted by Bonferroni correction. The drug concentration-time profile was depicted by median and an interval of semi-interquartile range on the basis of the raw concentration values.

Results

Screening of Test Compounds

For the primary screen, recombinant AR+HeLa cells harboring 1) a TATA-dependent promoter-luciferase reporter gene expression construct including 5 contiguous Gal4 DNA binding domain recognition sequences in operable linkage with a nucleic acid sequence encoding the reporter; 2) an expression construct encoding a fusion protein, the fusion protein including a Gal4 DNA binding domain and ELK1 lacking an ETS DNA binding domain wherein the Gal4 DNA binding domain is substituted for the ETS DNA binding domain of ELK1; and 3) an expression construct encoding human androgen receptor (AR); wherein the DNA binding domain of the DNA binding domain-ELK1 fusion protein specifically binds to the DNA binding domain recognition sequence of the reporter gene expression construct were used. When these cells are treated with testosterone, AR translocates to the nucleus where it binds to the Gal4-ELK1 fusion protein and activates the reporter gene. The cells for counter screening were identical to the primary screening cells with the exception that an androgen response element (ARE) sequence replaced the 5 contiguous Gal4 DNA binding domain recognition sequences in the promoter of the reporter gene and Gal4-ELK1 was absent. Compounds of interest should only suppress the signal in the primary screening assay, as the only difference between these two assays is AR recruitment to the promoter via ELK1 binding vs. direct DNA binding. (Illustrative schematic in FIGS. 6A and 6B). The Z-factor for the primary screening assay was 0.734 and for the counter screening assay it was 0.711. In both assays enzalutamide, which does not allow nuclear translocation of AR, completely suppressed the signal (FIGS. 7A, 7B) and hence served as the positive control for the screening assays.

Two pilot sets of compound libraries, LOPAC and Prestwick, and then the Maybridge Hit Finder library, which is a diversity set, were screened at a compound concentration of 10 μM. A hit in the primary screen was defined as a compound able to reduce luciferase reporter activity ≥3 standard deviations below the negative control or to a level ≥40% of the enzalutamide control. This definition produced 1613 hits. Elimination of false positives by counter-screening resulted in 92 compounds with variable potencies (40%-100% inhibition) in the primary screen. The compound 5,7,3',4'-tetrahydroxyflavone (Hit1) was selected for further testing based on its potency of inhibition in the primary screen (80%-100% in <6 hours) and virtual absence of an effect in the counter screen (FIG. 1A).

Figure 1C:
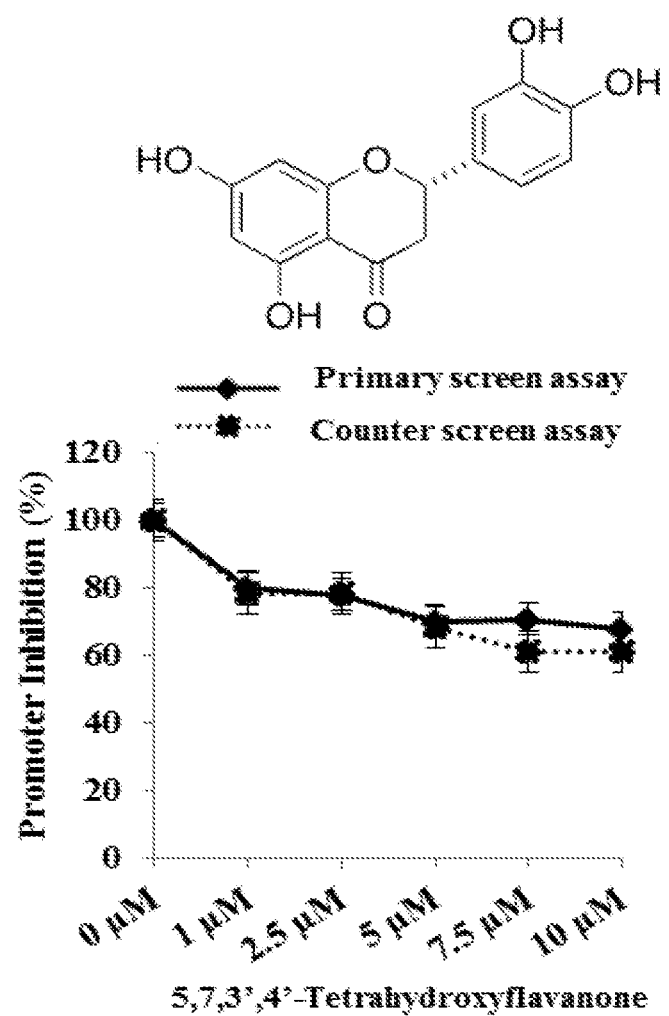
FIG. 1C shows the chemical structure of 5,7,3',4'-tetrahydroxyflavanone and a graph showing a dose response curve for 5,7,3',4'-tetrahydroxyflavanone for inhibition of promoter activation by testosterone in the primary screening assay (ELK1-dependent promoter activation by AR) compared with the counter screening assay (ARE-dependent promoter activation by AR). The cells were simultaneously treated with compound and testosterone for 6h and promoter activity was measured as reporter luciferase activity.

The essential structural elements required for selective activity against the ELK1-AR complex were identified by structure-activity analysis using the same in vitro assay as in the primary screening. First, the effect of substituting the flavone scaffold in Hit 1 was tested with the closely related flavanone and isoflavone scaffolds. Hit 1 was unable to affect either ELK1-dependent or ARE-dependent promoter activation by AR upon scaffold substitution (FIGS. 1B, 1C). Further structure-activity analysis using derivatives of Hit 1 in which individual or combinatorial substitution of hydroxyl groups were substituted by hydrogen indicated that, in the A ring, only the hydroxyl group at the 5 position is necessary for activity but by itself it confers weak activity at best (Table 1 in FIG. 19). A second hydroxyl substitution on the B ring enhances activity, optimally at the 3' position and sub-optimally at the 4' position (Table 1 in FIG. 19). Simultaneous substitution of all four hydroxyl groups with methoxy groups or substitution at the 3' position alone with a methoxy group abolished activity (Table 1 in FIG. 19). Further, methoxy substitutions on carbons at positions 4', 6 and 7 were moderately tolerated although the derivatives had sub-optimal activity (Table 1 in FIG. 19). Finally, methoxy substitution on the carbon at position 3 was not tolerated (Table 1 in FIG. 19), predicting possible steric hindrance from any bulky substitutions at this position.

To test the relative stability of 5,3'-dihydroxyflavone, the intracellular concentrations of 5,3'-dihydroxyflavone, 5,3', 4'-trihydroxyflavone and 5,7,3',4'-tetrahydroxyflavone (Hit 1) were compared following incubation at a media concentration of 2 uM compound. The intracellular concentration of 5,3'-dihydroxyflavone was unchanged between 1h and 6h in contrast to the tri- and tetra-hydroxy compounds whose concentrations rapidly declined during this period, indicating that removal of hydroxyl groups at the 7 and 4' positions in Hit 1 conferred stability without compromising effectiveness against the target.

Figure 8:
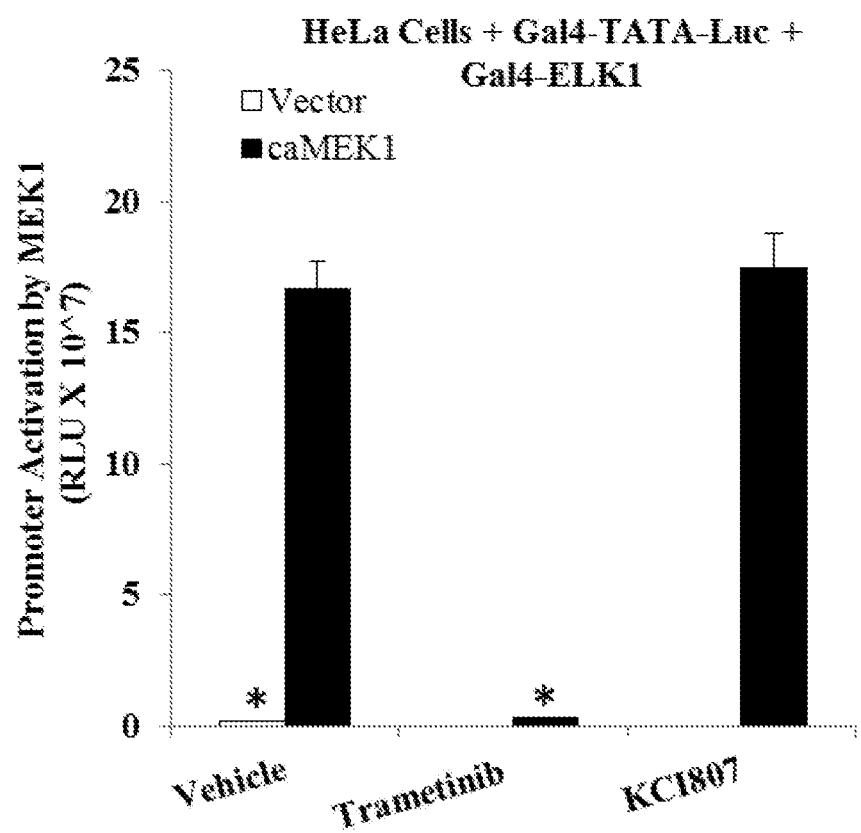
FIG. 8 is a graph showing results of co-transfection of HeLa cells with the Gal4-TATA-Luc construct and the expression plasmid for the Gal4-ELK1 fusion protein. In addition the cells were transfected with an expression plasmid for a constitutively active MEK1 protein (caMEK1). The cells were then treated with the MEK1 inhibitor, trametinib (1 μM), KCI807 (20 μM), or vehicle (DMSO). Cells were harvested 48h post transfection and luciferase activity was measured. In all panels, the error bars represent standard deviation of experimental triplicates. *P<0.001

As a secondary test of target selectivity, the effect of 5,3'-dihydroxyflavone on activation of ELK1 by MEK/ERK was examined using HeLa cells co-transfected with the Gal4-TATA-Luc construct, the expression plasmid for the Gal4-ELK1 fusion protein and either an expression plasmid for a constitutively active MEK1 protein (caMEK1) or vector control. Activation of the luciferase reporter by MEK1 was completely inhibited by the MEK inhibitor trametinib but 5,3'-dihydroxyflavone did not inhibit the promoter activation (FIG. 8).

The compound 5,3'-dihydroxyflavone (also called KCI807 herein) was identified as stable, bioavailable, and fully and selectively active against the target ELK1-AR interaction. The compound 5,3'-dihydroxyflavone is the minimal structure that is fully and selectively active against the target ELK1-AR interaction.

Figure 2A:
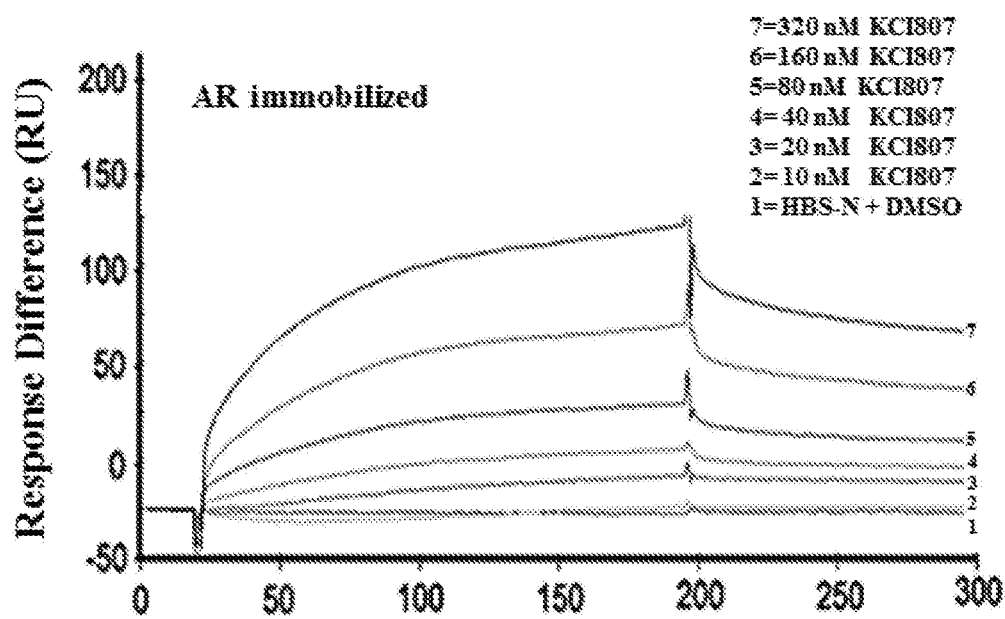
FIGS. 2A, 2B, 2C, 2D, 2E, and 2F illustrate binding of KCI807 to AR and disruption of its binary and chromatin complexes with ELK1.
Figure 2B:
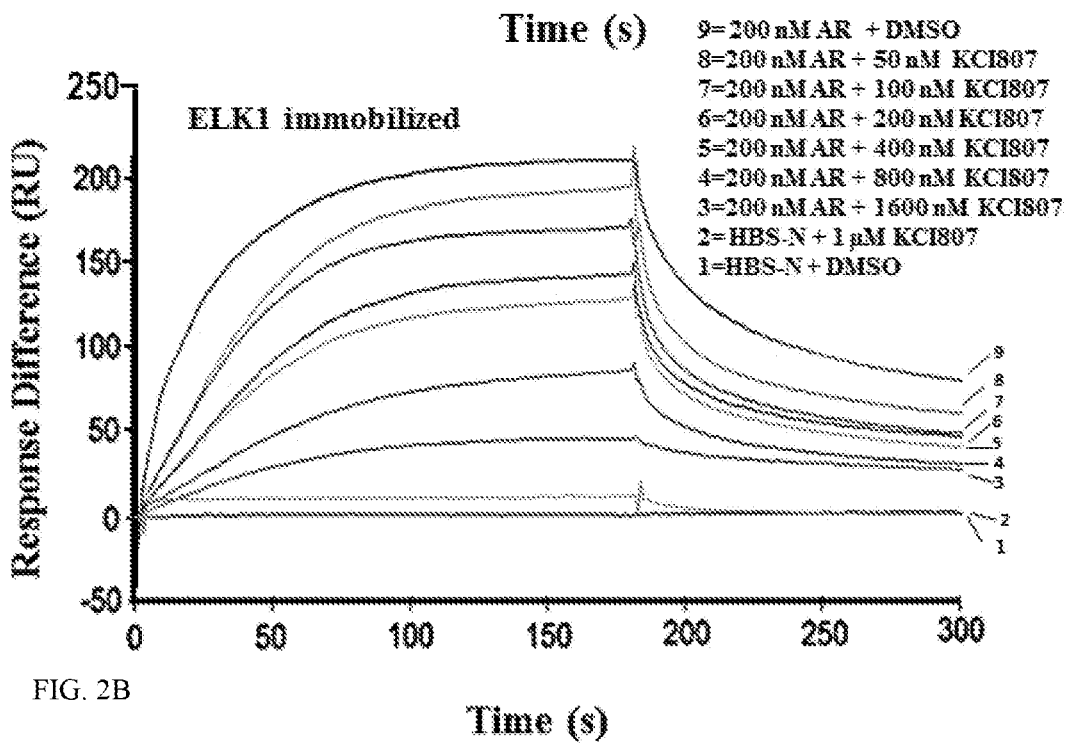
Figure 2C:
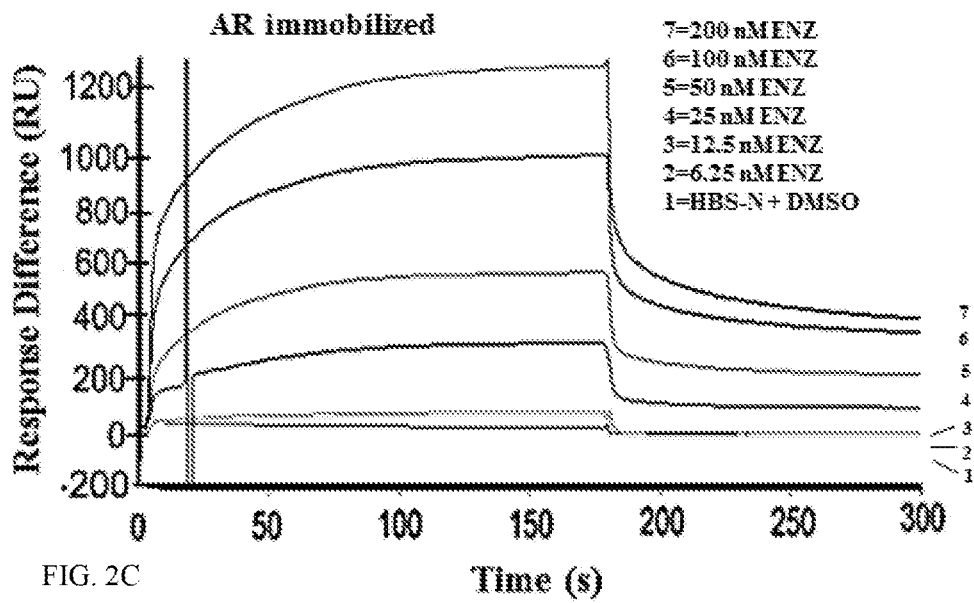
Figure 2D:
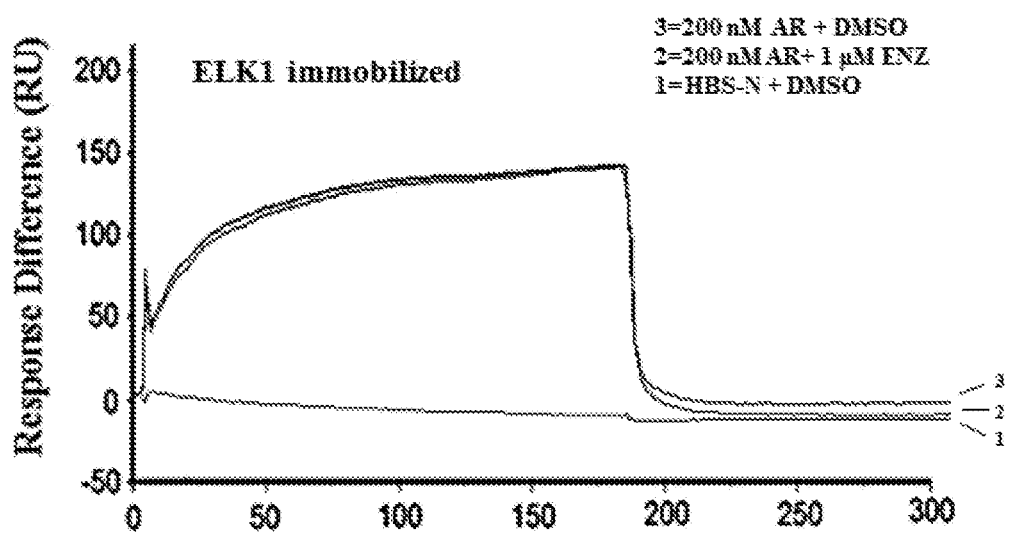
Figure 9B:
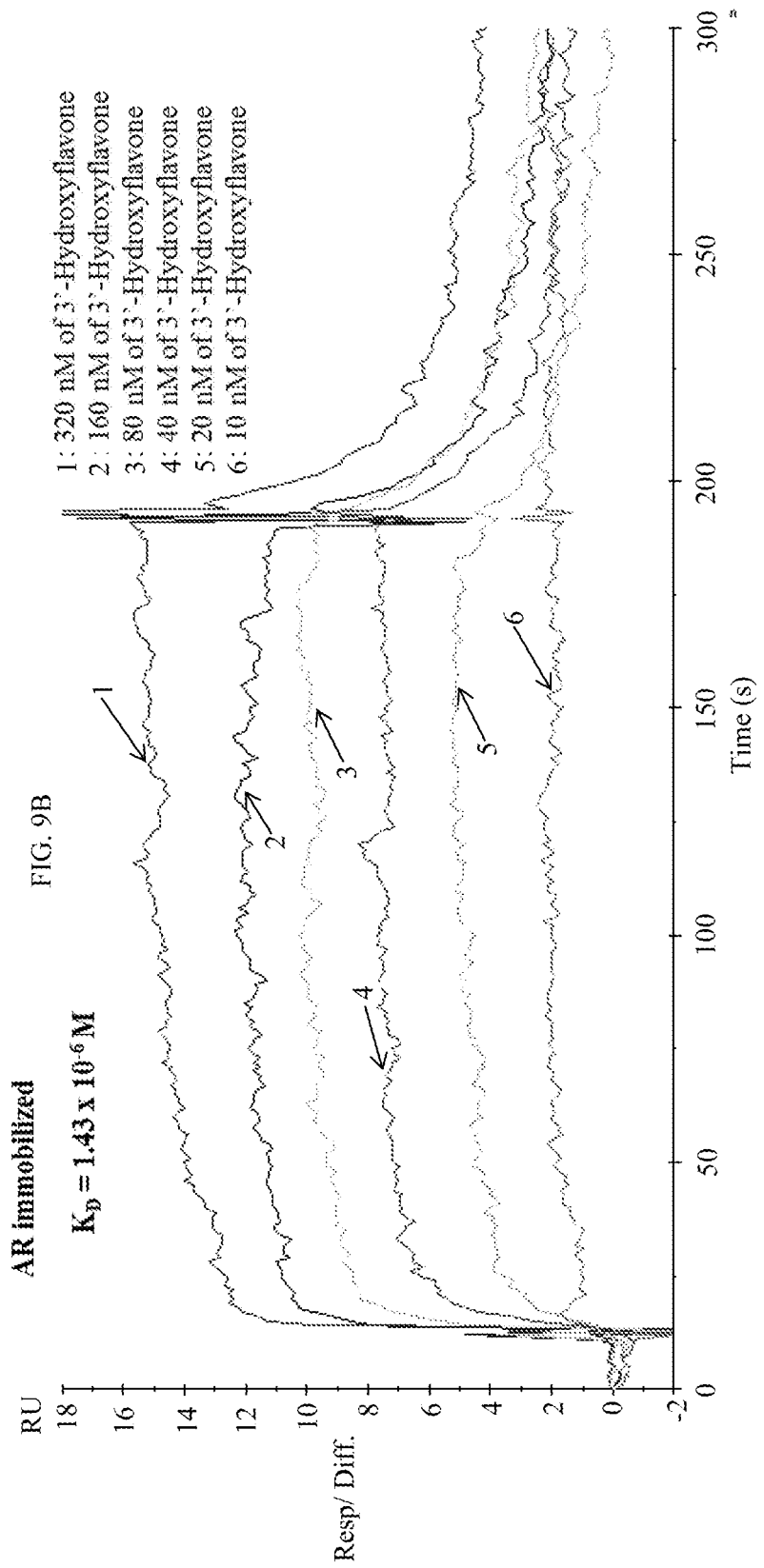
FIG. 9B shows surface plasmon resonance (SPR) kinetic curves for quantitative analyses of compounds binding to AR. AR was immobilized and the 3'-Hydroxyflavone (analyte) was diluted in a series (0, 10, 20, 40, 80, 1600, and 320 nM).

Disruption of the ELK1-AR binary complex and selective inhibition of chromatin recruitment by binding of KCI807 to AR It was determined by surface plasmon resonance (SPR) that KCI807 binds to purified immobilized AR with a dissociation constant of $7 \times 10^{-8}$ M (FIG. 2A). In contrast, KCI807 did not bind to immobilized ELK1 (FIG. 2B). The functional relevance of the binding data is also supported by the fact that the binding of AR to either 5-hydroxyflavone or 3'-hydroxyflavone was extremely weak (with dissociation constants of $5.9 \times 10^{-6}$M and $1.43 \times 10'$M, respectively) (FIGS. 9A and 9B), consistent with their weak or absent activity compared to KCI807 in Table 1. SPR analysis also demonstrated that KCI807 blocked binding of purified AR (used as analyte) to purified immobilized ELK1 progressively with increasing molar ratios relative to AR (FIG. 2B). In contrast, although SPR analysis could demonstrate the binding of enzalutamide to AR with a dissociation constant of $1.7 \times 10^{-9}$ M (FIG. 2C), enzalutamide was unable to block the binding of AR to ELK1 (FIG. 2D).

Figure 2E:
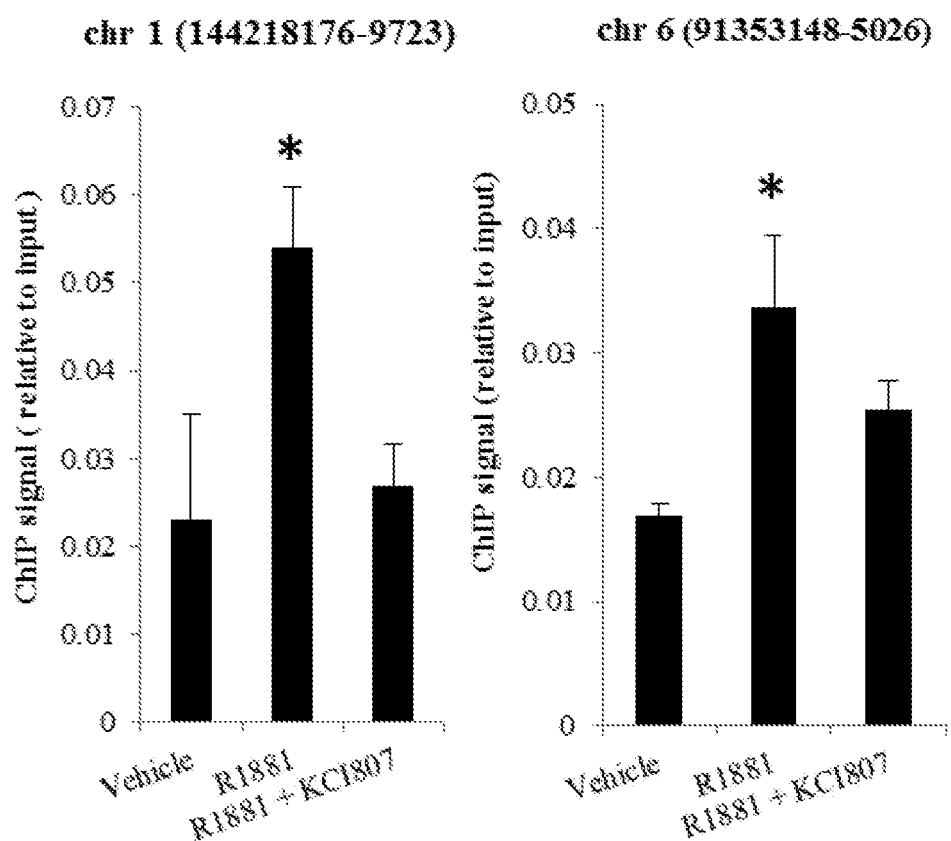
Figure 2F:
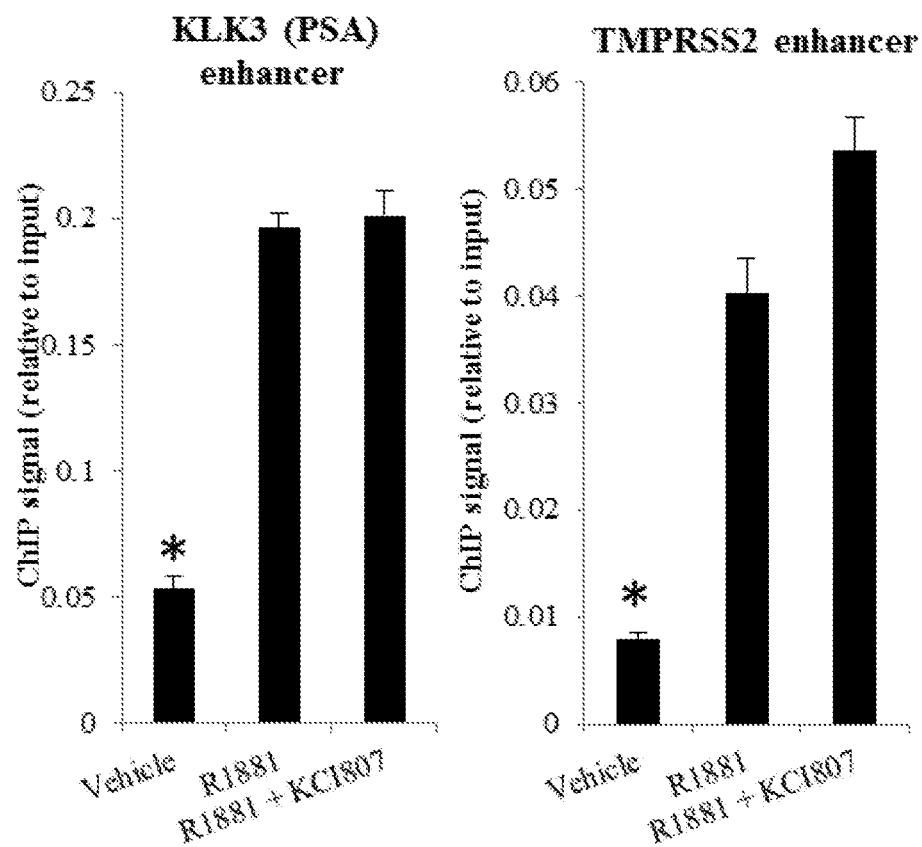

The ability of KCI807 to selectively block recruitment of AR by ELK1 to chromatin in situ was tested. Chromatin immunoprecipitation (ChIP) assays showed that in LNCaP PC cells, KCI807 prevented association of AR with sites in the chromatin at which ELK1 recruits AR (FIG. 2E). In contrast, KCI807 did not affect AR recruitment at the well-established canonical ARE enhancer sites associated with the KLK3 (PSA) and TMPRSS2 genes (FIG. 2F).

The set of complementary results described above establish that KCI807 directly binds to AR and selectively blocks its physical association with ELK1, inhibiting ELK1-dependent transcriptional activity of AR.

Narrow genotropic effects of KCI807 in CRPC cells

Figure 10:
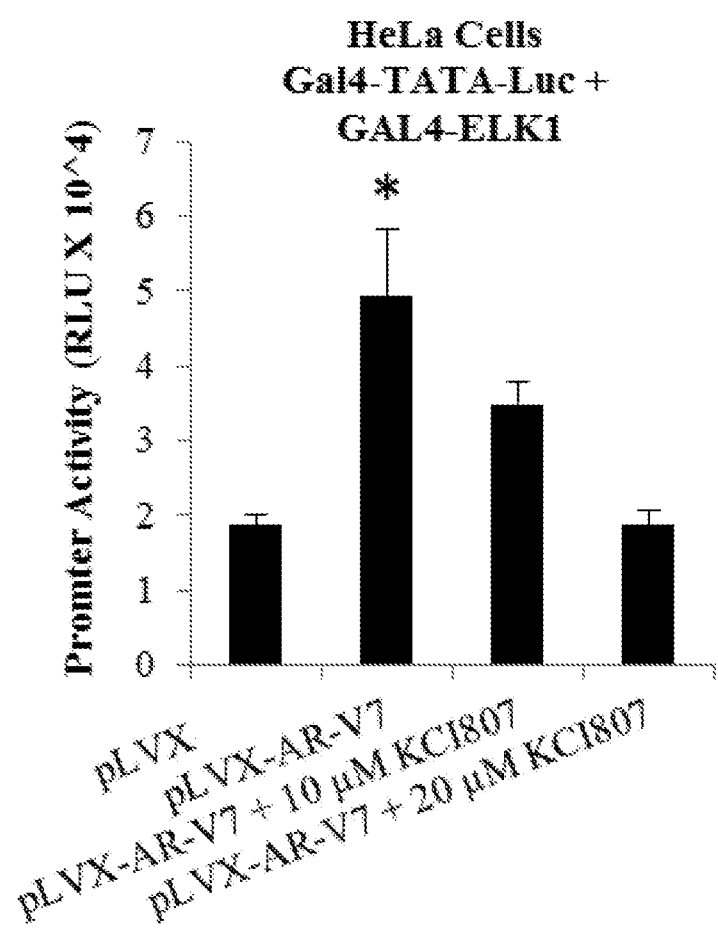
FIG. 10 is a graph showing results of co-transfection of HeLa cells with the Gal4-TATA-Luc construct and the Gal4-ELK1 fusion protein expression plasmid. The cells were also co-transfected with either the AR-V7 expression plasmid (pLVX-AR-V7) or the corresponding vector plasmid (pLVX). At the time of transfection with AR-V7, the cells were also treated with KCI807 (10 uM or 20 uM) or with the vehicle control. Promoter activity was measured in terms of reporter luciferase activity. In all panels, the error bars represent standard deviation of experimental triplicates. *P<0.05

KCI807 also inhibited hormone-independent promoter activation by the splice variant AR-V7 (FIG. 10). The relatively higher concentrations of the compound required for this inhibition is likely because AR-V7 was overexpressed in the assay system.

Figure 3A:
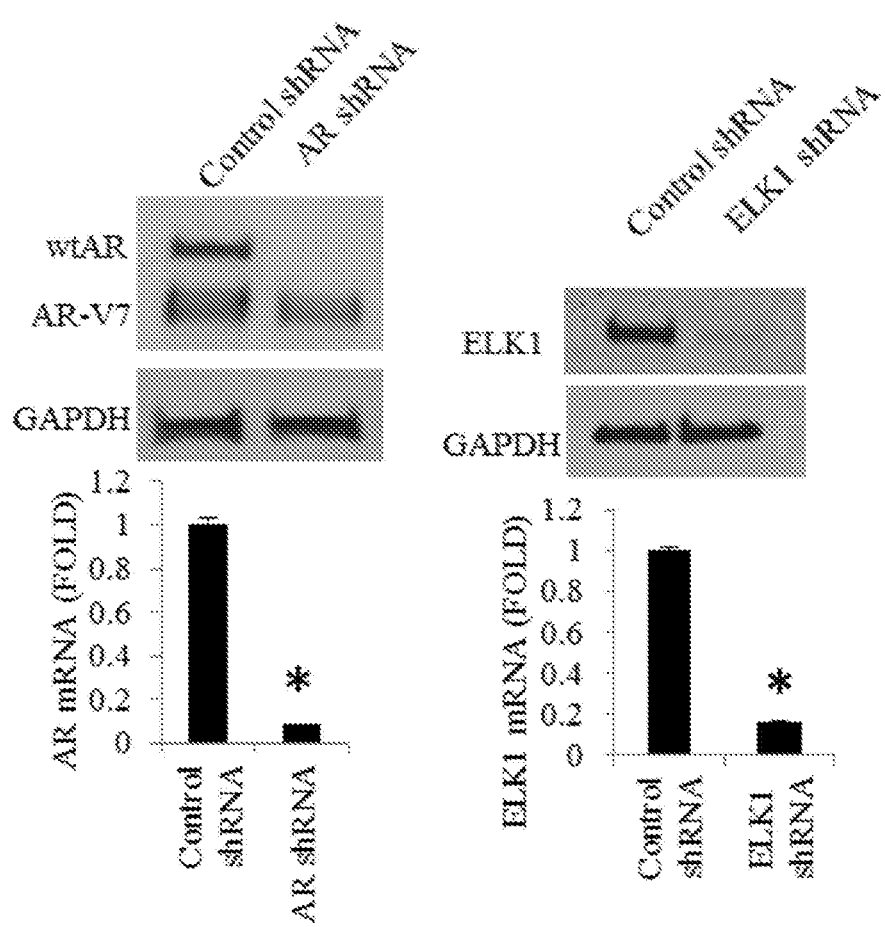
FIGS. 3A, 3B, 3C, 3D, and 3E relate to identification of transcriptional targets of KCI807.
Figure 3B:
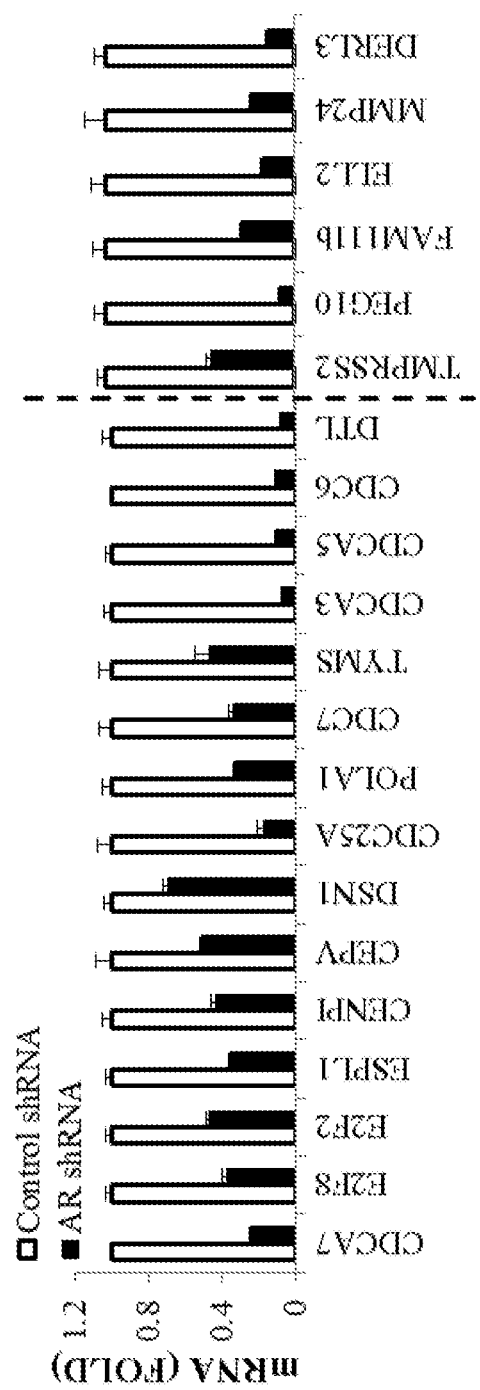
Figure 3C:
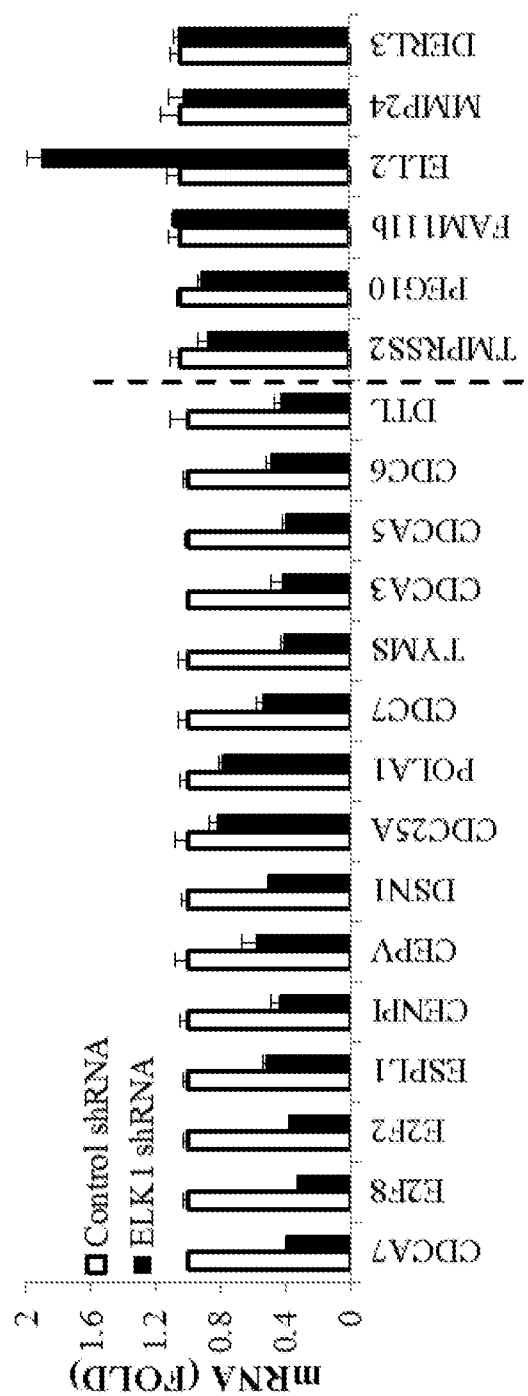
Figure 3D:
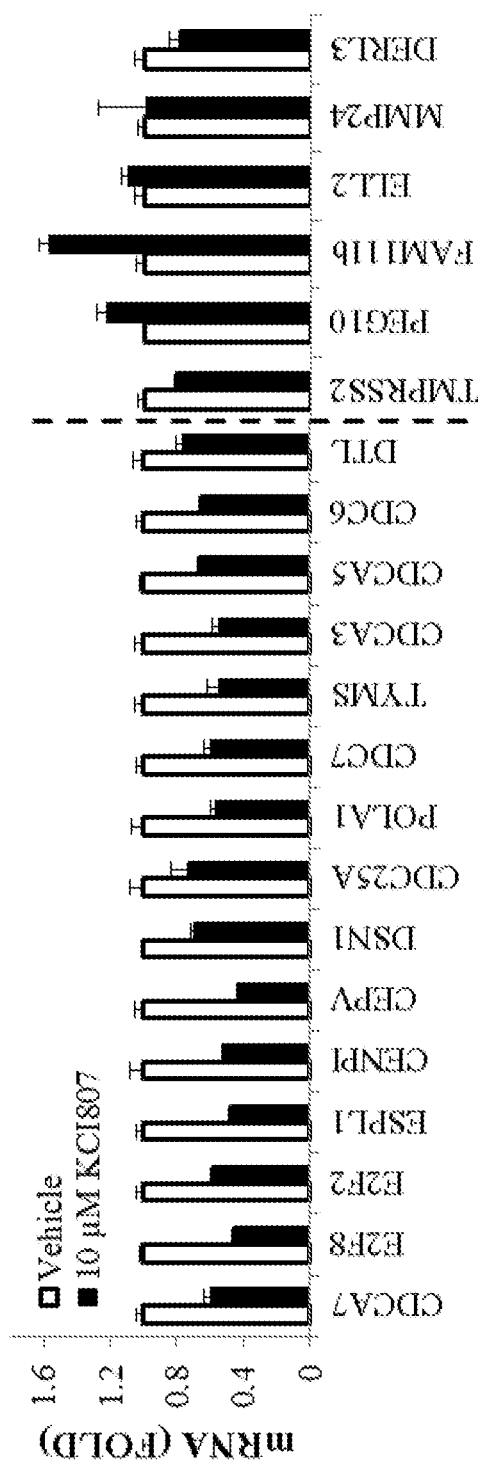

To test the selectivity of KCI807 for ELK1-dependent gene activation by AR vs. other target genes of the receptor, 22Rv1 CRPC cells, which are dependent on both full length AR and AR-V7 for hormone-independent growth, were used. In these cells, depletion of full length AR using lentiviral shRNA (FIG. 3A, left panels) led to reduction in mRNA levels of representative AR target genes previously (24) shown to be activated by AR in either an ELK1-dependent manner (FIG. 3B, genes left of dashed line) or ELK1-independent manner (FIG. 3B, genes right of dashed line). Depletion of ELK1 using lentiviral shRNA (FIG. 3A, right panels) caused reduction only in the mRNAs for genes previously reported to be ELK1-dependent for regulation by AR (FIG. 3C, genes left of dashed line). Treatment of the cells with KCI807 decreased expression of only the genes known to be supported synergistically by ELK1 and AR (FIG. 3D, genes left of dashed line).

Figure 3E:
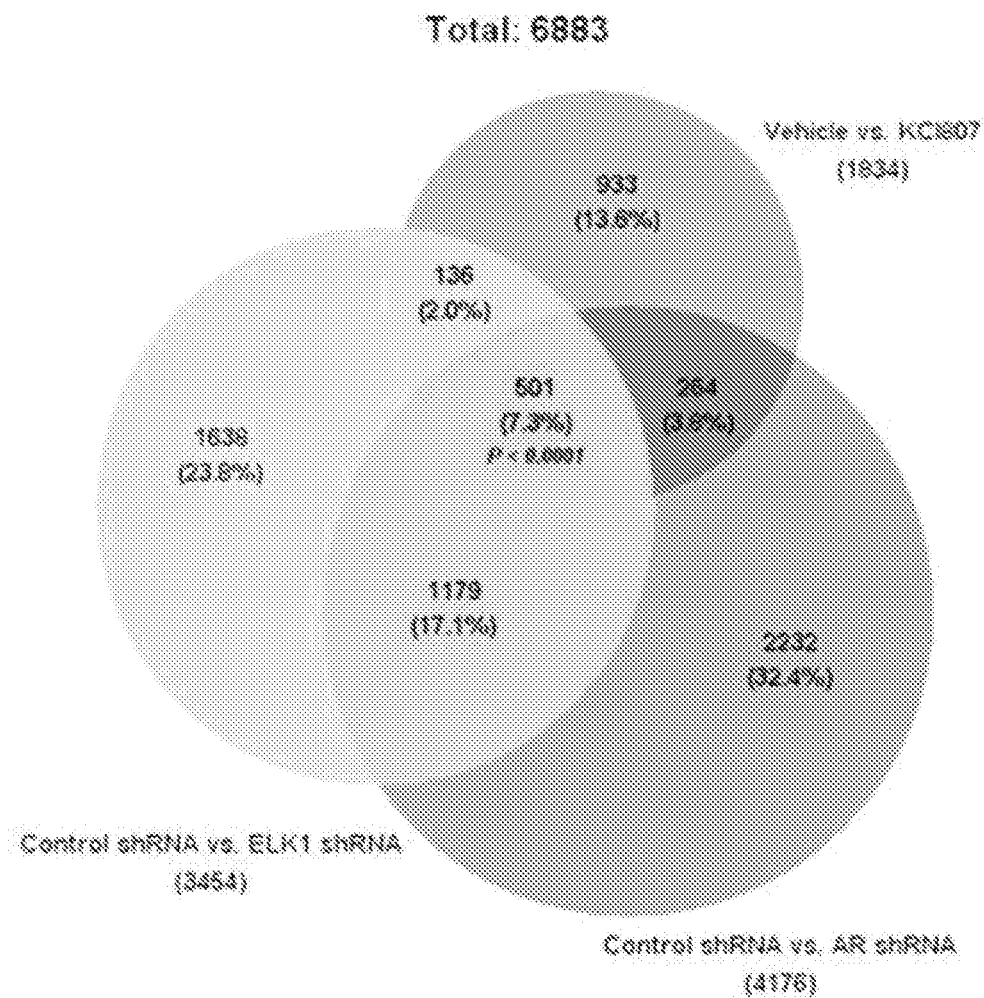

To examine the global genotropic effects of KCI807 in 22Rv1 cells, Affymetrix DNA microarray analysis was used for comparative transcriptome profiling of decreases in mRNA levels due to drug treatment, depletion of AR or depletion of ELK1 (Venn diagram in FIG. 3E. AR was at least partially dependent on ELK1 for activation of about a third of its target genes and these genes were functionally strongly and primarily enriched for cell cycle progression and mitosis. The AR-ELK1 activated genes inhibited by KCI807 were similarly primarily enriched for cell proliferation genes although the compound did affect a smaller subset of ELK1-independent AR target genes with weak functional clusters possibly by interfering with binding of AR to one or more unidentified tethering proteins. The limited number of genes affected by KCI807 that were not activated by AR did not show ontological clustering of high significance.

These genotropic effect results comprehensively demonstrate that the target gene set of KCI807 is principally associated with functional roles in cell cycle progression and mitosis within the AR signaling axis, and this functional clustering is virtually exclusively associated with synergistic activation by ELK1 and AR.

Selective in vitro growth inhibition by KCI807 and comparison with enzalutamide

Figure 4A:
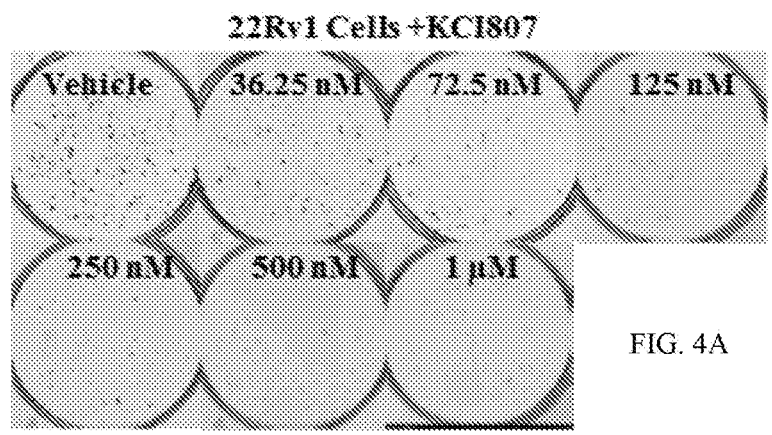
FIGS. 4A, 4B, 4C, 4D, 4E, 4F, 4G, and 4H relate to inhibition of AR-dependent PC/CRPC clonogenic survival and cell growth by KCI807 and comparison with enzalutamide.
Figure 4B:
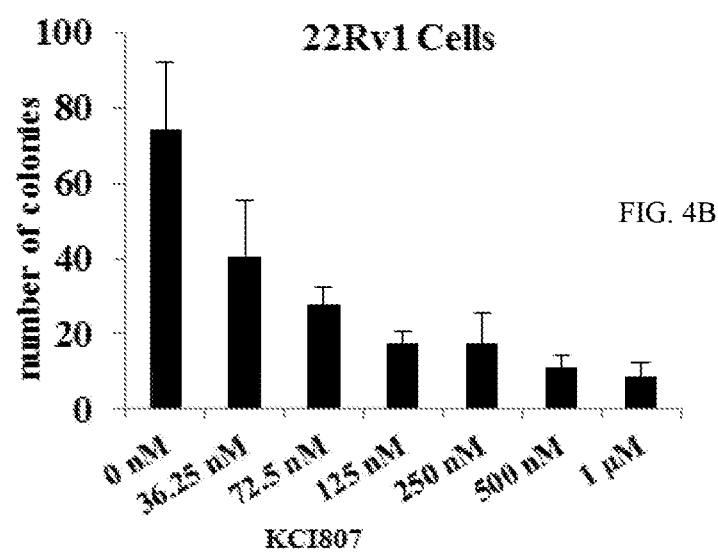
Figure 4C:
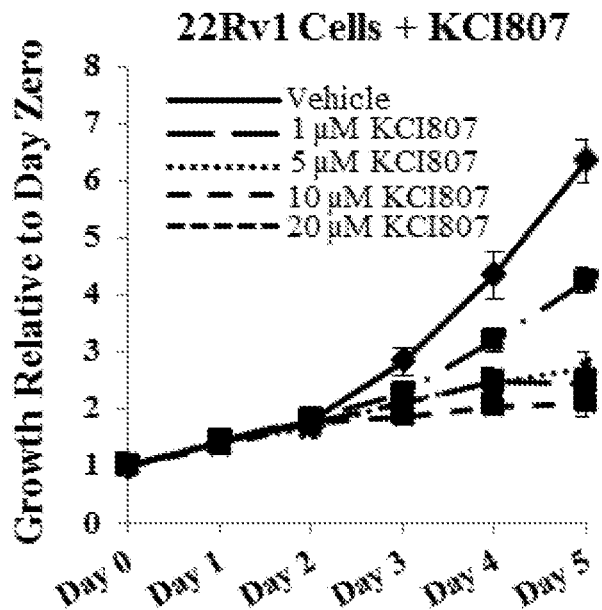
Figure 4D:
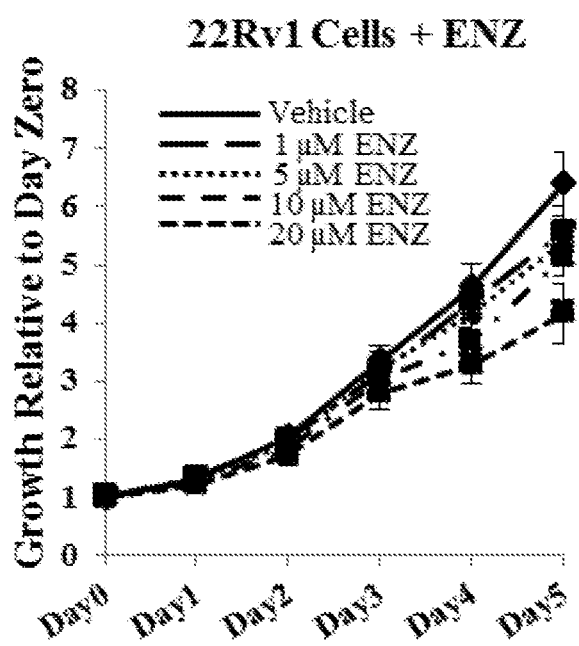
Figure 4E:
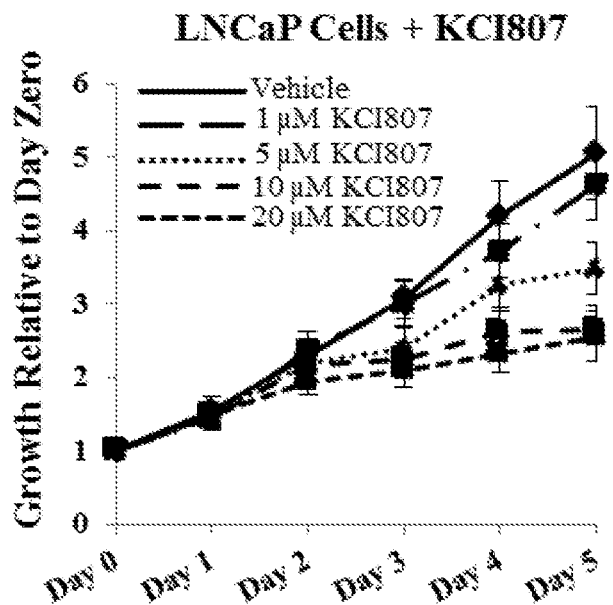
Figure 4F:
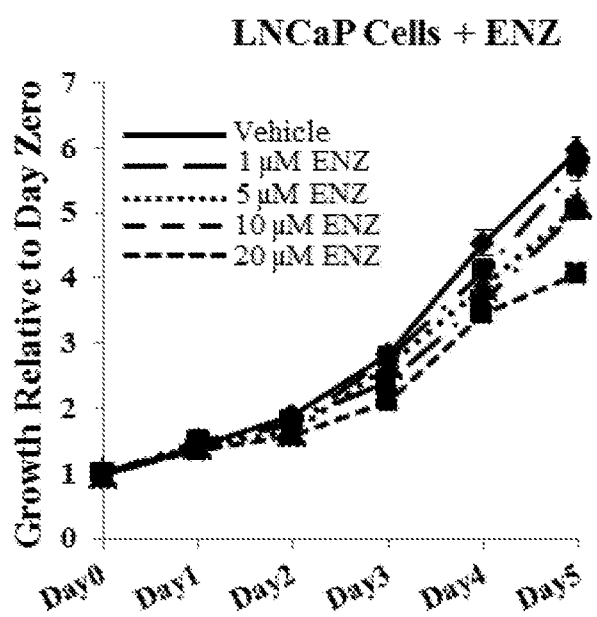
Figure 4G:
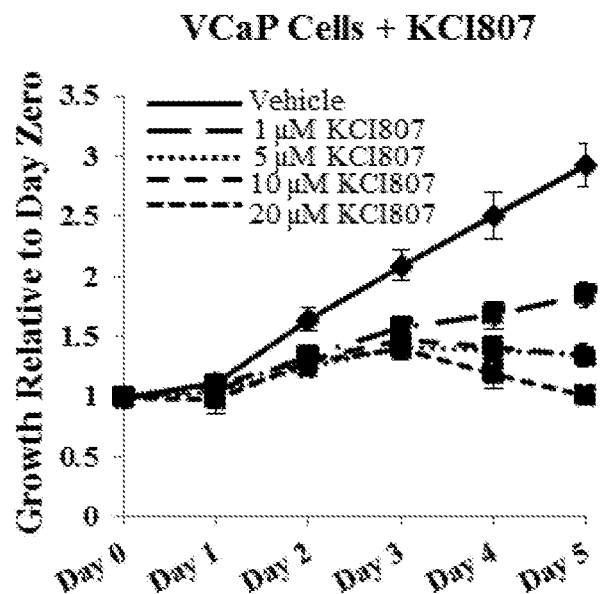
Figure 4H:
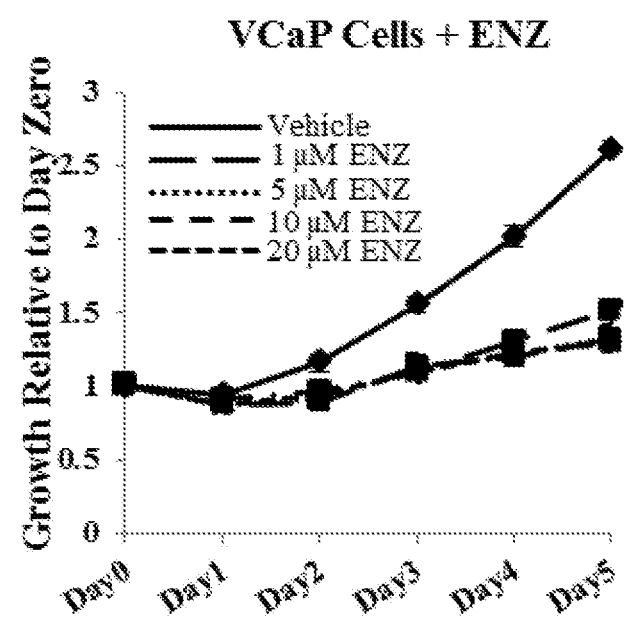
Figure 11:
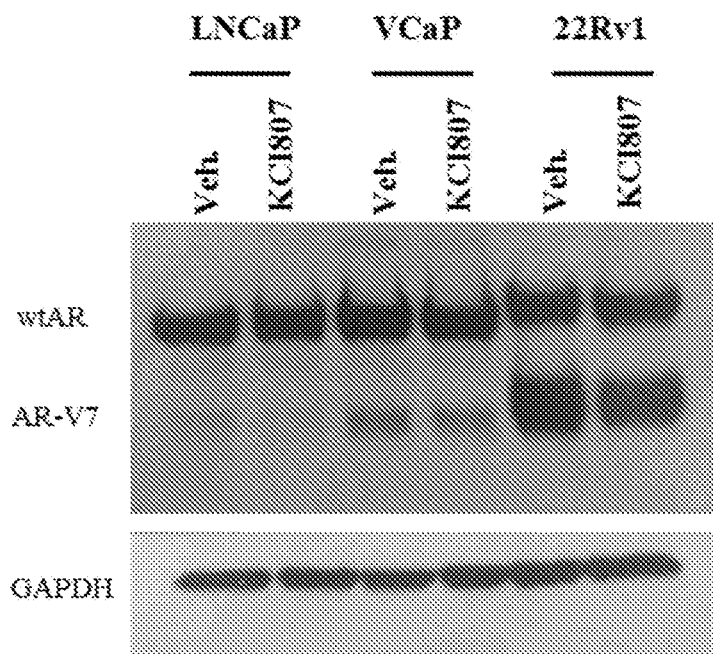
FIG. 11 shows images of Western blots using proteins from LNCaP, VCaP, and 22Rv1 cells treated with vehicle or KCI807 (10 µM). Protein lysates were extracted after 24h of treatment and probed using antibodies to AR and GAPDH (loading control).

KCI807 inhibited both androgen-dependent and androgen-independent in vitro growth of standard AR-dependent PC/CRPC cell line models. After initiation of colony formation of the enzalutamide-resistant 22Rv1 CRPC cells, further colony growth was virtually completely inhibited by KCI807 beyond 125 nM compound, with an $IC_{50}$ of 33.12 nM (FIGS. 4A and 4B). With respect to dose response of the cell growth inhibition by the MTT viability assay, KCI807 was more effective than enzalutamide 22Rv1 (androgen-independent cells) (FIGS. 4C and 4D) and LNCaP (androgen-dependent cells) (FIGS. 4E and 4F) cells; moreover, in these cell lines KCI807 completely inhibited cell growth whereas enzalutamide only showed partial effects even at a concentration of 20 uM (FIGS. 4C, 4D, 4E, and 4F). VCaP cells (androgen-dependent) were the most sensitive to KCI807 as well as enzalutamide at comparable doses (FIGS. 4G and 4H). Among the above PC/CRPC cell lines, in no case did KCI807 treatment alter the protein level of AR or AR-V7 (FIG. 11). KCI807 did not appreciably affect the growth of AR-negative cell lines including DU145 (prostate cancer cells), HeLa (cervical cancer cells), HEK293 (adenovirus transformed kidney fibroblasts) and H1650 (lung adenocarcinoma cells), FIGS. 12A, 12B, 12C, and 12D, respectively. The growth inhibitory effect of KCI807 is thus selective for PC cells that are dependent on AR and/or AR-V7. Further, this compound shows a better growth inhibitory profile than enzalutamide in well-established prostate cancer cell line models without decreasing the expression level of AR or AR-V7.

Suppression of CRPC growth in vivo by KCI807

The in vivo anti-tumor efficacy of KCI807 was tested using two types of model tumor xenografts in male SCID mice. The first was generated from the enzalutamide-resistant 22Rv1 CRPC cell line and the second was a patient-derived tumor from an enzalutamide-resistant bone metastatic CRPC (patient-derived tumor xenograft, PDX-PR011). The tumors were xenografted on day zero.

In the case of the 22Rv1 CRPC xenograft model, treatment was initiated on day 3 (representing early stage disease where implanted tumors have established blood flow) when either KCI807 was administered intraperitoneally (IP) at a dose of 250-300 mg/kg, every other day or enzalutamide was given orally (PO) at 50-60 mg/Kg, daily on a standard regimen. The standard regimen for administration of enzalutamide is described in detail in Zhan Y, et al. Int. J. Cancer, 2013, 133(9):2225-33.

Figure 5A:
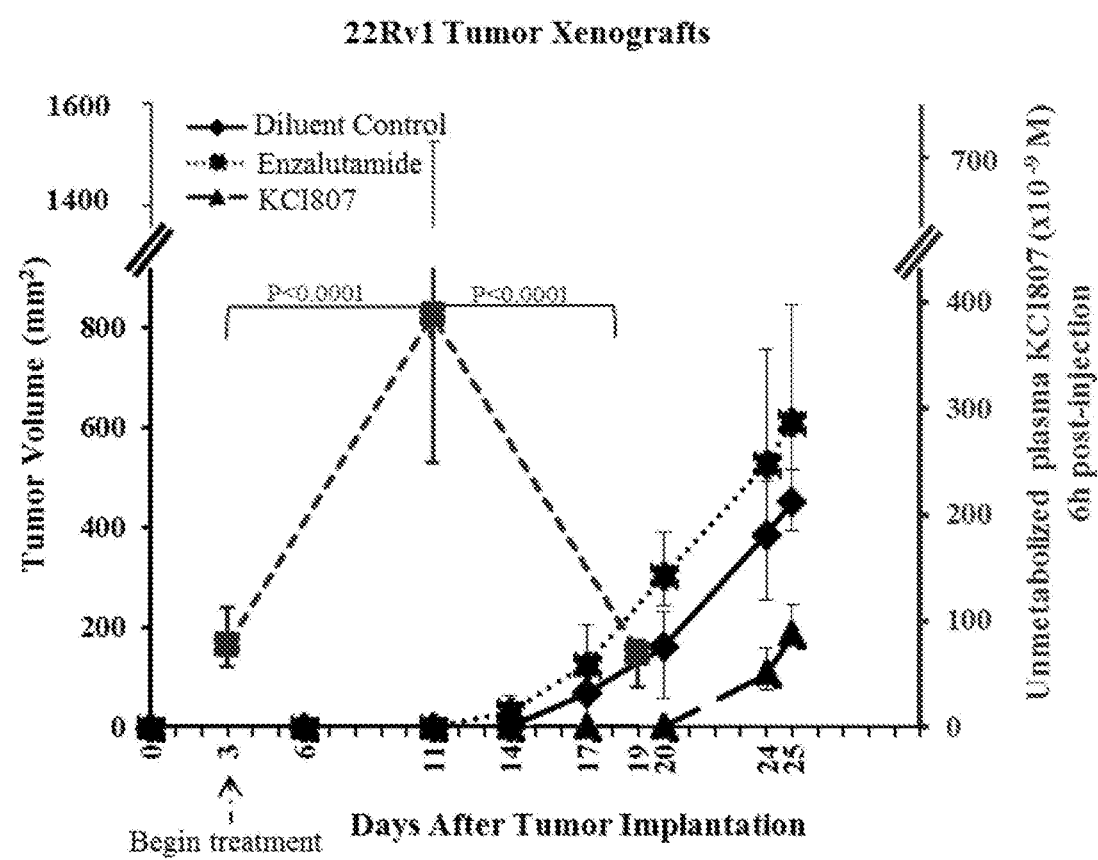
FIGS. 5A and 5B relate to inhibition of in vivo CRPC tumor growth by KCI807.

The experiment was terminated when the tumor burden in the placebo group reached 5-10% of body weight. Tumor growth was inhibited by KCI807 but not by enzalutamide (FIG. 5A). A delayed recovery of tumor growth in mice treated with KCI807 followed a sharp decline in plasma level of unmetabolized compound (median $70\times10^{-9}$M on Day 19, compared to $3.87\times10^{-7}$M on Day 11) suggesting self-induced enhancement of clearance rate of the compound in the rodent model during the chronic dosing schedule of the compound. The major plasma metabolites of KCI807 comprised glucuronidation and other modifications at the 3' position The mice treated with KCI807 were asymptomatic for the duration of the study and did not show appreciable weight loss, see Table 5.

TABLE 5

| | Days After Tumor Implantation | | | | | | | |
|---|---|---|---|---|---|---|---|---|
| | 0 | 6 | 11 | 14 | 17 | 20 | 24 | 25 |
| Diluent Control % body weight lost/gained | 0 | +2.8 | +4.6 | +1.9 | +3.7 | +4.6 | +3.7 | +3.7 |
| Enzalutamide % body weight lost/gained | 0 | +3.7 | +5.5 | +3.7 | +4.6 | +4.6 | +4.6 | +3.7 |
| KCI807 % body weight lost/gained | 0 | −1.87 | +.09 | 0 | 0 | +2.7 | +3.5 | +2.7 |

Figure 5B:
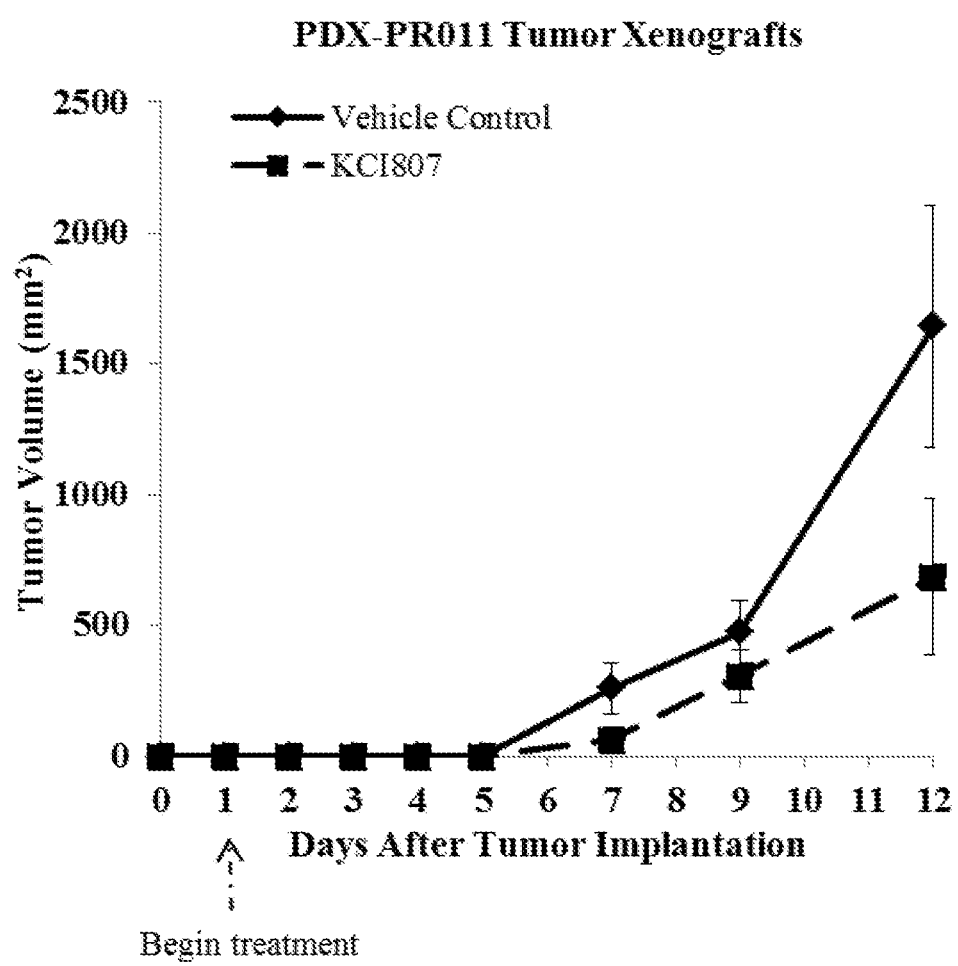
Figure 14:
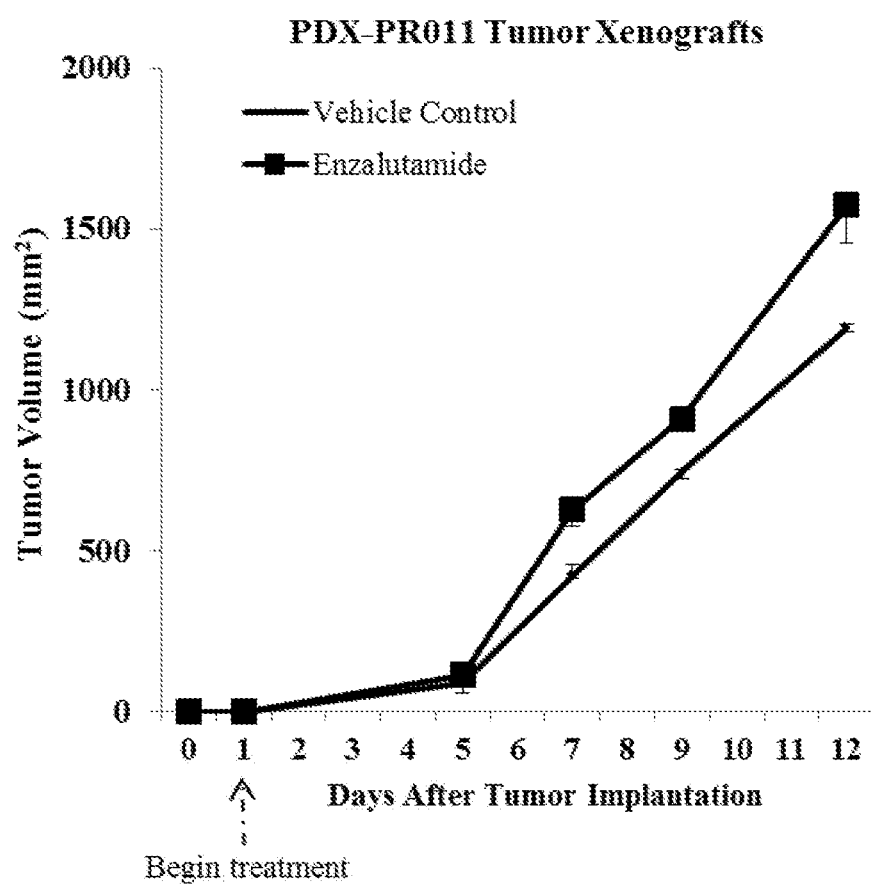
FIG. 14 is a graph showing results obtained when PDX-PR011 tumor xenografts were implanted sc into male SCID mice in both flanks. The vehicle control and Enzalutamide were administered following the standard regimen of daily oral administration of 50 mg/Kg. Treatment was begun on Day 1 after tumor implantation. Tumor volume curves are plotted as median and an interval of semi-interquartile range on the basis of their raw values.

In the case of the patient-derived PDX-PR011 tumor xenograft, treatment was initiated one day after tumor implantation because of the extremely aggressive growth of this tumor, which required termination of the experiment within 12 days due to the heavy tumor burden in the control mice. Despite such aggressive tumor growth and despite the self-induced clearance of KCI807 in rodents noted above, tumor growth was significantly inhibited by KCI807 (FIG. 5B). PDX-PR011 tumor growth was not inhibited by vehicle control or by enzalutamide (FIG. 14). Again, the treated mice were asymptomatic and did not show appreciable weight loss, see Table 6.

5,3'-dihydroxyflavone by chemical group substitution can decrease its rate of metabolism, while retaining its ability to inhibit growth of prostate cancer cells. In this case, a methyl

TABLE 6

| | Days After Turner Implant | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Diluent Control % body weight lost/gained | 0 | −1.5 | −3.8 | −1.5 | −0.8 | 0 | +0.8 | +0.8 | +3.1 | +2.3 | +3.8 | +5.3 |
| KCI807 % body weight lost/gained | 0 | −3.8 | −4.6 | −2.3 | −2.3 | −1.5 | 0 | −1.5 | +0.8 | +0.8 | +1.5 | +3.1 |

Estrogen Receptor-Positive Breast Cancer

Figure 17A:
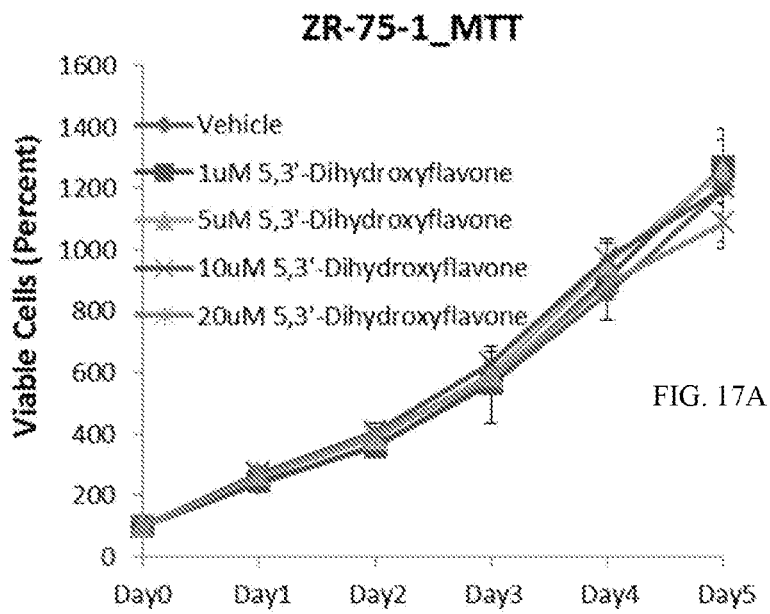
FIG. 17A is a graph showing the effect on growth of various concentrations of 5,3'-Dihydroxyflavone on breast cancer cell line ZR-75-1 using the MTT assay.
Figure 17B:
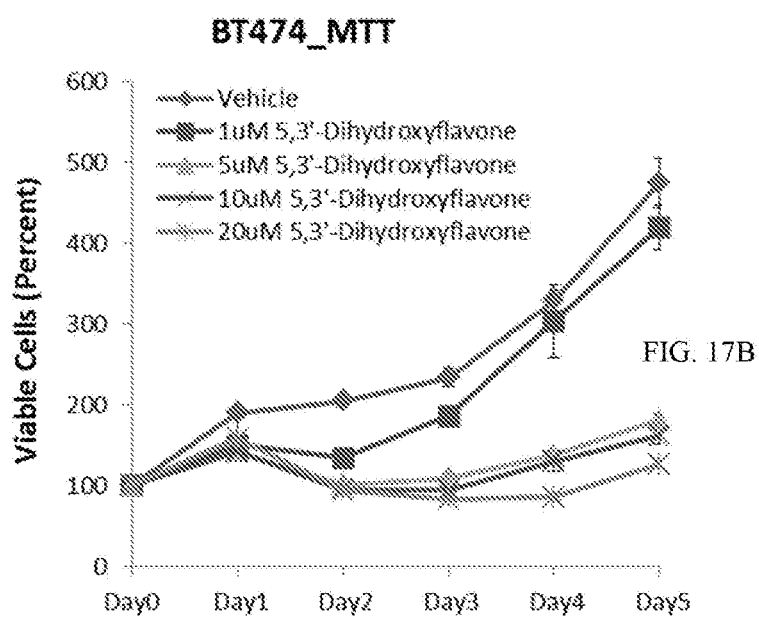
FIG. 17B is a graph showing the growth inhibitory effect of various concentrations of 5,3'-Dihydroxyflavone on breast cancer cell line BT474 using the MTT assay.
Figure 17C:
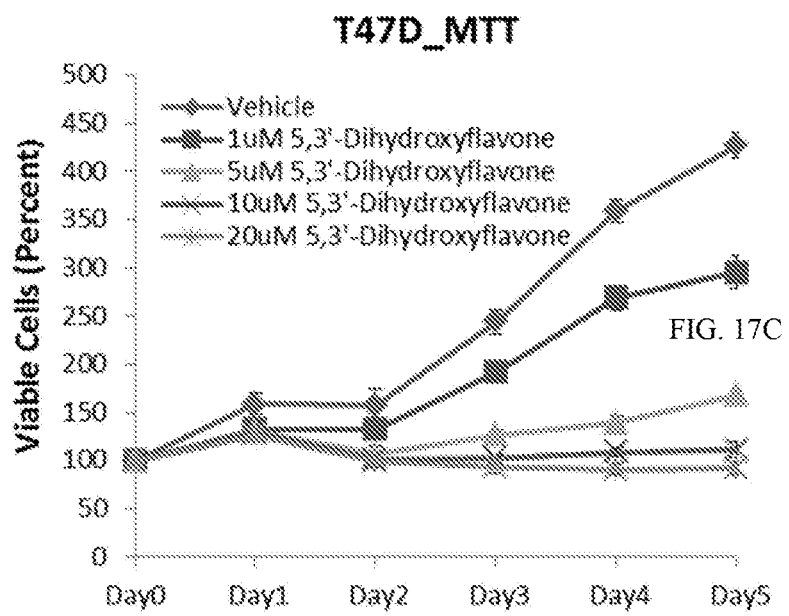
FIG. 17C is a graph showing the growth inhibitory effect of various concentrations of 5,3'-Dihydroxyflavone on breast cancer cell line T47Dusing the MTT assay.
Figure 17D:
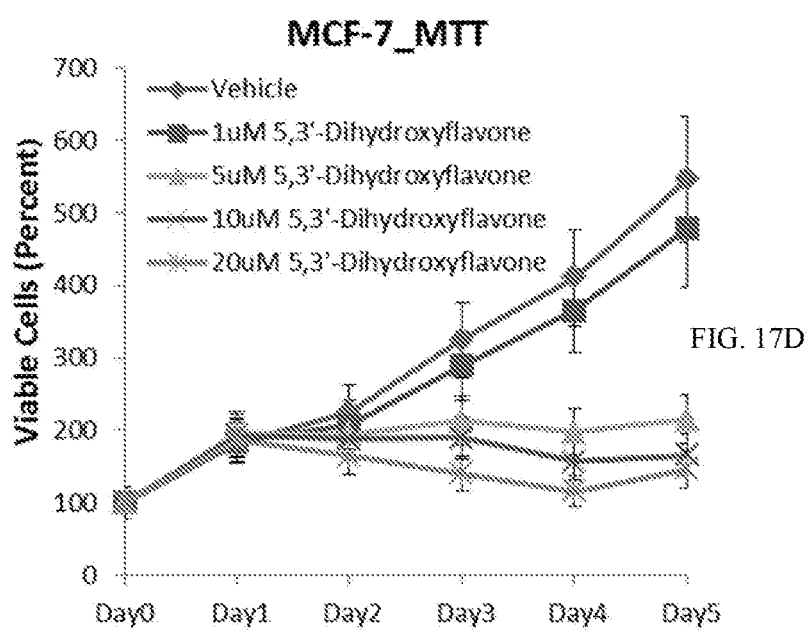
FIG. 17D is a graph showing the growth inhibitory effect of various concentrations of 5,3'-Dihydroxyflavone on breast cancer cell line MCF-7 using the MTT assay.

The growth inhibitory effect of 5,3'-Dihydroxyflavone was tested in breast cancer cell lines using the MTT assay. Twenty four hours after plating the cells, they were treated with the indicated concentrations of the compound. FIG. 17A shows results in ZR-75-1 Cells+5,3'-Dihydroxyflavone; FIG. 17B shows results in BT474 Cells+5,3'-Dihydroxyflavone; FIG. 17C shows results in T47D Cells+5,3'-Dihydroxyflavone; and FIG. 17D shows results in MCF-7Cells+5,3'-Dihydroxyflavone. 5,3'-Dihydroxyflavone is growth inhibitory in vitro in BT474, T47D and MCF-7 cells, which are all dependent on estrogen and ER for growth. The compound did not inhibit the growth of ZR-75-1 cells, which may grow in standard culture media, independent of estrogen and ER. The data suggests that 5,3'-dihydroxyflavone inhibits breast cancer cell growth by disrupting estrogen signaling.

Figure 18:
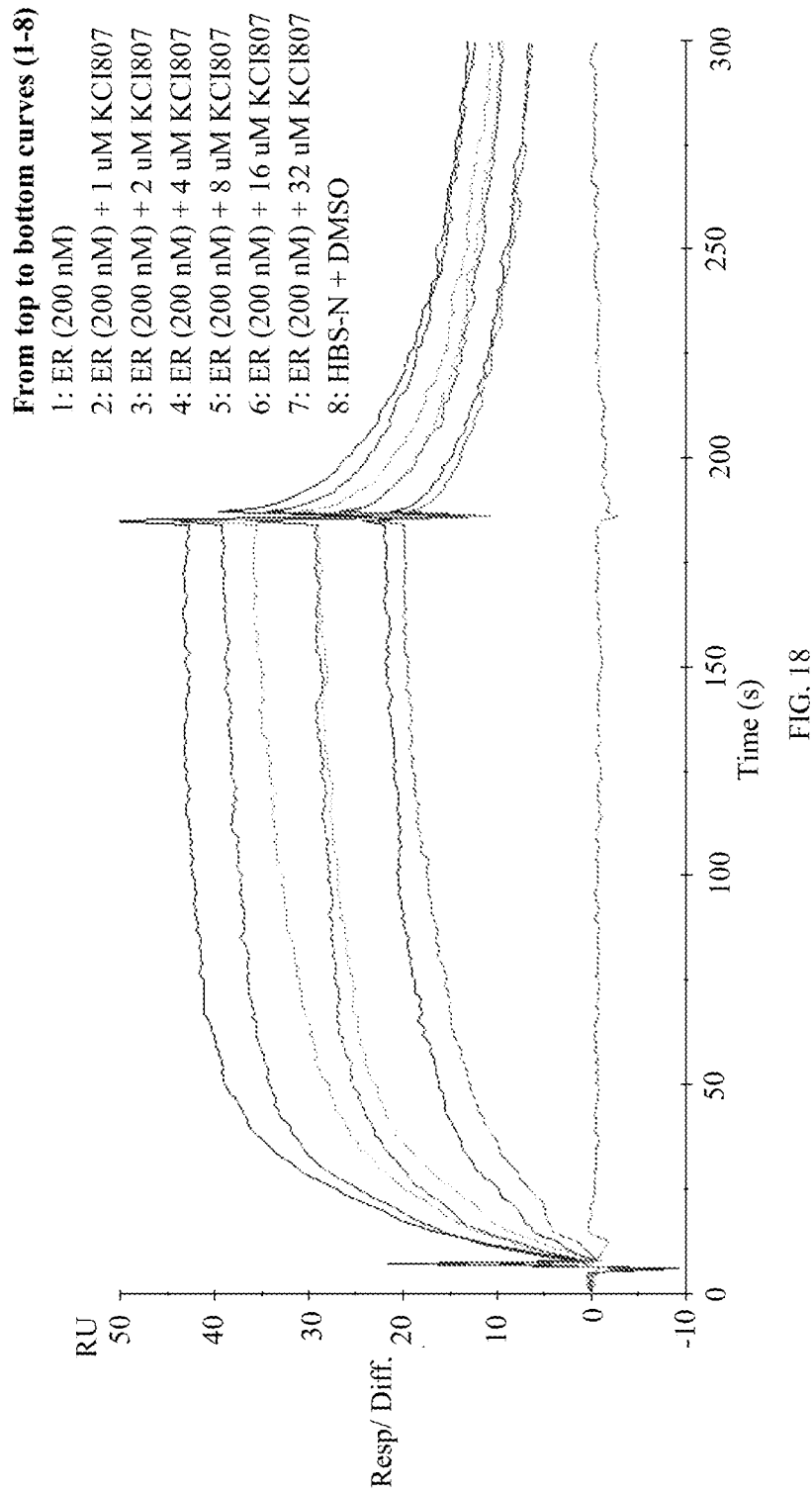
FIG. 18 shows SPR kinetic curves for quantitative analysis of inhibition of binding of ER (used as analyte) to immobilized ELK1 by 5,3'-Dihydroxyflavone. A fixed concentration of ER (200 nM) was combined with 5,3'-Dihydroxyflavone diluted in a series (0, 1, 2,4, 8, 16, and 32 uM). 5,3'-Dihydroxyflavone inhibits the binding of ER to ELK1.

FIG. 18 shows SPR kinetic curves for quantitative analysis of inhibition of binding of ER (used as analyte) to immobilized ELK1 by 5,3'-Dihydroxyflavone. A fixed concentration of ER (200 nM) was combined with 5,3'-Dihydroxyflavone diluted in a series (0, 1, 2, 4, 8, 16, and 32 uM). 5,3'-Dihydroxyflavone inhibits the binding of ER to ELK1. This explains the ability of the compound to inhibit the estrogen-dependent growth of breast cancer cells, as ELK1 is required for estrogen-dependent growth of breast cancer cells.

Derivatives

Metabolism of 5,3'-Dihydroxyflavone and 5,3-Dihydroxy-4'-methylflavone.

BD UltraPool human liver microsomes (HLM) 150 and the NAPDH regenerating system solution A and B were obtained from Corning Inc. Pooled HLM were used to determine percentage of metabolism of 5,3'-Dihydroxyflavone and 5,3-Dihydroxy-4'-methylflavone. The compounds (20 μM) were co-incubated with HLM (0.05 mg/ml) in the presence or absence of NAPDH for 30 minutes in a 37° C. water bath. At the end of the microsome reaction, the reaction was quenched with 1000 μl ethyl acetate. The mixture was vortexed and centrifuged at 13,000 rpm for 15 minutes, the supernatant was then subjected to high-performance liquid chromatography with tandem mass spectrometry (LC-MS/NIS) analysis.

Figure 15:
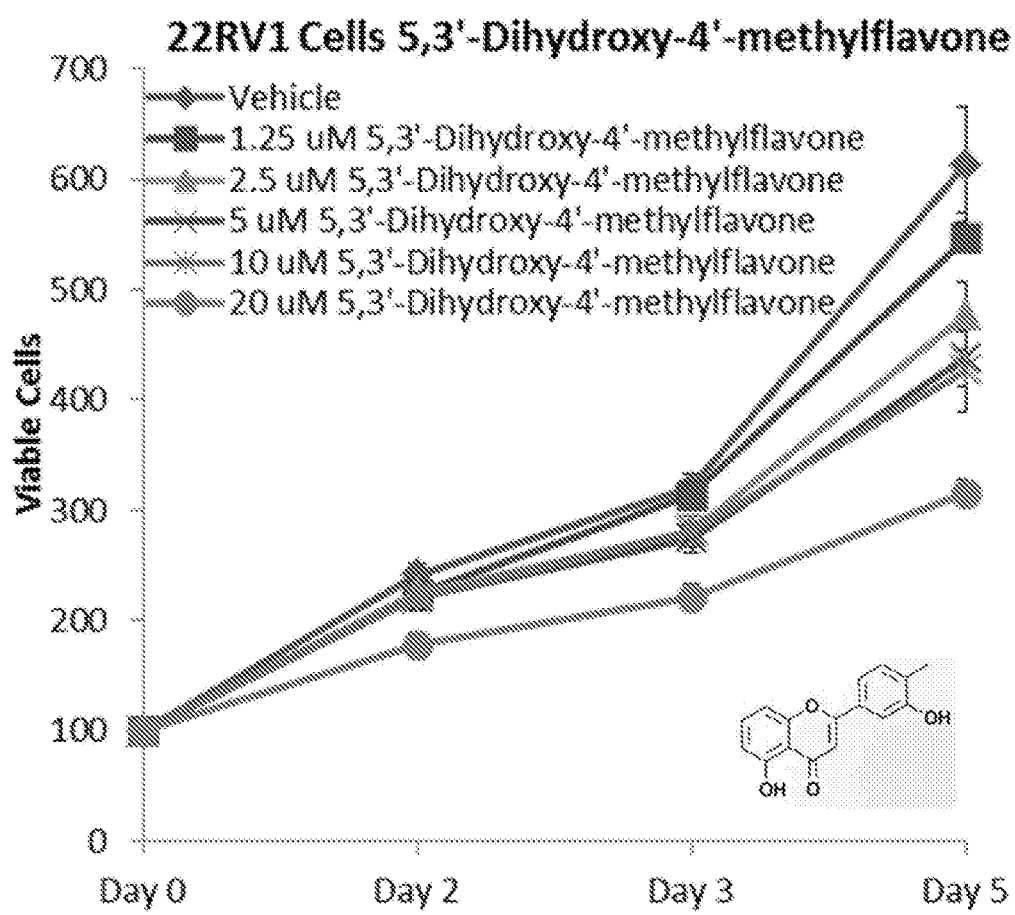
FIG. 15 is a graph showing the growth inhibitory effect of 5,3'-dihydroxy-4'-methylflavone (shown in the inset) on 22RV1 cells using the MTT assay. Twenty four hours after plating the cells, they were treated with the indicated concentrations of the compound.

FIG. 15 is a graph showing the growth inhibitory effect of 5,3'-Dihydroxy-4'-methyflavone was tested using 22RV1 cells and the MTT assay. Twenty four hours after plating the cells, they were treated with the indicated concentrations of the compound. This is an illustration that modification of group substitution on the 4' carbon, which reduced metabolism in human liver microsomes by 50%, still retained its ability to inhibit growth of 22Rv1 cells, as shown in FIG. 15.

The data in Table 7 shows that methyl substitution on C4' in KCI807 will decrease the rate of liver metabolism of the compound.

TABLE 7

| | umol/L | mean | percentage metabolized (%) |
|---|---|---|---|
| KCI807 | | | |
| Control #1 | 0.973 | 0.986 | 19.4 |
| Control #2 | 0.981 | | |
| Control #3 | 1.006 | | |
| NADPH treated #1 | 0.863 | 0.795 | |
| NADPH treated #2 | 0.796 | | |
| NADPH treated #3 | 0.725 | | |
| 4'-methyl-5,3'-dihydroxyflavone | | | |
| Control #1 | 1.789 | 1.774 | 12.7 |
| Control #1 | 1.770 | | |
| Control #2 | 1.757 | | |
| Control #2 | 1.773 | | |
| Control #3 | 1.776 | | |
| Control #3 | 1.782 | | |
| NADPH treated #1 | 1.491 | 1.549 | |
| NADPH treated #1 | 1.513 | | |
| NADPH treated #2 | 1.639 | | |
| NADPH treated #2 | 1.651 | | |
| NADPH treated #3 | 1.498 | | |
| NADPH treated #3 | 1.501 | | |

Derivatives of 5,3'-Dihydroxyflavone, fluorinated at meta-positions relative to hydroxylated carbons (i.e., at C7, C5' or both). Compounds 7-Fluoro-5,3'-dihydroxyflavone and 5',7-diflouro-5,3'-dihydroxyflavone inhibited both ELK1-dependent and ARE-dependent promoter activity and were toxic to AR negative cell lines at low doses (i.e., in the concentration range of 1 uM-10 uM).

Figure 16A:
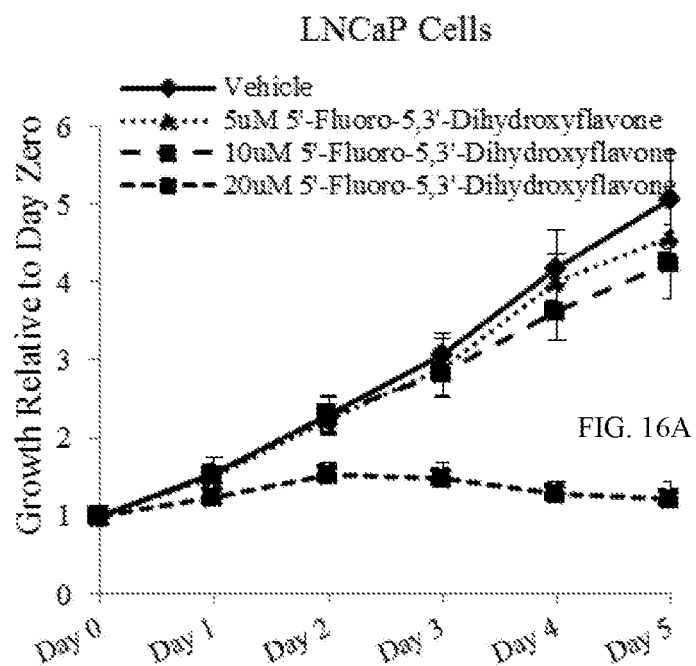
FIG. 16A is a graph showing the effect of 5'-Fluoro-5,3'-Dihydroxyflavone at various concentrations on growth of LNCaP cells.
Figure 16B:
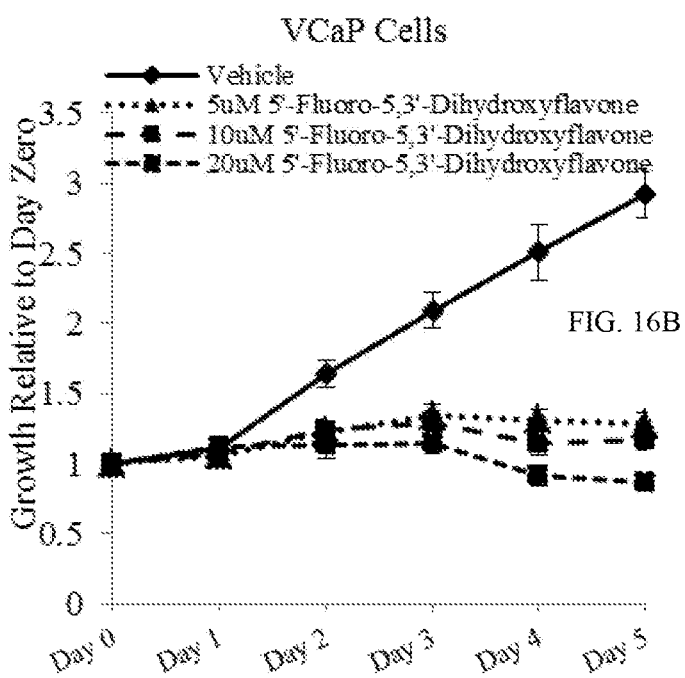
FIG. 16B is a graph showing the effect of 5'-Fluoro-5,3'-Dihydroxyflavone at various concentrations on growth of VCaP cells.
Figure 16C:
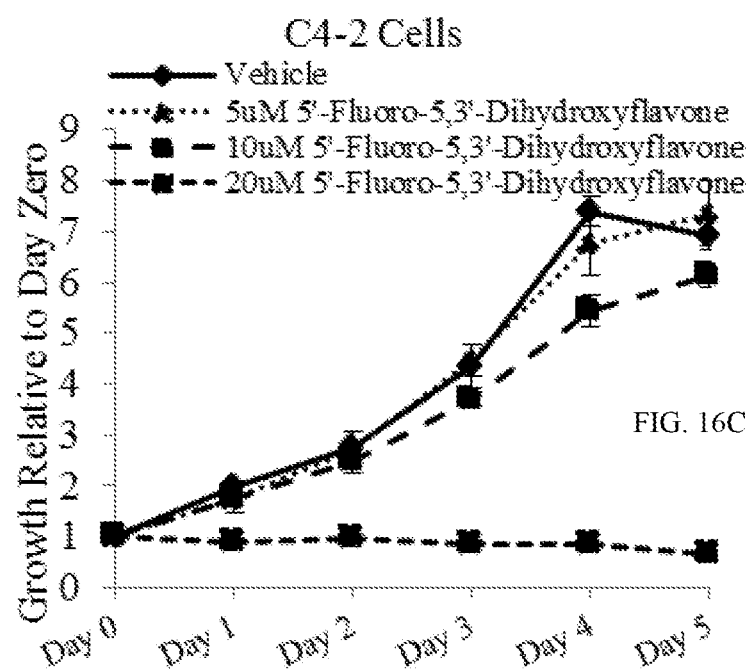
FIG. 16C is a graph showing the effect of 5'-Fluoro-5,3'-Dihydroxyflavone at various concentrations on growth of C4-2 cells.
Figure 16D:
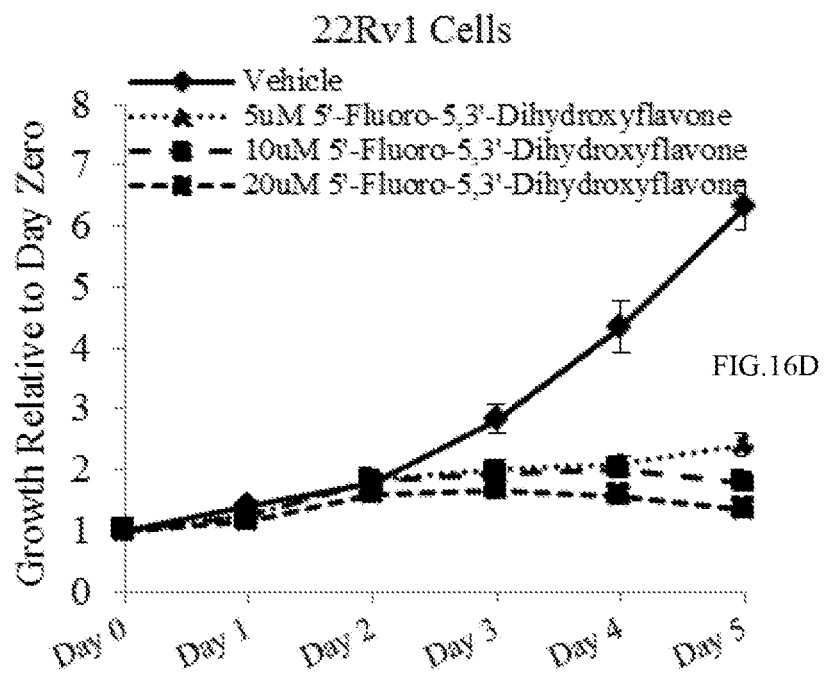
FIG. 16D is a graph showing the effect of 5'-Fluoro-5,3'-Dihydroxyflavone at various concentrations on growth of 22Rv1 cells.
Figure 16E:
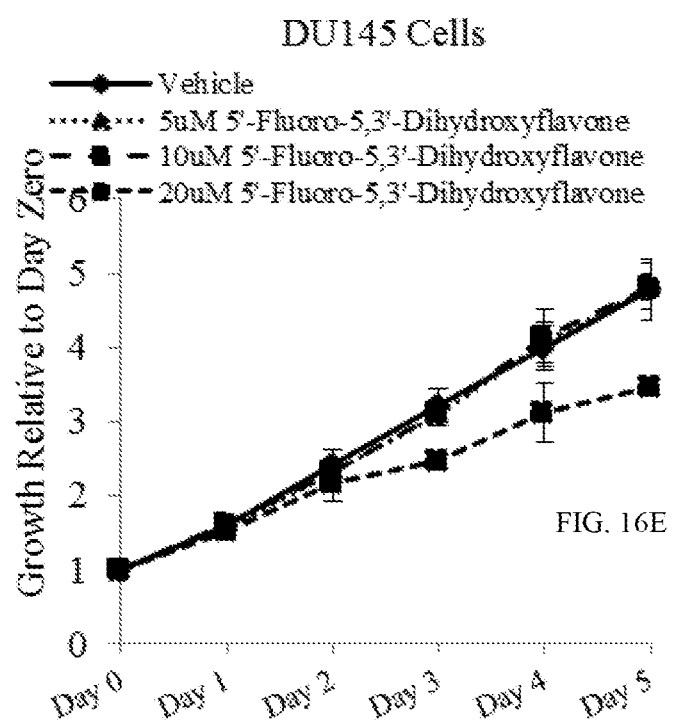
FIG. 16E is a graph showing the effect of 5'-Fluoro-5,3'-Dihydroxyflavone at various concentrations on growth of DU145 cells.

Compound 5'-fluoro-5,3'-dihydroxyflavone was more selective for the ELK1-dependent promoter activity than ARE-dependent activity, similar to its non-fluorinated parent compound. It also selectively inhibited growth of AR-positive cells (LNCaP, VCaP, 22Rv1, and C4-2) at a comparable dose, compared to its parent compound (FIGS. 16A, 16B, 16C, and 16D) but did not inhibit growth of AR-negative (DU145) cells (FIG. 16E). 5'-fluoro-5,3'-dihydroxyflavone did not affect activation of ELK1 by MEK/ERK.

Metabolites

Serum from mice that were injected with 250 mg/kg of 5,3'-Dihydroxyflavone every other day for two weeks was analyzed to identify potential metabolites by LCMS using hypothesized mass transitions. Unmetabolized compound and a single glucuronide metabolite modified at the 3'-OH position were the major compounds identified. Based on this, fluorination at the 5' position is expected to delay metabolism and increase plasma levels and bioavailability of the compound.

Items

Item 1. A pharmaceutical composition, comprising a compound having structural formula VII:

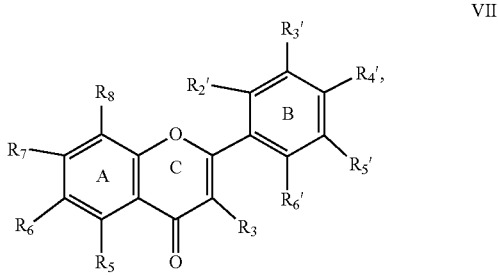

where $R_3$, $R_6$, $R_7$, $R_8$, $R_{2'}$, $R_{4'}$, and $R_{6'}$ are each independently selected from: H, alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, an alkoxy group, a fluorinated alkoxy group, a polar group, an ester and a charged group; and $R_5$, $R_{3'}$ and $R_{5'}$ are each independently selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, alkylheterocycloalkyl group, alkylcycloheteroalkyl group, aralkyl group, and heteroaralkyl group, a charged group, a polar group, OH, and F; and/or a pharmaceutically acceptable ester thereof, and/or a pharmaceutically acceptable salt thereof; and a pharmaceutically acceptable carrier.

Item 2. The pharmaceutical composition of item 1, wherein the compound has structural formula I (5,3'-dihydroxyflavone), and/or a pharmaceutically acceptable ester thereof, and/or a pharmaceutically acceptable salt thereof.

Item 3. The pharmaceutical composition of item 1, wherein the compound has structural formula II (5'-fluoro-5,3'-dihydroxyflavone), and/or a pharmaceutically acceptable ester thereof, and/or a pharmaceutically acceptable salt thereof.

Item 4. The pharmaceutical composition of item 1, where $R_{3'}$ is hydroxyl or a hydrolysable or enzymatically cleavable ester, $R_5$ is hydroxyl or a hydrolysable or enzymatically cleavable ester, $R_{5'}$ is selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, alkylheterocycloalkyl group, alkylcycloheteroalkyl group, aralkyl group, heteroaralkyl group, a charged group, a polar group, OH, and F.

Item 5. The pharmaceutical composition of any one of items 1 to 4, where at least one of $R_{3'}$ and $R_5$, or both, is a hydrolysable or enzymatically cleavable ester.

Item 6. The pharmaceutical composition of any one of items 1 to 5, where $R_{3'}$ is a hydrolysable or enzymatically cleavable ester.

Item 7. The pharmaceutical composition of any one of items 1, 4, 5, or 6, where $R_{2'}$ and $R_{4'}$ are each independently selected from: H, methyl, ethyl, isopropyl, methoxy and trifluoromethoxy (—O—$CF_3$), with the proviso that at least one of $R_{2'}$ and $R_{4'}$ is not H.

Item 8. The pharmaceutical composition of item 1, where $R_{2'}$ and $R_{4'}$ are each independently selected from: H, methyl, ethyl, isopropyl, methoxy and trifluoromethoxy (—O—$CF_3$), with the proviso that at least one of $R_{2'}$ and $R_{4'}$ is not H; and where at least one of $R_{3'}$ and $R_5$, or both, is a hydrolysable or enzymatically cleavable ester.

Item 9. The pharmaceutical composition of item 1, where $R_{3'}$ is hydroxyl or a hydrolysable or enzymatically cleavable ester, $R_5$ is hydroxyl or a hydrolysable or enzymatically cleavable ester, $R_{5'}$ is H, $R_{2'}$ and $R_{4'}$ are each independently selected from: H, methyl, ethyl, isopropyl, methoxy and trifluoromethoxy (—O—$CF_3$), with the proviso that at least one of $R_{2'}$ and $R_{4'}$ is not H; $R_3$ is H, $R_6$ is H, $R_7$ is H, $R_8$ is H, and $R_{6'}$ is H.

Item 10. The pharmaceutical composition of item 1, where $R_{3'}$ is hydroxyl or a hydrolysable or enzymatically cleavable ester, $R_5$ is hydroxyl or a hydrolysable or enzymatically cleavable ester, Ry is H, $R_{4'}$ is methyl, $R_3$ is H, $R_6$ is H, $R_7$ is H, $R_8$ is H, $R_{2'}$ is H, and $R_{6'}$ is H, (5,3'-dihydroxy-4'-methylflavone).

Item 11. The pharmaceutical composition of item 1, where $R_{3'}$ is hydroxyl or a hydrolysable or enzymatically cleavable ester, $R_5$ is hydroxyl or a hydrolysable or enzymatically cleavable ester, $R_{5'}$ is H, $R_{4'}$ is an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, $R_3$ is H, $R_6$ is H, $R_7$ is H, $R_8$ is H, $R_{2'}$ is H, and $R_{6'}$ is H.

Item 12. The pharmaceutical composition of item 1, where $R_{3'}$ is hydroxyl or a hydrolysable or enzymatically cleavable ester, $R_5$ is hydroxyl or a hydrolysable or enzymatically cleavable ester, $R_{2'}$ is H, $R_{4'}$ is H, and $R_{5'}$, $R_3$, $R_6$, $R_7$, Its, and $R_{6'}$ are each independently selected from: H, an alkyl group, heteroalkyl group, aryl group, heteroaryl group, alkenyl group, heteroalkenyl group, alkynyl group, heteroalkynyl group, cycloalkyl group, heterocycloalkyl group, alkylcycloalkyl group, heteroalkylcycloalkyl group, aralkyl group, and heteroaralkyl group, an alkoxy group, a fluorinated alkoxy group, a polar group, an ester and a charged group.

Item 13. The pharmaceutical composition of any one of the preceding items comprising a compound having structural formula VII, with the proviso that $R_5$ is not methoxy and at least one of $R_{3'}$ and $R_{5'}$ is not methoxy.

Item 14. The pharmaceutical composition of any one of items 1 to 13, further comprising an additional therapeutic agent.

Item 15. A method of treatment of a hormone receptor-dependent cancer in a subject in need thereof, comprising: administering a therapeutically effective dose of a pharmaceutical composition according to any one of items 1 to 14 to the subject in need thereof.

Item 16. The method of treatment of a hormone receptor-dependent cancer in a subject in need thereof of item 15, wherein the subject has an androgen receptor-dependent cancer.

Item 17. The method of treatment of a hormone receptor-dependent cancer in a subject in need thereof of item 16, wherein the androgen receptor-dependent cancer is an androgen receptor-dependent prostate cancer.

Item 18. The method of treatment of a hormone receptor-dependent cancer in a subject in need thereof of item 16 or item 17, wherein the androgen receptor-dependent cancer is an androgen receptor-V7-dependent prostate cancer.

Item 19. The method of treatment of a hormone receptor-dependent cancer in a subject in need thereof of item 15, wherein the subject has an estrogen receptor-dependent cancer.

Item 20. The method of treatment of a hormone receptor-dependent cancer in a subject in need thereof of item 19, wherein the estrogen receptor-dependent cancer is an estrogen receptor-dependent breast cancer.

Item 21. The method of treatment of a hormone receptor-dependent cancer in a subject in need thereof of any one of items 15 to 20, further comprising an adjunct anti-cancer treatment.

Item 22. The method of treatment of a hormone receptor-dependent cancer in a subject in need thereof of any one of items 15 to 21, further comprising administration of an additional therapeutic agent.

Item 23. A commercial package comprising a pharmaceutical composition according to any one of items 1 to 14.

Item 24. A pharmaceutical composition capable of disrupting interaction of ELK1 with AR by specific interaction with ELK1, AR or both ELK1 and AR.

Item 25. A pharmaceutical composition substantially as described herein.

Item 26. A method of treatment of a hormone receptor-dependent cancer in a subject in need thereof substantially as described herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Sequences

Five tandem Gal4 DNA binding domain recognition sequences (SEQ ID NO:1, 103 nucleotides)

(SEQ ID NO: 1)
CGGAGTACTGTCCTCCGAGCGGAGTACTGTCCTCCGACTCGAGCGGAGTAC

TGTCCTCCGATCGGAGTACTGTCCTCCGCGAATTCCGGAGTACTGTCCTCC

G

Variants of Gal4 DNA binding domain recognition sequences may also be used.

Gal4 DNA binding domain coding sequence (SEQ ID NO:2, 441 nucleotides) (partial sequence of NCBI accession #AF264722)

(SEQ ID NO: 2)
ATGAAGCTACTGTCTTCTATCGAACAAGCATGCGATATTTGCCGACTTAAA

AAGCTCAAGTGCTCCAAAGAAAAACCGAAGTGCGCCAAGTGTCTGAAGAAC

AACTGGGAGTGTCGCTACTCTCCCAAAACCAAAAGGTCTCCGCTGACTAGG

GCACATCTGACAGAAGTGGAATCAAGGCTAGAAAGACTCGAACAGCTATTT

CTACTGATTTTTCCTCGAGAAGACCTTGACATGATTTTGAAAATGGATTCT

TTACAGGATATAAAAGCATTGTTAACAGGATTATTTGTACAAGATAATGTG

AATAAAGATGCCGTCACAGATAGATTGGCTTCAGTGGAGACTGATATGCCT

CTAACATTGAGACAGCATAGAATAAGTGCGACATCATCATCGGAAGAGAGT

AGTAACAAAGGTCAAAGACAGTTGACTGTAGCG

Gal4 DNA binding domain (SEQ ID NO:3, 147 aa)

(SEQ ID NO: 3)
MKLLSSIEQACDICRLKKLKCSKEKPKCAKCLKNNWECRYSPKTKRSPLTR

AHLTEVESRLERLEQLFLLIFPREDLDMILKMDSLQDIKALLTGLFVQDNV

NKDAVTDRLASVETDMPLTLRQHRISATSSSEESSNKGQRQLTVS

Full ELK1 protein coding sequence (partial sequence of ELK1 NCBI ACCESSION AB016193)

Nucleotide Sequence encoding full ELK1 protein (SEQ ID NO:4, 1,284 nucleotides)

(SEQ ID NO: 4)
ATGGACCCCAGCGTGACCCTGTGGCAGTTCCTGCTGCAGCTGCTGAGGGAG

CAGGGCAACGCCACATCATCAGCTGGACCAGCAGGGACGGCGGCGAGTTC

AAGCTGGTGGACGCCGAGGAGGTGGCCAGGCTGTGGGGCCTGAGGAAGAAC

AAGACCAACATGAACTACGACAAGCTGAGCAGGGCCCTGAGGTACTACTAC

GACAAGAACATCATCAGGAAGGTGAGCGGCCAGAAGTTCGTGTACAAGTTC

GTGAGCTACCCCGAGGTGGCCGGCTGCAGCACCGAGGACTGCCCCCCCCAG

CCCGAGGTGAGCGTGACCAGCACCATGCCCAACGTGGCCCCCGCCGCCATC

CACGCCGCCCCCGGCGACACCGTGAGCGGCAAGCCCGGCACCCCCAAGGGC

GCCGGCATGGCCGGCCCCGGCGGCCTGGCCAGGAGCAGCAGGAACGAGTAC

ATGAGGAGCGGCCTGTACAGCACCTTCACCATCCAGAGCCTGCAGCCCCAG

CCCCCCCCCCACCCCAGGCCCGCCGTGGTGCTGCCCAACGCCGCCCCCGCC

GGCGCCGCCGCCCCCCCCAGCGGCAGCAGGAGCACCAGCCCCAGCCCCCTG

GAGGCCTGCCTGGAGGCCGAGGAGGCCGGCCTGCCCCTGCAGGTGATCCTG

ACCCCCCCGAGGCCCCCAACCTGAAGAGCGAGGAGCTGAACGTGGAGCCC

GGCCTGGGCAGGGCCCTGCCCCCCGAGGTGAAGGTGGAGGGCCCCAAGGAG

GAGCTGGAGGTGGCCGGCGAGAGGGGCTTCGTGCCCGAGACCACCAAGGCC

GAGCCCGAGGTGCCCCCCAGGAGGGCGTGCCCGCCAGGCTGCCCGCCGTG

GTGATGGACACCGCCGGCCAGGCCGGCGGCCACGCCGCCAGCAGCCCCGAG

ATCAGCCAGCCCCAGAAGGGCAGGAAGCCCAGGGACCTGGAGCTGCCCCTG

AGCCCCAGCCTGCTGGGCGGCCCCGGCCCCGAGAGGACCCCCGGCAGCGGC

AGCGGCAGCGGCCTGCAGGCCCCCGGCCCCGCCCTGACCCCCAGCCTGCTG

CCCACCCACACCCTGACCCCCGTGCTGCTGACCCCCAGCAGCCTGCCCCCC

AGCATCCACTTCTGGAGCACCCTGAGCCCCATCGCCCCCAGGAGCCCCGCC

AAGCTGAGCTTCCAGTTCCCCAGCAGCGGCAGCGCCCAGGTGCACATCCCC

AGCATCAGCGTGGACGGCCTGAGCACCCCCGTGGTGCTGAGCCCCGGCCCC

CAGAAGCCC

Nucleotide sequence encoding ELK1 with deletion of first 86 amino acids compared to SEQ ID NO:4 (SEQ ID NO:5, 1,086 nucleotides)

(SEQ ID NO: 5)
AGCTACCCCGAGGTGGCCGGCTGCAGCACCGAGGACTGCCCCCCCCAGCCC
GAGGTGAGCGTGACCAGCACCATGCCCAACGTGGCCCCCGCCGCCATCCAC
GCCGCCCCCGGCGACACCGTGAGCGGCAAGCCCGGCACCCCCAAGGGCGCC
GGCATGGCCGGCCCCGGCGGCCTGGCCAGGAGCAGCAGGAACGAGTACATG
AGGAGCGGCCTGTACAGCACCTTCACCATCCAGAGCCTGCAGCCCCAGCCC
CCCCCCCACCCCAGGCCCGCCGTGGTGCTGCCCAACGCCGCCCCCGCCGGC
GCCGCCGCCCCCCCCAGCGGCAGCAGGAGCACCAGCCCCAGCCCCCTGGAG
GCCTGCCTGGAGGCCGAGGAGGCCGGCCTGCCCCTGCAGGTGATCCTGACC
CCCCCCGAGGCCCCCAACCTGAAGAGCGAGGAGCTGAACGTGGAGCCCGGC
CTGGGCAGGGCCCTGCCCCCCGAGGTGAAGGTGGAGGGCCCCAAGGAGGAG
CTGGAGGTGGCCGGCGAGAGGGGCTTCGTGCCCGAGACCACCAAGGCCGAG
CCCGAGGTGCCCCCCAGGAGGGCGTGCCCGCCAGGCTGCCCGCCGTGGTG
ATGGACACCGCCGGCCAGGCCGGCGGCCACGCCGCCAGCAGCCCCGAGATC
AGCCAGCCCCAGAAGGGCAGGAAGCCCAGGGACCTGGAGCTGCCCCTGAGC
CCCAGCCTGCTGGGCGGCCCCGGCCCCGAGAGGACCCCCGGCAGCGGCAGC
GGCAGCGGCCTGCAGGCCCCCGGCCCCGCCCTGACCCCCAGCCTGCTGCCC
ACCCACACCCTGACCCCCGTGCTGCTGACCCCCAGCAGCCTGCCCCCCAGC
ATCCACTTCTGGAGCACCCTGAGCCCCATCGCCCCCAGGAGCCCCGCCAAG
CTGAGCTTCCAGTTCCCCAGCAGCGGCAGCGCCCAGGTGCACATCCCCAGC
ATCAGCGTGGACGGCCTGAGCACCCCCGTGGTGCTGAGCCCCGGCCCCAGA
AGCCC

Complete ELK1 protein (SEQ ID NO:6, 428 aa)

(SEQ ID NO: 6)
MDPSVTLWQFLLQLLREQGNGHIISWTSRDGGEFKLVDAEEVARLWGLRKN
KTNMNYDKLSRALRYYYDKNIIRKVSGQKFVYHFVSYPEVAGCSTEDCPPQ
PEVSVTSTMPNVAPAAIHAAPGDTVSGKPGTPKGAGMAGPGGLARSSRNEY
MRSGLYSTFTIQSLQPQPPPHPRPAVVLPNAAPAGAAAPPSGSRSTSPSPL
EACLEAEEAGLPLQVILTPPEAPNLKSEELNVEPGLGRALPPEVKVEGPKE
ELEVAGERGFVPETTKAEPEVPPQEGVPARLPAVVMDTAGQAGGHAASSPE
ISQPQKGRKPRDLELPLSPSLLGGPGPERTPGSGSGSGLQAPGPALTPSLL
PTHTLTPVLLTPSSLPPSTHFWSTLSPIAPRSPAKLSFQFPSSGSAQVHIP
SISVDGLSTPVVLSPGPQKP

ELK1 with deletion of first 86 amino acids compared to SEQ ID NO:6 (truncated ELK1, SEQ ID NO:7, 342 aa)

(SEQ ID NO: 7)
SYPEVAGCSTEDCPPQPEVSVTSTMPNVAPAAIHAAPGDTVSGKPGTPKGA
GMAGPGGLARSSRNEYMRSGLYSTFTIQSLQPQPPPHPRPAVVLPNAAPAG
AAAPPSGSRSTSPSPLEACLEAEEAGLPLQVILTPPEAPNLKSEELNVEPG
LGRALPPEVKVEGPKEELEVAGERGFVPETTKAEPEVPPQEGVPARLPAVV
MDTAGQAGGHAASSPEISQPQKGRKPRDLELPLSPSLLGGPGPERTPGSGS
GSGLQAPGPALTPSLLPTHTLTPVLLTPSSLPPSIHFWSTLSPIAPRSPAK
LSFQFPSSGSAQVHIPSISVDGLSTPVVLSPGPQKP

Amino acid sequence of the ELK1-Gal4 DNA binding domain fusion protein (SEQ ID NO:8, 489 aa)

(SEQ ID NO: 8)
MKLLSSIEQACDICRLKKLKCSKEKPKCAKCLKNNWECRYSPKTKRSPLTR
AHLTEVESRLERLEQLFLLIFPREDLDMILKMDSLQDIKALLTGLFVQDNV
NKDAVTDRLASVETDMPLTLRQHRTSATSSSEESSNKGQRQLTVSSYPEVA
GCDTEDCPPQPEVSVTSTMPNVAPAAIHAAPGDTVSGKPGTPKGAGMAGPG
GLARSSRNEYMRSGLYSTFTIQSLQPQPPPHPRPAVVLPNAAPAGAAAPPS
GSRSTSPSPLEACLEAEEAGLPLQVILTPPEAPNLKSEELNVEPGLGRALP
PEVKVEGPKEELEVAGERGFVPETTKAEPEVPPQEGVPARLPAVVMDTAGQ
AGGHAASSPEISQPQKGRKPRDLELPLSPSLLGGPGPERTPGSGSGSGLQA
PGPALTPSLLPTHTLTPVLLTPSSLPPSIHFWSTLSPIAPRSPAKLSFQFP
SSGSAQVHIPSISVDGLSTPVVLSPGPQKP

Variants of truncated ELK1 (SEQ ID NO: 7) and Gal4 DNA binding domain (SEQ ID NO:3) can be used to produce variants of ELK1-Gal4 DNA binding domain fusion protein of SEQ ID NO:8 which may also be used.

Sequence Encoding Human Androgen Receptor (SEQ ID NO:9, 2,757 nucleotides) NCBI ACCESSION M20132 J03180

(SEQ ID NO: 9)
ATGGAGGTGCAGCTGGGCCTGGGCAGGGTGTACCCCAGGCCCCCCAGCAAG
ACCTACAGGGGCGCCTTCCAGAACCTGTTCCAGAGCGTGAGGGAGGTGATC
CAGAACCCCGGCCCCAGGCACCCCGAGGCCGCCAGCGCCGCCCCCCCCGGC
GCCAGCCTGCTGCTGCTGCAGCAGCAGCAGCAGCAGCAGCAGCAGCAGCAG
CAGCAGCAGCAGCAGCAGCAGCAGCAGCAGGAGACCAGCCCCAGGCAGCAG
CAGCAGCAGCAGGGCGAGGACGGCAGCCCCCAGGCCCACAGGAGGGGCCCC
ACCGGCTACCTGGTGCTGGACGAGGAGCAGCAGCCCAGCCAGCCCCAGAGC
GCCCTGGAGTGCCACCCCGAGAGGGGCTGCGTGCCCGAGCCCGGCGCCGCC
GTGGCCGCCAGCAAGGGCCTGCCCCAGCAGCTGCCCGCCCCCCCCGACGAG
GACGACAGCGCCGCCCCCAGCACCCTGAGCCTGCTGGGCCCCACCTTCCCC
GGCCTGAGCAGCTGCAGCGCCGACCTGAAGGACATCCTGAGCGAGGCCAGC
ACCATGCAGCTGCTGCAGCAGCAGCAGCAGGAGGCCGTGAGCGAGGGCAGC
AGCAGCGGCAGGGCCAGGGAGGCCAGCGGCGCCCCCACCAGCAGCAAGGAC
AACTACCTGGGCGGCACCAGCACCATCAGCGACAACGCCAAGGAGCTGTGC
AAGGCCGTGAGCGTGAGCATGGGCCTGGGCGTGGAGGCCCTGGAGCACCTG
AGCCCCGGCGAGCAGCTGAGGGGCGACTGCATGTACGCCCCCCTGCTGGGC

-continued

```
GTGCCCCCGCCGTGAGGCCCACCCCCTGCGCCCCCTGGCCGAGTGCAAG

GGCAGCCTGCTGGACGACAGCGCCGGCAAGAGCACCGAGGACACCGCCGAG

TACAGCCCCTTCAAGGGCGGCTACACCAAGGGCCTGGAGGGCGAGAGCCTG

GGCTGCAGCGGCAGCGCCGCCGCCGGCAGCAGCGGCACCCTGGAGCTGCCC

AGCACCCTGAGCCTGTACAAGAGCGGCGCCCTGGACGAGGCCGCCGCCTAC

CAGAGCAGGGACTACTACAACTTCCCCCTGGCCCTGGCCGGCCCCCCCCCC

CCCCCCCCCCCCCCCACCCCCACGCCAGGATCAAGCTGGAGAACCCCCTG

GACTACGGCAGCGCCTGGGCCGCCGCCGCCGCCCAGTGCAGGTACGGCGAC

CTGGCCAGCCTGCACGGCGCCGGCGCCGCCGGCCCCGGCAGCGGCAGCCCC

AGCGCCGCCGCCAGCAGCAGCTGGCACACCCTGTTCACCGCCGAGGAGGGC

CAGCTGTACGGCCCCTGCGGCGGCGGCGGCGGCGGCGGCGGCGGCGGCGGC

GGCGGCGGCGGCGGCGGCGGCGGCGGCGGCGGCGGCGAGGCCGGCGCC

GTGGCCCCCTACGGCTACACCAGGCCCCCCAGGGCCTGGCCGGCCAGGAG

AGCGACTTCACCGCCCCCGACGTGTGGTACCCCGGCGGCATGGTGAGCAGG

GTGCCCTACCCCAGCCCCACCTGCGTGAAGAGCGAGATGGGCCCCTGGATG

GACAGCTACAGCGGCCCCTACGGCGACATGAGGCTGGAGACCGCCAGGGAC

CACGTGCTGCCCATCGACTACTACTTCCCCCCCCAGAAGACCTGCCTGATC

TGCGGCGACGAGGCCAGCGGCTGCCACTACGGCGCCCTGACCTGCGGCAGC

TGCAAGGTGTTCTTCAAGAGGGCCGCCGAGGGCAAGCAGAAGTACCTGTGC

GCCAGCAGGAACGACTGCACCATCGACAAGTTCAGGAGGAAGAACTGCCCC

AGCTGCAGGCTGAGGAAGTGCTACGAGGCCGGCATGACCCTGGGCGCCAGG

AAGCTGAAGAAGCTGGGCAACCTGAAGCTGCAGGAGGAGGGCGAGGCCAGC

AGCACCACCAGCCCCACCGAGGAGACCACCCAGAAGCTGACCGTGAGCCAC

ATCGAGGGCTACGAGTCCCAGCCCATCTTCCTGAACGTGCTGGAGGCCATC

GAGCCCGGCGTGGTGTGCGCCGGCCACGACAACAACCAGCCCGACAGCTTC

GCCGCCCTGCTGAGCAGCCTGAACGAGCTGGGCGAGAGGCAGCTGGTGCAC

GTGGTGAAGTGGGCCAAGGCCCTGCCCGGCTTCAGGAACCTGCACGTGGAC

GACCAGATGGCCHTGATCCAGTACAGCTGGATGGGCCTGATGGTGTTCGCC

ATGGGCTGGAGGAGCTTCACCAACGTGAACAGCAGGATGCTGTACTTCGCC

CCCGACCTGGTGTTCAACGAGTACAGGATGCACAAGAGCAGGATGTACAGC

GCAGTGCGTGAGGATAGGCACCTGAGCCAGGAGTTCGGCTGGCTGCAGATC

ACCCCCCAGGAGTTCCTGTGCATGAAGGCCCTGCTGCTGTTCAGCATCATC

CCCGTGGACGGCCTGAAGAACCAGAAGTTCTTCGACGAGCTGAGGATGAAC

TACATCAAGGAGCTGGACAGGATCATCGCCTGCAAGAGGAAGAACCCCACC

AGCTGCAGCAGGAGGTTCTACCAGCTGACCAAGCTGCTGGACAGCGTGCAG

CCCATCGCCAGGGAGCTGCACCAGTTCACCTTCGACCTGCTGATCAAGAGC

CACATGGTGAGCGTGGACTTCCCCGAGATGATGGCCGAGATCATCAGCGTG

CAGGTGCCCAAGATCCTGAGCGGCAAGGTGAAGCCCATCTACTTCCACACC

CAG
```

Amino Acid Sequence of Human Androgen Receptor (919 aa)

(SEQ ID NO: 10)
```
MEVQLGLGRVYPRPPSKTYRGAFQNLFQSVREVIGNPGPRHPEAASAAPPG

ASLLLLQQQQQQQQQQQQQQQQQQQQQETSPRQQQQQQGEDGSPQAHRRGP

TGYLVLDEEQQPSQPQSALECHPERGCVPEPGAAVAASKGLPQQLPAPPDE

DDSAAPSTLSLLGPTFPGLSSCSADLKDILSEASTMQLLQQQQQEAVSEGS

SSGRAREASGAPTSSKDNYLGGTSTISDNAKELCKACSVSMGLGVEALEHL

SPGEQLRGDCMYAPLLGCPPAVRPTPCAPLAECKGSLLDDSAGKSTEDTAE

YSPFKGGYTKGLEGESLGCSGSAAAGSSGTLELPSTLSLYKSGALDEAAAY

QSRDYYNFPLALAGPPPPPPPHPHARIKLENPLDYGSAWAAAAAQCRYGD

LASLHGAGAAGPGSGSPSAAASSWHTLFTAEEGQLYGPCGGGGGGGGGG

GGGGGGGGGGGGEAGAVAPYGYTRPPQGLAGQESDFTAPDVWYPGGMVSR

VPYPSPTCVKSEMGPWMDSYSGPYGDMRLETARDHVLPIDYYFPPQKTCLI

CGDEASGCHYGALTCGSCKVFFKRAAEGKQKYLCASRNDCTIDKFRRKNCP

SCRLRKCYEAGMTLGARKLKKLGNLKLQEEGEASSTTSPTEETTQKLTVSH

IEGYECQPIFLNVLEAIEPGVVCAGHDNNQPDSFAALLSSLNELSERQLVH

VVKWAKALPGFRNLHVDDQMAVIQYSWMGLMVFAMGWRSFTNVNSRMLYFA

PDLVFNEYRMHKSRMYSQCVRMRHLSQEFGWLQITPQEFLCMKALLLFSII

PVDGLKNQKFFDELRMNYIKELDRIIACKRKNPTSCSRRFYQLTKLLDSVQ

PIARELHQFTFDLLIKSHMVSVDFPEMMAEIISVQVPKILSGKVKPIYFHT

Q
```

Variants, including splice variants, of human AR of SEQ ID NO:10 may also be used.

Canonical ARE sequence-SEQ ID NO:11

(SEQ ID NO: 11)
GCTTGTACAGGATGTTCTGCATGCTCTAGATGTACAGGATGTTCT

Variants of the canonical ARE (SEQ ID NO: 11) may also be used.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A pharmaceutical composition, comprising a compound having structural formula VII:

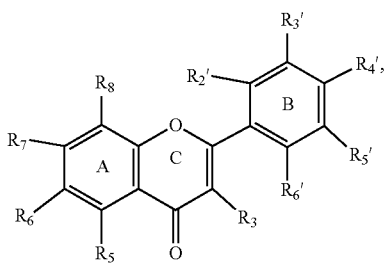

where $R_3$, $R_6$, $R_7$, $R_{2'}$, $R_{4'}$, and $R_{6'}$ are each; $R_8$ is H; and $R_5$ and $R_{3'}$ are each independently hydroxyl, a hydrolysable or an enzymatically cleavable ester $R_{5'}$ is F; and/or a pharmaceutically acceptable ester thereof, and/or a pharmaceutically acceptable salt thereof; and a pharmaceutically acceptable carrier.

2. The pharmaceutical composition of claim 1, where at least one of $R_{3'}$ and $R_5$, or both, is a hydrolysable or enzymatically cleavable ester.

3. The pharmaceutical composition of claim 1, where $R_{3'}$ is a hydrolysable or enzymatically cleavable ester.

4. The pharmaceutical composition of claim 1, further comprising an additional therapeutic agent.

5. A method of treatment of a hormone receptor-dependent cancer in a subject in need thereof, comprising: administering a therapeutically effective dose of a pharmaceutical composition according to claim 1 to the subject in need thereof.

6. The method of treatment of a hormone receptor-dependent cancer in a subject in need thereof of claim 5, wherein the subject has an androgen receptor-dependent cancer.

7. The method of treatment of a hormone receptor-dependent cancer in a subject in need thereof of claim 6, wherein the androgen receptor-dependent cancer is an androgen receptor-dependent prostate cancer.

8. The method of treatment of a hormone receptor-dependent cancer in a subject in need thereof of claim 6, wherein the androgen receptor-dependent cancer is an androgen receptor-V7-dependent prostate cancer.

9. The method of treatment of a hormone receptor-dependent cancer in a subject in need thereof of claim 5, wherein the subject has an estrogen receptor-dependent cancer.

10. The method of treatment of a hormone receptor-dependent cancer in a subject in need thereof of claim 9, wherein the estrogen receptor-dependent cancer is an estrogen receptor-dependent breast cancer.

11. The method of treatment of a hormone receptor-dependent cancer in a subject in need thereof of claim 5, further comprising an adjunct anti-cancer treatment.

12. The method of treatment of a hormone receptor-dependent cancer in a subject in need thereof of claim 5, further comprising administration of an additional therapeutic agent.

* * * * *

SEQUENCE LISTING

<160> NUMBER OF SEQ ID NOS: 11

<210> SEQ ID NO 1
<211> LENGTH: 103
<212> TYPE: DNA
<213> ORGANISM: Artificial Sequence
<220> FEATURE:
<223> OTHER INFORMATION: Five tandem Gal4 DNA binding domain recognition
      sequences

<400> SEQUENCE: 1
cggagtactg tcctccgagc ggagtactgt cctccgactc gagcggagta ctgtcctccg      60
atcggagtac tgtcctccgc gaattccgga gtactgtcct ccg                      103

<210> SEQ ID NO 2
<211> LENGTH: 441
<212> TYPE: DNA
<213> ORGANISM: Artificial Sequence
<220> FEATURE:
<223> OTHER INFORMATION: Gal4 DNA binding domain coding sequence

<400> SEQUENCE: 2
atgaagctac tgtcttctat cgaacaagca tgcgatattt gccgacttaa aaagctcaag      60
tgctccaaag aaaaaccgaa gtgcgccaag tgtctgaaga caactgggga gtgtcgctac     120
tctcccaaaa ccaaaaggtc tccgctgact agggcacatc tgacagaagt ggaatcaagg     180
ctagaaagac tggaacagct atttctactg attttttcctc gagaagacct tgacatgatt     240
ttgaaaatgg attctttaca ggatataaaa gcattgttaa caggattatt tgtacaagat     300
aatgtgaata aagatgccgt cacagataga ttggcttcag tggagactga tatgcctcta     360
acattgagac agcatagaat aagtgcgaca tcatcatcgg aagagagtag taacaaaggt     420
caaagacagt tgactgtatc g                                              441

<210> SEQ ID NO 3
<211> LENGTH: 147
<212> TYPE: PRT
<213> ORGANISM: Artificial Sequence
<220> FEATURE:
<223> OTHER INFORMATION: Gal4 DNA binding domain

<400> SEQUENCE: 3

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

```
Ala Thr Ser Ser Ser Glu Glu Ser Ser Asn Lys Gly Gln Arg Gln Leu
        130                 135                 140
Thr Val Ser
145

<210> SEQ ID NO 4
<211> LENGTH: 1284
<212> TYPE: DNA
<213> ORGANISM: Homo sapiens

<400> SEQUENCE: 4
atggacccca gcgtgaccct gtggcagttc ctgctgcagc tgctgaggga gcagggcaac        60
ggccacatca tcagctggac cagcagggac ggcggcgagt tcaagctggt ggacgccgag       120
gaggtggcca ggctgtgggg cctgaggaag aacaagacca acatgaacta cgacaagctg       180
agcagggccc tgaggtacta ctacgacaag aacatcatca ggaaggtgag cggccagaag       240
ttcgtgtaca agttcgtgag ctaccccgag gtggccggct gcagcaccga ggactgcccc       300
ccccagcccg aggtgagcgt gaccagcacc atgcccaacg tggcccccgc cgccatccac       360 gccgccccg cgacaccgt gagcggcaag cccggcaccc caagggcgc cggcatggcc          420 ggccccggcg gcctggccag gagcagcagg aacgagtaca tgaggagcgg cctgtacagc       480
accttcacca tccagagcct gcagcccag cccccccccc acccaggcc gccgtggtg          540 ctgcccaacg ccgccccgc cggcgccgcc gcccccccca gcggcagcag gagcaccagc       600
cccagccccc tggaggcctg cctggaggcc gaggaggccg gcctgcccct gcaggtgatc       660 ctgaccccccc ccgaggcccc caacctgaag agcgaggagc tgaacgtgga gcccggcctg       720
ggcagggccc tgcccccccga ggtgaaggtg gagggcccca aggaggagct ggaggtggcc       780
ggcgagaggg gcttcgtgcc cgagaccacc aaggccgagc ccgaggtgcc ccccccaggag       840 ggcgtgcccg ccaggctgcc cgccgtggtg atggacaccg ccggccaggc cggcggccac       900
gccgccagca gccccgagat cagccagccc cagaagggca ggaagcccag ggacctggag       960 ctgccccctga gccccagcct gctgggcggc cccggccccg agaggacccc cggcagcggc       1020
agcggcagcg gcctgcaggc ccccggcccc gccctgaccc ccagcctgct gccaccccac       1080 accctgacccc ccgtgctgct gaccccccagc agcctgcccc ccagcatcca cttctggagc       1140
accctgagcc ccatcgcccc caggagcccc gccaagctga gcttccagtt ccccagcagc       1200
ggcagcgccc aggtgcacat ccccagcatc agcgtggacg gcctgagcac ccccgtggtg       1260
ctgagccccg gcccccagaa gccc                                              1284

<210> SEQ ID NO 5
<211> LENGTH: 1026
<212> TYPE: DNA
<213> ORGANISM: Artificial Sequence
<220> FEATURE:
<223> OTHER INFORMATION: Nucleotide sequence encoding ELK1 with deletion
      of first 86 amino acids compared to SEQ ID NO:4

<400> SEQUENCE: 5
agctaccccg aggtggccgg ctgcagcacc gaggactgcc ccccccagcc cgaggtgagc        60
gtgaccagca ccatgcccaa cgtggccccc gccgccatcc acgccgcccc cggcgacacc       120
gtgagcggca agcccggcac ccccaagggc gccggcatgg ccggccccgg cggcctggcc       180
aggagcagca ggaacgagta catgaggagc ggcctgtaca gcaccttcac catccagagc       240
ctgcagcccc agcccccccc ccacccccagg cccgccgtgg tgctgcccaa cgccgccccc       300
```

| | | |
|---|---|---|
| gccggcgccg ccgccccccc cagcggcagc aggagcacca gccccagccc cctggaggcc | 360 | |
| tgcctggagg ccgaggaggc cggcctgccc ctgcaggtga tcctgacccc ccccgaggcc | 420 | |
| cccaacctga agagcgagga gctgaacgtg gagcccggcc tgggcagggc cctgcccccc | 480 | |
| gaggtgaagg tggagggccc caaggaggag ctggaggtgg ccggcgagag gggcttcgtg | 540 | |
| cccgagacca ccaaggccga gcccgaggtg ccccccccagg agggcgtgcc cgccaggctg | 600 | |
| cccgccgtgg tgatggacac cgccggccag gccggcggcc acgccgccag cagccccgag | 660 | |
| atcagccagc ccagaaggg caggaagccc agggacctgg agctgcccct gagccccagc | 720 | |
| ctgctgggcg gccccggccc cgagaggacc cccggcagcg gcagcggcag cggcctgcag | 780 | |
| gcccccggcc ccgccctgac cccagcctg ctgcccaccc acaccctgac cccgtgctg | 840 | |
| ctgaccccca gcagcctgcc cccagcatc cacttctgga gcaccctgag ccccatcgcc | 900 | |
| cccaggagcc ccgccaagct gagcttccag ttccccagca gcggcagcgc ccaggtgcac | 960 | |
| atccccagca tcagcgtgga cggcctgagc accccgtgg tgctgagccc cggccccccag | 1020 |
| aagccc | 1026 | |

<210> SEQ ID NO 6
<211> LENGTH: 428
<212> TYPE: PRT
<213> ORGANISM: Homo sapiens

<400> SEQUENCE: 6

Met Asp Pro Ser Val Thr Leu Trp Gln Phe Leu Leu Gln Leu Leu Arg
1               5                   10                  15

Glu Gln Gly Asn Gly His Ile Ile Ser Trp Thr Ser Arg Asp Gly Gly
            20                  25                  30

Glu Phe Lys Leu Val Asp Ala Glu Val Ala Arg Leu Trp Gly Leu
        35                  40                  45

Arg Lys Asn Lys Thr Asn Met Asn Tyr Asp Lys Leu Ser Arg Ala Leu
    50                  55                  60

Arg Tyr Tyr Tyr Asp Lys Asn Ile Ile Arg Lys Val Ser Gly Gln Lys
65                  70                  75                  80

Phe Val Tyr Lys Phe Val Ser Tyr Pro Glu Val Ala Gly Cys Ser Thr
                85                  90                  95

Glu Asp Cys Pro Pro Gln Pro Glu Val Ser Val Thr Ser Thr Met Pro
            100                 105                 110

Asn Val Ala Pro Ala Ala Ile His Ala Ala Pro Gly Asp Thr Val Ser
        115                 120                 125

Gly Lys Pro Gly Thr Pro Lys Gly Ala Gly Met Ala Gly Pro Gly Gly
    130                 135                 140

Leu Ala Arg Ser Ser Arg Asn Glu Tyr Met Arg Ser Gly Leu Tyr Ser
145                 150                 155                 160

Thr Phe Thr Ile Gln Ser Leu Gln Pro Gln Pro Pro His Pro Arg
                165                 170                 175

Pro Ala Val Val Leu Pro Asn Ala Ala Pro Ala Gly Ala Ala Ala Pro
            180                 185                 190

Pro Ser Gly Ser Arg Ser Thr Ser Pro Ser Pro Leu Glu Ala Cys Leu
        195                 200                 205

Glu Ala Glu Glu Ala Gly Leu Pro Leu Gln Val Ile Leu Thr Pro Pro
    210                 215                 220

Glu Ala Pro Asn Leu Lys Ser Glu Glu Leu Asn Val Glu Pro Gly Leu
225                 230                 235                 240

```
Gly Arg Ala Leu Pro Pro Glu Val Lys Val Glu Gly Pro Lys Glu Glu
                245                 250                 255

Leu Glu Val Ala Gly Glu Arg Gly Phe Val Pro Glu Thr Thr Lys Ala
            260                 265                 270

Glu Pro Glu Val Pro Pro Gln Glu Gly Val Pro Ala Arg Leu Pro Ala
        275                 280                 285

Val Val Met Asp Thr Ala Gly Gln Ala Gly Gly His Ala Ala Ser Ser
    290                 295                 300

Pro Glu Ile Ser Gln Pro Gln Lys Gly Arg Lys Pro Arg Asp Leu Glu
305                 310                 315                 320

Leu Pro Leu Ser Pro Ser Leu Leu Gly Gly Pro Gly Pro Glu Arg Thr
                325                 330                 335

Pro Gly Ser Gly Ser Gly Ser Gly Leu Gln Ala Pro Gly Pro Ala Leu
            340                 345                 350

Thr Pro Ser Leu Leu Pro Thr His Thr Leu Thr Pro Val Leu Leu Thr
        355                 360                 365

Pro Ser Ser Leu Pro Pro Ser Ile His Phe Trp Ser Thr Leu Ser Pro
    370                 375                 380

Ile Ala Pro Arg Ser Pro Ala Lys Leu Ser Phe Gln Phe Pro Ser Ser
385                 390                 395                 400

Gly Ser Ala Gln Val His Ile Pro Ser Ile Ser Val Asp Gly Leu Ser
                405                 410                 415

Thr Pro Val Val Leu Ser Pro Gly Pro Gln Lys Pro
            420                 425

<210> SEQ ID NO 7
<211> LENGTH: 342
<212> TYPE: PRT
<213> ORGANISM: Artificial Sequence
<220> FEATURE:
<223> OTHER INFORMATION: ELK1 with deletion of first 86 amino acids
      compared to SEQ ID NO:6 (truncated ELK1)

<400> SEQUENCE: 7

Ser Tyr Pro Glu Val Ala Gly Cys Ser Thr Glu Asp Cys Pro Pro Gln
1               5                   10                  15

Pro Glu Val Ser Val Thr Ser Thr Met Pro Asn Val Ala Pro Ala Ala
            20                  25                  30

Ile His Ala Ala Pro Gly Asp Thr Val Ser Gly Lys Pro Gly Thr Pro
        35                  40                  45

Lys Gly Ala Gly Met Ala Gly Pro Gly Gly Leu Ala Arg Ser Ser Arg
    50                  55                  60

Asn Glu Tyr Met Arg Ser Gly Leu Tyr Ser Thr Phe Thr Ile Gln Ser
65                  70                  75                  80

Leu Gln Pro Gln Pro Pro His Pro Arg Pro Ala Val Val Leu Pro
                85                  90                  95

Asn Ala Ala Pro Ala Gly Ala Ala Ala Pro Ser Gly Ser Arg Ser
            100                 105                 110

Thr Ser Pro Ser Pro Leu Glu Ala Cys Leu Glu Ala Glu Glu Ala Gly
        115                 120                 125

Leu Pro Leu Gln Val Ile Leu Thr Pro Pro Glu Ala Pro Asn Leu Lys
    130                 135                 140

Ser Glu Glu Leu Asn Val Glu Pro Gly Leu Gly Arg Ala Leu Pro Pro
145                 150                 155                 160

Glu Val Lys Val Glu Gly Pro Lys Glu Glu Leu Glu Val Ala Gly Glu
                165                 170                 175
```

```
Arg Gly Phe Val Pro Glu Thr Thr Lys Ala Glu Pro Glu Val Pro Pro
                180                 185                 190

Gln Glu Gly Val Pro Ala Arg Leu Pro Ala Val Val Met Asp Thr Ala
            195                 200                 205

Gly Gln Ala Gly Gly His Ala Ala Ser Ser Pro Glu Ile Ser Gln Pro
        210                 215                 220

Gln Lys Gly Arg Lys Pro Arg Asp Leu Glu Leu Pro Leu Ser Pro Ser
225                 230                 235                 240

Leu Leu Gly Gly Pro Gly Pro Glu Arg Thr Pro Gly Ser Gly Ser Gly
                245                 250                 255

Ser Gly Leu Gln Ala Pro Gly Pro Ala Leu Thr Pro Ser Leu Leu Pro
            260                 265                 270

Thr His Thr Leu Thr Pro Val Leu Leu Thr Pro Ser Ser Leu Pro Pro
        275                 280                 285

Ser Ile His Phe Trp Ser Thr Leu Ser Pro Ile Ala Pro Arg Ser Pro
290                 295                 300

Ala Lys Leu Ser Phe Gln Phe Pro Ser Ser Gly Ser Ala Gln Val His
305                 310                 315                 320

Ile Pro Ser Ile Ser Val Asp Gly Leu Ser Thr Pro Val Val Leu Ser
                325                 330                 335

Pro Gly Pro Gln Lys Pro
                340

<210> SEQ ID NO 8
<211> LENGTH: 489
<212> TYPE: PRT
<213> ORGANISM: Artificial Sequence
<220> FEATURE:
<223> OTHER INFORMATION: ELK1-Gal4 DNA binding domain fusion protein

<400> SEQUENCE: 8

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
                20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
        50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
130                 135                 140

Thr Val Ser Ser Tyr Pro Glu Val Ala Gly Cys Ser Thr Glu Asp Cys
145                 150                 155                 160

Pro Pro Gln Pro Glu Val Ser Val Thr Ser Thr Met Pro Asn Val Ala
                165                 170                 175

Pro Ala Ala Ile His Ala Ala Pro Gly Asp Thr Val Ser Gly Lys Pro
            180                 185                 190
```

-continued

Gly Thr Pro Lys Gly Ala Gly Met Ala Gly Pro Gly Leu Ala Arg
            195                 200                 205

Ser Ser Arg Asn Glu Tyr Met Arg Ser Gly Leu Tyr Ser Thr Phe Thr
    210                 215                 220

Ile Gln Ser Leu Gln Pro Gln Pro Pro His Pro Arg Pro Ala Val
225                 230                 235                 240

Val Leu Pro Asn Ala Ala Pro Ala Gly Ala Ala Pro Pro Ser Gly
                245                 250                 255

Ser Arg Ser Thr Ser Pro Ser Pro Leu Glu Ala Cys Leu Glu Ala Glu
                260                 265                 270

Glu Ala Gly Leu Pro Leu Gln Val Ile Leu Thr Pro Pro Glu Ala Pro
                275                 280                 285

Asn Leu Lys Ser Glu Glu Leu Asn Val Glu Pro Gly Leu Gly Arg Ala
    290                 295                 300

Leu Pro Pro Glu Val Lys Val Glu Gly Pro Lys Glu Glu Leu Glu Val
305                 310                 315                 320

Ala Gly Glu Arg Gly Phe Val Pro Glu Thr Thr Lys Ala Glu Pro Glu
                325                 330                 335

Val Pro Pro Gln Glu Gly Val Pro Ala Arg Leu Pro Ala Val Val Met
                340                 345                 350

Asp Thr Ala Gly Gln Ala Gly Gly His Ala Ala Ser Ser Pro Glu Ile
                355                 360                 365

Ser Gln Pro Gln Lys Gly Arg Lys Pro Arg Asp Leu Glu Leu Pro Leu
    370                 375                 380

Ser Pro Ser Leu Leu Gly Gly Pro Gly Pro Glu Arg Thr Pro Gly Ser
385                 390                 395                 400

Gly Ser Gly Ser Gly Leu Gln Ala Pro Gly Pro Ala Leu Thr Pro Ser
                405                 410                 415

Leu Leu Pro Thr His Thr Leu Thr Pro Val Leu Leu Thr Pro Ser Ser
                420                 425                 430

Leu Pro Pro Ser Ile His Phe Trp Ser Thr Leu Ser Pro Ile Ala Pro
                435                 440                 445

Arg Ser Pro Ala Lys Leu Ser Phe Gln Phe Pro Ser Ser Gly Ser Ala
    450                 455                 460

Gln Val His Ile Pro Ser Ile Ser Val Asp Gly Leu Ser Thr Pro Val
465                 470                 475                 480

Val Leu Ser Pro Gly Pro Gln Lys Pro
                485

<210> SEQ ID NO 9
<211> LENGTH: 2757
<212> TYPE: DNA
<213> ORGANISM: Homo sapiens

<400> SEQUENCE: 9
atggaggtgc agctgggcct gggcagggtg taccccaggc cccccagcaa gacctacagg      60
ggcgccttcc agaacctgtt ccagagcgtg agggaggtga tccagaaccc cggccccagg     120
caccccgagg ccgccagcgc cgccccccc ggcgccagcc tgctgctgct gcagcagcag     180
cagcagcagc agcagcagca gcagcagcag cagcagcagc agcagcagca gcaggagacc     240
agccccaggc agcagcagca gcagcagggc gaggacggca gccccaggc ccacaggagg     300 ggccccaccg gctacctggt gctggacgag gagcagcagc ccagccagcc ccagagcgcc     360
ctggagtgcc accccgagag gggctgcgtg cccgagcccg cgccgccgt ggccgccagc     420

```
aagggcctgc cccagcagct gcccgccccc ccgacgagg acgacagcgc cgcccccagc    480
accctgagcc tgctgggccc caccttcccc ggcctgagca gctgcagcgc cgacctgaag    540
gacatcctga gcgaggccag caccatgcag ctgctgcagc agcagcagca ggaggccgtg    600
agcgagggca gcagcagcgg cagggccagg gaggccagcg gcgcccccac cagcagcaag    660
gacaactacc tgggcggcac cagcaccatc agcgacaacg ccaaggagct gtgcaaggcc    720
gtgagcgtga gcatgggcct gggcgtggag gccctggagc acctgagccc cggcgagcag    780
ctgaggggcg actgcatgta cgcccccctg ctgggcgtgc ccccgccgt gaggcccacc    840 ccctgcgccc ccctggccga gtgcaagggc agcctgctgg acgacagcgc cggcaagagc    900
accgaggaca ccgccgagta cagccccttc aagggcggct acaccaaggg cctggagggc    960
gagagcctgg gctgcagcgg cagcgccgcc gccggcagca gcggcaccct ggagctgccc    1020
agcaccctga gcctgtacaa gagcggcgcc ctggacgagg ccgccgccta ccagagcagg    1080
gactactaca acttcccccct ggccctggcc ggccccccc cccccccccc ccccccccac    1140
ccccacgcca ggatcaagct ggagaacccc ctggactacg gcagcgcctg gccgccgcc    1200 gccgcccagt gcaggtacgg cgacctggcc agcctgcacg gcgccggcgc cgccggcccc    1260
ggcagcggca gccccagcgc cgccgccagc agcagctggc acaccctgtt caccgccgag    1320
gagggccagc tgtacggccc ctgcggcggc ggcggcggcg gcggcggcgg cggcggcggc    1380
ggcggcggcg gcggcggcgg cggcggcggc ggcggcgagg ccggcgccgt ggcccccctac    1440 ggctacacca ggccccccca gggcctggcc ggccaggaga gcgacttcac cgcccccgac    1500
gtgtggtacc ccggcggcat ggtgagcagg gtgccctacc ccagccccac ctgcgtgaag    1560
agcgagatgg gccctggat ggacagctac agcggcccct acggcgacat gaggctggag    1620
accgccaggg accacgtgct gcccatcgac tactacttcc cccccagaa gacctgcctg    1680 atctgcggcg acgaggccag cggctgccac tacggcgccc tgacctgcgg cagctgcaag    1740
gtgttcttca gagggccgc cgagggcaag cagaagtacc tgtgcgccag caggaacgac    1800
tgcaccatcg acaagttcag gaggaagaac tgccccagct gcaggctgag gaagtgctac    1860
gaggccggca tgaccctggg cgccaggaag ctgaagaagc tgggcaacct gaagctgcag    1920
gaggagggcg aggccagcag caccaccagc cccaccgagg agaccaccca gaagctgacc    1980
gtgagccaca tcgagggcta cgagtgccag cccatcttcc tgaacgtgct ggaggccatc    2040
gagcccggcg tggtgtgcgc cggccacgac aacaaccagc ccgacagctt cgccgccctg    2100
ctgagcagcc tgaacgagct gggcgagagg cagctggtgc acgtggtgaa gtgggccaag    2160
gccctgcccg gcttcaggaa cctgcacgtg gacgaccaga tggccgtgat ccagtacagc    2220
tggatgggcc tgatggtgtt cgccatgggc tggaggagct tcaccaacgt gaacagcagg    2280
atgctgtact tcgcccccga cctggtgttc aacgagtaca ggatgcacaa gagcaggatg    2340
tacagccagt gcgtgaggat gaggcacctg agccaggagt tcggctggct gcagatcacc    2400
ccccaggagt tcctgtgcat gaaggccctg ctgctgttca gcatcatccc cgtggacggc    2460
ctgaagaacc agaagttctt cgacgagctg aggatgaact acatcaagga gctgacaggg    2520
atcatcgcct gcaagaggaa gaaccccacc agctgcagca ggaggttcta ccagctgacc    2580
aagctgctgg acagcgtgca gcccatcgcc agggagctgc accagttcac cttcgacctg    2640
ctgatcaaga gccacatggt gagcgtggac ttccccgaga tgatggccga gatcatcagc    2700
gtgcaggtgc ccaagatcct gagcggcaag gtgaagccca tctacttcca cacccag      2757
```

-continued

```
<210> SEQ ID NO 10
<211> LENGTH: 919
<212> TYPE: PRT
<213> ORGANISM: Homo sapiens

<400> SEQUENCE: 10

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Glu Thr
65                  70                  75                  80

Ser Pro Arg Gln Gln Gln Gln Gln Gly Glu Asp Gly Ser Pro Gln
                85                  90                  95

Ala His Arg Arg Gly Pro Thr Gly Tyr Leu Val Leu Asp Glu Glu Gln
            100                 105                 110

Gln Pro Ser Gln Pro Gln Ser Ala Leu Glu Cys His Pro Glu Arg Gly
        115                 120                 125

Cys Val Pro Glu Pro Gly Ala Ala Val Ala Ala Ser Lys Gly Leu Pro
    130                 135                 140

Gln Gln Leu Pro Ala Pro Pro Asp Glu Asp Asp Ser Ala Ala Pro Ser
145                 150                 155                 160

Thr Leu Ser Leu Leu Gly Pro Thr Phe Pro Gly Leu Ser Ser Cys Ser
                165                 170                 175

Ala Asp Leu Lys Asp Ile Leu Ser Glu Ala Ser Thr Met Gln Leu Leu
            180                 185                 190

Gln Gln Gln Gln Gln Glu Ala Val Ser Glu Gly Ser Ser Ser Gly Arg
        195                 200                 205

Ala Arg Glu Ala Ser Gly Ala Pro Thr Ser Ser Lys Asp Asn Tyr Leu
    210                 215                 220

Gly Gly Thr Ser Thr Ile Ser Asp Asn Ala Lys Glu Leu Cys Lys Ala
225                 230                 235                 240

Val Ser Val Ser Met Gly Leu Gly Val Glu Ala Leu Glu His Leu Ser
                245                 250                 255

Pro Gly Glu Gln Leu Arg Gly Asp Cys Met Tyr Ala Pro Leu Leu Gly
            260                 265                 270

Val Pro Pro Ala Val Arg Pro Thr Pro Cys Ala Pro Leu Ala Glu Cys
        275                 280                 285

Lys Gly Ser Leu Leu Asp Asp Ser Ala Gly Lys Ser Thr Glu Asp Thr
    290                 295                 300

Ala Glu Tyr Ser Pro Phe Lys Gly Gly Tyr Thr Lys Gly Leu Glu Gly
305                 310                 315                 320

Glu Ser Leu Gly Cys Ser Gly Ser Ala Ala Gly Ser Ser Gly Thr
                325                 330                 335

Leu Glu Leu Pro Ser Thr Leu Ser Leu Tyr Lys Ser Gly Ala Leu Asp
            340                 345                 350

Glu Ala Ala Ala Tyr Gln Ser Arg Asp Tyr Tyr Asn Phe Pro Leu Ala
        355                 360                 365

Leu Ala Gly Pro Pro Pro Pro Pro Pro Pro His Pro His Ala Arg
    370                 375                 380
```

-continued

```
Ile Lys Leu Glu Asn Pro Leu Asp Tyr Gly Ser Ala Trp Ala Ala Ala
385                 390                 395                 400

Ala Ala Gln Cys Arg Tyr Gly Asp Leu Ala Ser Leu His Gly Ala Gly
            405                 410                 415

Ala Ala Gly Pro Gly Ser Gly Ser Pro Ser Ala Ala Ser Ser Ser
        420                 425                 430

Trp His Thr Leu Phe Thr Ala Glu Glu Gly Gln Leu Tyr Gly Pro Cys
        435                 440                 445

Gly Gly Gly Gly Gly Gly Gly Gly Gly Gly Gly Gly Gly Gly Gly Gly
        450                 455                 460

Gly Gly Gly Gly Gly Gly Gly Glu Ala Gly Ala Val Ala Pro Tyr
465                 470                 475                 480

Gly Tyr Thr Arg Pro Pro Gln Gly Leu Ala Gly Gln Glu Ser Asp Phe
            485                 490                 495

Thr Ala Pro Asp Val Trp Tyr Pro Gly Gly Met Val Ser Arg Val Pro
        500                 505                 510

Tyr Pro Ser Pro Thr Cys Val Lys Ser Glu Met Gly Pro Trp Met Asp
        515                 520                 525

Ser Tyr Ser Gly Pro Tyr Gly Asp Met Arg Leu Glu Thr Ala Arg Asp
        530                 535                 540

His Val Leu Pro Ile Asp Tyr Tyr Phe Pro Pro Gln Lys Thr Cys Leu
545                 550                 555                 560

Ile Cys Gly Asp Glu Ala Ser Gly Cys His Tyr Gly Ala Leu Thr Cys
            565                 570                 575

Gly Ser Cys Lys Val Phe Phe Lys Arg Ala Ala Glu Gly Lys Gln Lys
        580                 585                 590

Tyr Leu Cys Ala Ser Arg Asn Asp Cys Thr Ile Asp Lys Phe Arg Arg
        595                 600                 605

Lys Asn Cys Pro Ser Cys Arg Leu Arg Lys Cys Tyr Glu Ala Gly Met
610                 615                 620

Thr Leu Gly Ala Arg Lys Leu Lys Lys Leu Gly Asn Leu Lys Leu Gln
625                 630                 635                 640

Glu Glu Gly Glu Ala Ser Ser Thr Thr Ser Pro Thr Glu Glu Thr Thr
            645                 650                 655

Gln Lys Leu Thr Val Ser His Ile Glu Gly Tyr Glu Cys Gln Pro Ile
        660                 665                 670

Phe Leu Asn Val Leu Glu Ala Ile Glu Pro Gly Val Val Cys Ala Gly
        675                 680                 685

His Asp Asn Asn Gln Pro Asp Ser Phe Ala Ala Leu Leu Ser Ser Leu
690                 695                 700

Asn Glu Leu Gly Glu Arg Gln Leu Val His Val Val Lys Trp Ala Lys
705                 710                 715                 720

Ala Leu Pro Gly Phe Arg Asn Leu His Val Asp Asp Gln Met Ala Val
            725                 730                 735

Ile Gln Tyr Ser Trp Met Gly Leu Met Val Phe Ala Met Gly Trp Arg
        740                 745                 750

Ser Phe Thr Asn Val Asn Ser Arg Met Leu Tyr Phe Ala Pro Asp Leu
        755                 760                 765

Val Phe Asn Glu Tyr Arg Met His Lys Ser Arg Met Tyr Ser Gln Cys
        770                 775                 780

Val Arg Met Arg His Leu Ser Gln Glu Phe Gly Trp Leu Gln Ile Thr
785                 790                 795                 800
```

```
Pro Gln Glu Phe Leu Cys Met Lys Ala Leu Leu Phe Ser Ile Ile
                805                 810                 815
Pro Val Asp Gly Leu Lys Asn Gln Lys Phe Phe Asp Glu Leu Arg Met
            820                 825                 830
Asn Tyr Ile Lys Glu Leu Asp Arg Ile Ile Ala Cys Lys Arg Lys Asn
                835                 840                 845
Pro Thr Ser Cys Ser Arg Arg Phe Tyr Gln Leu Thr Lys Leu Leu Asp
        850                 855                 860
Ser Val Gln Pro Ile Ala Arg Glu Leu His Gln Phe Thr Phe Asp Leu
865                 870                 875                 880
Leu Ile Lys Ser His Met Val Ser Val Asp Phe Pro Glu Met Met Ala
                885                 890                 895
Glu Ile Ile Ser Val Gln Val Pro Lys Ile Leu Ser Gly Lys Val Lys
                900                 905                 910
Pro Ile Tyr Phe His Thr Gln
            915

<210> SEQ ID NO 11
<211> LENGTH: 45
<212> TYPE: DNA
<213> ORGANISM: Artificial Sequence
<220> FEATURE:
<223> OTHER INFORMATION: Canonical Androgen Response Element (ARE)
      sequence

<400> SEQUENCE: 11
gcttgtacag gatgttctgc atgctctaga tgtacaggat gttct                    45
```